(12) United States Patent
Spitzer et al.

(10) Patent No.: US 9,127,081 B2
(45) Date of Patent: Sep. 8, 2015

(54) TUMOR TARGETED TNF-RELATED APOPTOSIS INDUCING LIGAND FUSION POLYPEPTIDE AND NUCLEIC ACIDS ENCODING THE SAME

(71) Applicant: Washington University, Saint Louis, MO (US)

(72) Inventors: Dirk Spitzer, Webster Groves, MO (US); William G Hawkins, Olivette, MO (US)

(73) Assignee: Washington University, Saint Louis, MO (US)

( * ) Notice: Subject to any disclaimer, the term of this patent is extended or adjusted under 35 U.S.C. 154(b) by 48 days.

(21) Appl. No.: 13/892,238

(22) Filed: May 10, 2013

(65) Prior Publication Data
US 2013/0302270 A1 Nov. 14, 2013

Related U.S. Application Data

(60) Provisional application No. 61/645,058, filed on May 10, 2012.

(51) Int. Cl.

| | |
|---|---|
| C07K 14/435 | (2006.01) |
| C07K 14/52 | (2006.01) |
| C07K 14/525 | (2006.01) |
| C07K 14/705 | (2006.01) |
| A61K 38/16 | (2006.01) |
| A61K 38/17 | (2006.01) |
| A61P 35/00 | (2006.01) |
| C12N 15/09 | (2006.01) |
| C12N 15/11 | (2006.01) |
| C12N 15/62 | (2006.01) |
| C12N 15/63 | (2006.01) |
| C07K 14/47 | (2006.01) |
| A61K 38/19 | (2006.01) |
| C12N 15/70 | (2006.01) |
| C12N 15/74 | (2006.01) |
| C12N 15/79 | (2006.01) |

(52) U.S. Cl.
CPC ............ C07K 14/4747 (2013.01); A61K 38/17 (2013.01); C07K 14/70575 (2013.01); C12N 15/62 (2013.01); C12N 15/63 (2013.01); *A61K 38/177* (2013.01); *A61K 38/191* (2013.01); *C07K 14/525* (2013.01); *C07K 14/705* (2013.01); *C07K 2319/00* (2013.01); *C07K 2319/21* (2013.01); *C07K 2319/33* (2013.01); *C12N 15/70* (2013.01); *C12N 15/74* (2013.01); *C12N 15/79* (2013.01)

(58) Field of Classification Search
None
See application file for complete search history.

(56) References Cited

U.S. PATENT DOCUMENTS

| | | | |
|---|---|---|---|
| 6,153,430 A | 11/2000 | Pastan et al. | |
| 8,461,311 B2 | 6/2013 | Hawkins et al. | |
| 2005/0282223 A1 | 12/2005 | Tittle et al. | |
| 2007/0286843 A1 * | 12/2007 | Pfizenmaier et al. | 424/93.1 |
| 2011/0236385 A1 | 9/2011 | Ho et al. | |
| 2011/0300629 A1 * | 12/2011 | Hawkins et al. | 435/375 |

FOREIGN PATENT DOCUMENTS

WO PCT/US2000/031692 11/2000
WO WO-2010010051 A1 * 1/2010

OTHER PUBLICATIONS

Garg et al. Novel treatment option for MUC16-positive malignancies with the targeted TRAIL-based fusion protein Meso-TR3. BMC Cancer 14: 35, 2014; 12 pages.*
Hawkins et al. A novel form of recombinant Trail as a platform technology to fight (pancreatic) cancer. J Surgical Res 158(2): p. 397, #55.20, 2010.*
Hung et al. A DNA vaccine encoding a single-chain trimer of HLA-A2 linked to human mesothelin peptide generates anti-tumor effects against human mesothelin-expressing tumors. Vaccine 25: 127-135, 2007.*
Spitzer et al. Trail is sterically incapable of engaging death receptors in an autocrine fashion: implications for Trail-based cancer immunotherapies. Abstracts for the 26th Annual Scientific Meeting of the Society for Immunotherapy of Cancer; Nov. 4-6, 2011; Abstract #145.*
Lakshmanan et al. MUC16 induced rapid G2/M transition via interactions with JAK2 for increased proliferation and anti-apoptosis in breast cancer cells. Oncogene 31: 805-817, published online Jul. 25, 2011.*
Ashkenazi, A., et al. Safety and antitumor activity of recombinant soluble Apo2 ligand. J. Clin. Invest (1999) 104:155.
Bergan, L, et al. Development and in vitro validation of anti-mesothelin biobodies that prevent CA125/Mesothelin-dependent cell attachment. Cancer Lett. (2007) 255:263.

(Continued)

*Primary Examiner* — Bridget E Bunner
(74) *Attorney, Agent, or Firm* — Saul L. Zackson; Zackson Law LLC

(57) ABSTRACT

Fusion polypeptides comprising a TRAIL trimer and a targeting domain are disclosed. The targeting domain can be, in some embodiments, a sequence that binds MUC16, which is prevalent on some tumor cells such as pancreatic and ovarian tumor cells. A sequence that binds MUC 16 can be mesothelin or a MUC16-binding fragment thereof, such as amino acids 1-64 of mesothelin. A fusion polypeptide of the present teachings can induce apoptosis in a target cell such as a MUC16-expressing cancer cell. Also disclosed are nucleic acids encoding the fusion polypeptides, and methods of use of the fusion polypeptides and nucleic acids.

16 Claims, 14 Drawing Sheets
(5 of 14 Drawing Sheet(s) Filed in Color)

(56) References Cited

OTHER PUBLICATIONS

Bremer, E., et al. Target cell-restricted and -enhanced apoptosis induction by a scFv:sTRAIL fusion protein with specificity for the pancarcinoma-associated antigen EGP2. Int J Cancer. (2004) 109:281-90.

Bremer, E., et al. Targeted delivery of a designed sTRAIL mutant results in superior apoptotic activity towards EGFR-positive tumor cells. J Mol Med. (2008) 86:909-24.

Cha, SS., et al. 2.8 a resolution crystal structure of human TRAIL, a cytokine with selective antitumor activity. Immunity. (1999) 11:253-61.

Chang, K., et al. Molecular cloning of mesothelin, a differentiation antigen present on mesothelium, mesotheliomas, and ovarian cancers. Proc. Natl. Acad. Sci. (1995) 93:136.

Garber K. New apoptosis drugs face critical test. Nat Biotechnol. (2005) 23:409-11.

Griffith,T.S., et al. TRAIL gene therapy: from preclinical development to clinical application. Curr Gene Ther. (2009) 9:9-19.

Gubbels, J. A., et al. Mesothelin-MUC16 binding is a high affinity, N-glycan dependent interaction that facilitates peritonealmetastasis of ovarian tumors. Mol. Cancer (2006) 5:50.

Herbst, R. S., Phase I dose-escalation study of recombinant human Apo2L/TRAIL, a dual proapoptotic receptor agonist, in patients with advanced cancer. J. Clin. Oncol. (2010) 28:2839.

Hymowitz S.G., et al. Triggering cell death: the crystal structure of Apo2L/TRAIL in a complex with death receptor 5. Mol Cell. (1999) 4:563-71.

Krippner-Heidenreich, A., et al. Single-chain TNF, a TNF derivative with enhanced stability and antitumoral activity. J Immunol. (2008) 180:8176-83.

Lane, D., et al. Differential induction of apoptosis by tumor necrosis factor-related apoptosis-inducing ligand in human ovarian carcinoma cells. Gynecol. Oncol. (2004) 93:594.

Leblanc, H.N., et al. Apo2L/TRAIL and its death and decoy receptors. Cell Death Differ (2003) 10:66-75.

Merino, D., et al. TRAIL in cancer therapy: present and future challenges. Expert Opin Ther Targets. (2007) 11:1299-314.

Mongkolsapaya, J., et al. Structure of the TRAIL-DR5 complex reveals mechanisms conferring specificity in apoptotic initiation. Nat Struct Biol. (1999) 6:1048-53.

Muhlenbeck, F., et al.The tumor necrosis factor-related apoptosis-inducing ligand receptors TRAIL-R1 and TRAIL-R2 have distinct cross-linking requirements for initiation of apoptosis and are non-redundant in JNK activation. J. Biol. Chem. (2000) 275:32208.

Rump, A., et al. Binding of ovarian cancer antigen CA125/MUC16 to mesothelin mediates cell adhesion. J. Biol. Chem. (2004) 279:9190.

Schneider, B., et al. Potent antitumoral activity of TRAIL through generation of tumor-targeted single-chain fusion proteins. Cell Death Dis. (Aug. 26, 2010);1:e68.

Scholler, N., et al. Development of a CA125-mesothelin cell adhesion assay as a screening tool for biologics discovery. (2007) Cancer Lett. 247:130.

Singh, A. P., et a;. Inhibition of MUC4 expression suppresses pancreatic tumor cell growth and metastasis. Cancer Res. (2004) 64:622.

Spitzer, D., et al. A genetically encoded multifunctional TRAIL trimer facilitates cell-specific targeting and tumor cell killing. Mol. Cancer Ther. (2010) 9:2142.

Siegemund, M. et al. Superior antitumoral activity of dimerized targeted single-chain TRAIL fusion proteins under retention of tumor selectivity. Cell Death Dis. (Apr. 12, 2012);3:e295.

Ten, C.B., et al. A novel AML-selective TRAIL fusion protein that is superior to Gemtuzumab Ozogamicin in terms of in vitro selectivity, activity and stability. Leukemia. (2009) 23:1389-97.

Walczak, H., et al. Tumoricidal activity of tumor necrosis factor-related apoptosis-inducing ligand in vivo. Nat Med. (1999) 5:157-63.

Walczak, H., et al. The CD95 (APO-1/Fas) and the TRAIL (APO-2L) apoptosis systems. Exp. Cell Res. (2000) 256:58.

Kelley, R.F., et al. Receptor-selective mutants of apoptosis-inducing ligand 2/tumor necrosis factor-related apoptosis-inducing ligand reveal a greater contribution of death receptor (DR) 5 than DR4 to apoptosis signaling. J Biol Chem (2005) 280:2205-12.

Wajant, H., et al. Differential activation of TRAIL-R1 and -2 by soluble and membrane TRAIL allows selective surface antigen-directed activation of TRAIL-R2 by a soluble TRAIL derivative. Oncogene (2001) 20:4101.

Xiang, X, et al. HN125: A Novel Immunoadhesin Targeting MUC16 with Potential for Cancer Therapy. J Cancer (2011) 2:280-291.

Wiley, S.R., et al. Identification and characterization of a new member of the TNF family that induces apoptosis. Immunity. (1995) 3:673-82.

De Bruyn, M., et al. Cell surface delivery of TRAIL strongly augments the tumoricidal activity of T cells. Clin Cancer Res. (Sep. 1, 2011);17(17):5626-37.

Pitti, R. M., et al. Induction of apoptosis by Apo-2 ligand, a new member of the tumor necrosis factor cytokine family. J. Biol. Chem. (1996) 271:12687.

Haridas, D., et al. Pathobiological implications of MUC16 expression in pancreatic cancer. PLoS. One. (2011) 6:e26839.

Wu, Y. M., et al. Mucin glycosylation is altered by pro-inflammatory signaling in pancreatic-cancer cells. J. Proteome. Res. (2009) 8:1876.

Moritani, S., et al. Serous papillary adenocarcinoma of the female genital organs and invasive micropapillary carcinoma of the breast. Are WT1, CA125, and GCDFP-15 useful in differential diagnosis? Hum. Pathol. (2008) 39:666.

Hassan, R., et al. Mesothelin: a new target for immunotherapy. Clin. Cancer Res. (2004) 10:3937.

Lane, D., et al. Acquired resistance to TRAIL-induced apoptosis in human ovarian cancer cells is conferred by increased turnover of mature caspase-3. Mol. Cancer Ther. (2006) 5:509.

Reis, C. R., et al. Rapid and efficient cancer cell killing mediated by high-affinity death receptor homotrimerizing TRAIL variants. Cell Death. Dis. (2010) 1:e83.

Fesik, S.W., et al. Promoting apoptosis as a strategy for cancer drug discovery. Nat Rev Cancer (2005) 5:876-85.

DeVries, E.G., et al. Tumor necrosis factor-related apoptosis-inducing ligand pathway and its therapeutic implications. Clin Cancer Res (2006) 12:2390-3.

Falschlehner, C., et al. TRAIL signalling: decisions between life and death. Int J Biochem Cell Biol (2007) 39:1462-75.

Bodmer, J.L. et al. Cysteine 230 is essential for the structure and activity of the cytotoxic ligand TRAIL. J Biol Chem (2000) 275:20632-7.

Cha, S.S., et al. Crystal structure of TRAILDR5 complex identifies a critical role of the unique frame insertion in conferring recognition specificity. J Biol Chem (2000) 275: 31171-7.

Wilson, N. S., et al. Proapoptotic activation of death receptor 5 on tumor endothelial cells disrupts the vasculature and reduces tumor growth. Cancer Cell (2012) 22:80.

\* cited by examiner

TUMOR TARGETED TNF-RELATED APOPTOSIS INDUCING LIGAND FUSION POLYPEPTIDE AND NUCLEIC ACIDS ENCODING THE SAME

CROSS-REFERENCE TO RELATED APPLICATION

This application claims benefit of priority from U.S. Provisional Patent Application 61/645,058 filed May 10, 2012. The Provisional application is incorporated by reference in its entirety.

STATEMENT REGARDING FEDERALLY SPONSORED RESEARCH OR DEVELOPMENT

This invention was made with government support under Grants 5P30CA9184208 and 1R21CA150945 awarded by the National Institutes of Health. The Government has certain rights in the invention.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

Pancreatic cancer is among those malignancies with the worst prognoses in the United States in 2010 (Jemal, A., et al. CA Cancer J. Clin. 60:277-300, 2010). There has been little progress in the management of the disease and the annual mortality rate remains nearly identical to the annual incidence rate. The five-year survival for pancreatic cancer patients is ~4%.

Transformed cancer cells can often be distinguished from normal tissues by changes in expression patterns of certain cellular markers. Two cell surface antigens with expression levels that can exceed normal levels in cancer cells are mesothelin and MUC16 (also known as CA-125).

Mesothelin is a GPI-linked cell surface glycoprotein that is believed to participate in tumor adhesion and dissemination including formation of metastases (Hassan, R., et al. Clin. Cancer Res. 10:3937-42, 2004). Mesothelin is expressed in mesothelial cells with limited expression in other normal cell types. Expression of mesothelin can be substantially up-regulated in human pancreas and ovarian cancers. For example, analyses of human pancreas cancers have shown greater than 3 fold up-regulation of mesothelin gene expression (Iacobuzio-Donahue, C. A., et al. Cancer Res. 63:8614-22, 2003). In one study, mesothelin expression was identified in pancreas adenocarcinomas (the far majority of pancreas cancers are ductal adenocarcinomas, PDACs) in all 60 patients examined by immunohistochemistry (Argani, P., et al. Clin. Cancer Res. 7:3862-8, 2001). In addition, mesothelin overexpression is commonly found in ovarian malignancies, lung cancer, and mesotheliomas (Ho, M., et al. Clin. Cancer Res. 13:1571-5, 2007; Muminova, Z. E., et al. BMC Cancer. 4:19, 2004; Ho, M., et al. Clin. Cancer Res. 11:3814-20, 2005). In addition, there is evidence that overexpression of mesothelin may be essential for progression of pancreas cancer, (Li, M., et al. Mol. Cancer Ther. 7:286-96, 2008). It has been shown that the N-terminal 64 amino acid sequence of mesothelin includes the minimal binding sequence required for MUC16 binding (Xiang, X., et al., J. Cancer 2: 280-291, 2011).

MUC16 (CA125) belongs to a group of mucins expressed on epithelial cells (Kufe, D. W. Nat. Rev. Cancer. 9:874-85, 2009). MUC16 is transmembrane anchored. In addition, patients with pancreatic cancer can have serum MUC16 levels that can be nearly 40-fold increased compared to healthy controls or patients with benign pancreatic lesions (Brand, R. E., et al. Clin. Cancer Res. 17:805-16, 2011). Membrane-bound MUC16 binds to native mesothelin with high affinity, whereas soluble MUC16 has only a weak affinity for mesothelin (Rump, A., et al. J. Biol. Chem. 279:9190-8, 2004; Bast, R. C., et al. Int. J. Gynecol. Cancer. 15:274-81, 2005; Gubbels, J. A., et al. Mol. Cancer. 5:50, 2006).

TNF-related apoptosis-inducing ligand (TRAIL) has been shown to exhibit potent apoptotic activity against tumor cells with lower toxicity to non-transformed cells following engagement with cellular receptors expressed abundantly on tumor cells (Falschlehner, C., et al. J. Biochem. Cell Bio. 39:1462-1475, 2007). TRAIL stimulates the extrinsic death pathway. Native, soluble TRAIL exists as a homotrimer in vivo (Kohlhaas, S. L., et al. J. Biol. Chem. 282: 12831-12841, 2007). The sequence of human TRAIL amino acids 91-281 is:

MILRTSEETISTVQEKQQNISPLVRERG-PQRVAAHITGTRGRSNTLSSPNSKNEKA LGR-KINSWESSRSGHSFLSNLHLRNGELVI-HEKGFYYIYSQTYFRFQEEIKENTKNDKQM VQYIYKYTSYPDPILLMKSARN-SCWSKDAEYGLYSIYQGGIFELKENDRIFVSVTNEHLI DMDHEASFFGAFLVG (SEQ ID NO: 1).

Recombinant TRAIL has been produced in bacteria exclusively from monomeric cDNAs. However, the activity of recombinant TRAIL depends on trimerization (Spitzer, D., et al., Mol. Cancer Ther. 9: 2142-2151, 2010). Numerous design modifications have been used to generate molecules comprising trimerized TRAIL sequences, such as: tagging with FLAG sequence or His-tagging, with tag-mediated crosslinking; addition of leucine zipper [LZ] and/or isoleucine zipper [ILZ] sequences, with stabilization of TR3 trimers with cations [i.e., zinc] (Merino, D., et al. Expert Opin. Ther. Targets. 11: 1299-1314, 2007). However, such attempts to produce bioactive TRAIL from monomeric cDNAs in mammalian cells have failed. Such failures have been attributed to intermolecular disulfide bridge formation via TRAIL's unique cysteine at amino acid 230, resulting in a non-functional death receptor ligand (Bodmer, J. L., et al., J. Biol. Chem. 275: 20632-20637, 2000).

Previously, the present inventors developed bioactive TRAIL trimers ("TR3") (U.S. patent application Ser. No. 13/155,577, published as US Patent Application Publication 2011/0300629 A1; Spitzer, D., et al., Mol. Cancer Ther. 9: 2142-2151, 2010). Furthermore, the present inventors also developed numerous modifications to further enhance TR3's pharmacologic properties over conventional TRAIL, including enhanced temperature stability and prolonged in vivo half-life (Spitzer, D., et al. Mol. Cancer Ther. 9:2142-51, 2010).

However, there is an unmet need for therapeutically active compositions that can induce cell death in tumor cell targets.

SUMMARY

In view of the unmet need for therapeutically effective reagents that target and cause death of tumor cells while minimizing toxicity to non-cancerous cells, the present inventors disclose fusion polypeptides comprising TRAIL trimers and targeting domains, and nucleic acids comprising sequences encoding such fusion polypeptides. In various embodiments, a fusion polypeptide of the present teachings can comprise, consist essentially of, or consist of a sequence of a TRAIL trimer plus a polypeptide sequence that can target a tumor cell such as, for example, a tumor cell that expresses abnormally high levels of a cell surface receptor such as MUC16. In various embodiments, a fusion polypeptide of the present teachings can comprise, consist essentially of, or consist of a sequence of a TRAIL trimer and a polypeptide sequence that can target a TRAIL trimer to a tumor cell such as, for example and without limitation, a pancreatic tumor cell or an ovarian cancer cell. In various embodiments, a fusion polypeptide of the present teachings can comprise, consist essentially of, or consist of a sequence of a TRAIL trimer plus a targeting sequence such as a mesothelin polypeptide. In various embodiments, the sequence of a mesothelin polypeptide can be that of a full length mesothelin, or a mesothelin of less than full length but retains MUC16 binding activity. In various embodiments, a fusion polypeptide of the present teachings can comprise, consist essentially of, or consist of a TRAIL trimer sequence plus a mesothelin sequence absent the GPI anchor. In various embodiments, a fusion polypeptide of the present teachings can comprise, consist essentially of, or consist of a TRAIL trimer sequence plus an N-terminal peptide sequence of mesothelin, such as, without limitation, the 64 amino acid sequence of the N-terminal of human mesothelin. In various embodiments, a fusion polypeptide of the present teachings can further comprise one or more linker sequences such as described in U.S. patent application Ser. No. 13/155,577 filed Jun. 8, 2011, published as US Patent Application Publication 2011/0300629 A1, and Spitzer, D., et al., Mol. Cancer Ther. 9: 2142-2151, 2010 which are hereby incorporated by reference, each in its entirety. In some configurations, a spacer can comprise, consist essentially of, or consist of one or more short consensus repeats (SCRs). In various configurations, a spacer can comprise, consist essentially of, or consist of one SCR, two SCRs, three SCRs or four SCRs. In some configurations, a fusion polypeptide can further comprise a tag sequence, such as, without limitation, a 6-His tag sequence and/or a FLAG sequence.

In various embodiments, a fusion polypeptide of the present teachings can be selected from the group consisting of complete mesothelin-TR3 (i.e., a fusion polypeptide comprising full-length mesothelin, plus TR3); mesothelinΔGPI-TR3 (i.e., a fusion polypeptide comprising mesothelin consisting of GPI-anchor-deleted mesothelin, plus TR3) and meso64-TR3 (i.e., a fusion polypeptide comprising a mesothelin consisting of the N-terminal 64 amino acids of mesothelin, plus TR3).

In various embodiments, the present teachings further include nucleic acids that encode any of the fusion polypeptides disclosed herein, as well as vectors such as viruses and plasmids comprising a nucleic acid that encodes any of the fusion polypeptides disclosed herein.

In some embodiments, a fusion polypeptide of the present teachings does not activate cell death pathways when contacted with a MUC16-negative cell at a concentration at which a TRAIL trimer alone (i.e., without mesothelin) activates cell death pathways in a MUC16-negative cell.

In some embodiments, a fusion polypeptide of the present teachings can bind to the surface of cells expressing MUC16, such as, for example, pancreatic or ovarian tumor cells.

In some embodiments, a fusion polypeptide of the present teachings can induce apoptosis in cells that express MUC16 such as tumor cells that express MUC16.

In some embodiments, a fusion polypeptide of the present teachings can block native binding sites of MUC16 in cells expressing MUC16, such as, for example, pancreatic or ovarian tumor cells.

In some embodiments, a fusion polypeptide of the present teachings can reduce metastatic potential of tumor cells that express MUC16.

Various embodiments of the present teachings include methods of treating cancer. In various configurations, these methods comprise administering to a subject in need thereof a therapeutically effective amount of a fusion polypeptide of the present teachings. In various configurations, the methods comprise administering to a subject in need thereof a therapeutically effective amount of a vector such as a plasmid or virus comprising a nucleic acid encoding a fusion polypeptide of the present teachings.

In various embodiments, methods of the present teachings include methods of inducing apoptosis in a cell that expresses MUC16 such as a tumor cell that expresses MUC16. In various configurations, these methods include contacting a cell that expresses MUC16 with a polypeptide of the present teachings, or a nucleic acid or vector of the present teachings. In various configurations, a fusion polypeptide or nucleic acid can be administered in an amount sufficient to cause apoptosis in a cell that expresses MUC16 without inducing apoptosis in other cells.

In various embodiments, methods of the present teachings include methods of blocking native binding sites of MUC16. In these methods, a fusion polypeptide of the present teachings or a nucleic acid encoding a fusion polypeptide of the present teachings is administered or applied to a cell expressing MUC16.

In various embodiments, methods of the present teachings include methods of reducing metastatic potential. In these methods, a fusion polypeptide of the present teachings or a nucleic acid encoding a fusion polypeptide of the present teachings is administered or applied to a cell expressing MUC16.

In various embodiments, methods of the present teachings include methods of killing MUC16-positive cells in a population of cells. In various configurations, these methods comprise contacting the cells of a population of cells with an effective amount of a fusion polypeptide or a nucleic acid of the present teachings, whereby >70% of MUC16-positive cells are killed, i.e., at a percentage greater than a "chemotherapeutic plateau."

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
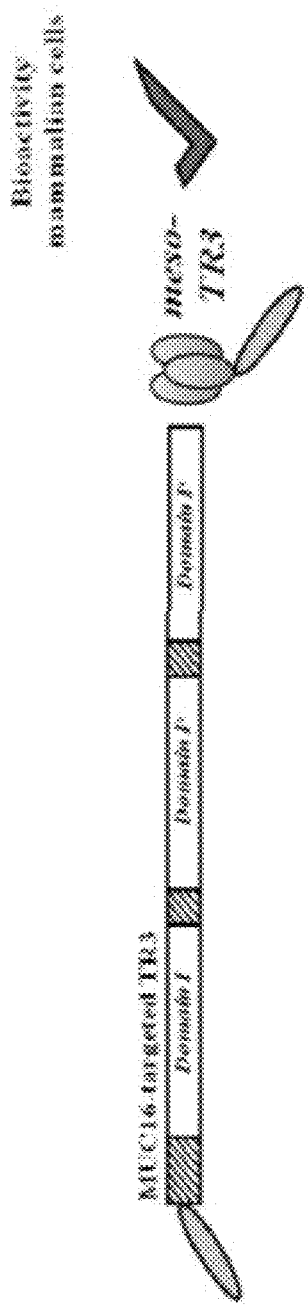
FIG. 1 illustrates a fusion polypeptide of the present teachings.

A desired feature of a therapeutic is that after systemic application, it seeks its target automatically, ignores all non-targets and, when arrived at its destination fully unleashes its intended pharmacologic activity, in analogy of a "magic bullet". Such a selective activity profile can be beneficial for the treatment of human malignancies, for example when treatment with conventional chemotherapy is known to be associated with debilitating side effects directly linked to an adverse impact on the quality of life of the patients.

Nearly 20 years ago, the TNF superfamily member TRAIL was identified as a potential cancer therapeutic because of its strong apoptosis induction on transformed cancer cells and lack of harmful side effects for the host. Since then, TRAIL has been evaluated in a number of clinical trials and found to be effective against several types of cancers (Herbst, R. S., et al., J. Clin. Oncol. 28:2839, 2010). Investigators have looked for ways to stabilize the bioactive trimer by a number of attempts, such as adding $Zn^{2+}$ to the production process which is believed to aid the coordination of the free cysteines (Mahalingam, D., et al., Cancer Treat. Rev. 35:280, 2009). Incorporation of targeting moieties directed against cancer-specific surface markers was also investigated. In these studies, cancer targeting was primarily achieved using antibody fragments (scFv) on the basis of the conventional monomeric TRAIL platform (Bremer, E., et al., Int. J. Cancer 109:281, 2004, ten Cate, B., et al., Leukemia 23:1389, 2009). This technology turned out to be quite effective, despite a 1:1 stoichiometry of the targeting and effector domain of the fusion proteins which could potentially interfere with the formation of bioactive TRAIL trimers, resulting in unpredictable drug properties. In fact, we have produced scFv-TRAIL fusion proteins employing two different antibody fragments with one drug being constitutively active while the other drug was completely inactive in the absence of the target antigen.

The present inventors have recently designed a new method to produce bioactive soluble TRAIL from mammalian cells, designated TR3. Despite its much enhanced stability, this genetically fused TRAIL trimer has the capacity to serve as a drug platform for the design of targeted TRAIL therapy under stoichiometric control. This has been shown by fusing a scFv to the N-terminus of TR3 which resulted in a RBC-targeted scFv-TR3 fusion protein with a favorable 1:3 stoichiometry that was capable of tethering human TR3 to mouse RBCs which were converted into potent effector surfaces in analogy to nanoparticles, only capable of facilitating bystander killing (Spitzer, D., et al., Mol. Cancer Ther. 9:2142, 2010). In the instant application, we have described the in vitro characterization of a tumor-targeted variant of TR3 by harnessing the strong binding affinity of the two well described biomarkers mesothelin and MUC16. Instead of targeting TR3 via an antibody fragment to the desired cancer cells, the present inventors generated Meso-TR3, in which the mature form of secreted human mesothelin was placed at the N-terminus of human TR3. Meso-TR3 bound abundantly to endogenous MUC16, identical to soluble mesothelin itself and triggered a much enhanced death pathway than the parental drug TR3. These results had important implications because they confirmed that the mesothelin targeting domain was not masked by TR3 as it was still accessible to interact with membrane-associated MUC16. This interaction is important because it not only imparts target selectivity to Meso-TR3, but also serves to anchor soluble TRAIL to the surface of MUC16-positive cancer cells, thus converting it into a membrane bound TRAIL.

This conversion has been proposed to lead a more efficient receptor crosslinking (particularly important for DR5-mediated apoptosis), which in turn provides a more potent death signal resulting in an enhanced apoptosis compared to its soluble counterpart (Muhlenbeck, F., et al., J. Biol. Chem. 275:32208, 2000).

The importance of TRAIL receptor crosslinking in cell death is further exemplified by an enhanced induction of apoptosis noted in our experimental system upon adding mesothelin antibody to dimerize Meso-TR3, ultimately resulting in a more efficient TRAIL receptor crosslinking (FIG. 7D). Another potentially important aspect of the binding of mesothelin to MUC16 is that it may contribute to both homotypic (tumor cell-tumor cell) and heterotypic (tumor cell-mesothelial cell) cell interactions (Singh, A. P., et al., Cancer Res. 64:622, 2004). The latter type of cell interaction is believed to promote adherence of tumor cells to the peritoneum, resulting in metastatic spread of the primary lesion into the abdomen (Gubbels, J. A., et al., Mol. Cancer 5:50, 2006; Rump, A., J. Biol. Chem. 279:9190, 2004; Scholler, N., et al., Cancer Lett. 247:130, 2007). These considerations suggest that by virtue of binding to MUC16, Meso-TR3 may also block the mesothelin/MUC16-dependent cell adhesion thus limiting the peritoneal dissemination of tumor cells in addition to facilitating enhanced TRAIL-mediated target cell death (Bergan, L., Cancer Lett. 255:263, 2007).

While the TR3 effector domain of Meso-TR3 did not seem to sterically interfere with binding the drug to MUC16, we noticed potential limitations with regard to TR3 binding to the DR5 receptor on MUC16-deficient targets. Based on semi-quantitative Western blot analysis, an ≈8-fold higher concentration of Meso-TR3 was required to achieve the same biological effect as untargeted TR3 on MUC16-deficient Jurkat cells. This finding was somewhat inconsistent with our earlier report in which we did not observe detrimental effects on the killing activity of a variety of domain additions engineered onto the TR3 drug platform (Spitzer, D., et al., Mol. Cancer Ther. 9:2142, 2010). A possible explanation for this finding is that, in its native state, the steric relationship between mesothelin and TR3 in the context of the Meso-TR3 fusion protein might be such that it partially masks the TR3 molecule and makes it less accessible to the death receptors in target antigen negative cells (FIG. 9B, left panel). However, when the mesothelin targeting moiety is bound to MUC16, exposure of the TR3 trimer is enabled and results in an unrestricted accessibility with the surface-associated death receptor(s). We therefore propose that these structural changes, in combination with a now membrane tethered TR3 are responsible for Meso-TR3 to acquire its full cytotoxic potential at the target cell membrane (FIG. 9B, right panel).

In summary, the present inventors have described the in vitro characterization of a downstream modification of the novel TRAIL-based drug platform TR3. Soluble Meso-TR3 targets the cancer biomarker MUC16 and exhibits all features of a traditional TRAIL-based cancer drug, combined with enhanced stability, killing capacity and favorable 1:3 stoichiometry of targeting (mesothelin) and effector domain (TR3).

Methods

The methods and compositions described herein utilize laboratory techniques well known to skilled artisans, and can be found in references such as Sambrook and Russel (2006), Condensed Protocols from Molecular Cloning: A Laboratory Manual, Cold Spring Harbor Laboratory Press, ISBN 0879697717; Sambrook and Russel (2001) Molecular Cloning: A Laboratory Manual, Cold Spring Harbor Laboratory Press, ISBN 0879695773; Ausubel et al. (2002) Short Protocols in Molecular Biology, Current Protocols, ISBN 0471250929; Spector et al. (1998) Cells: A Laboratory Manual, Cold Spring Harbor Laboratory Press, ISBN 0879695226. As used herein, "TRAIL" can refer to full-length TRAIL polypeptide, or a domain thereof, such as TRAIL I domain (amino acids 91-113 human TRAIL) or TRAIL I' domain (amino acids 108-113 human TRAIL).

Non-limiting examples of fusion polypeptides of the present teachings include, in amino-terminal-to carboxy terminal order:

1. Mesothelin-TRAIL domain I-TRAIL domain I'-TRAIL domain I', wherein "mesothelin" is full-length human mesothelin; TRAIL domain I is human TRAIL fragment aa 91-113, TRAIL domain I' is human TRAIL fragment aa 108-113.

2. Mesothelin-TRAIL domain I-TRAIL domain I'-TRAIL domain I' wherein "mesothelin" is human mesothelin from which carboxy terminal sequence comprising the GPI anchor domain had been deleted; TRAIL domain I is human TRAIL fragment aa 91-113, TRAIL domain is human TRAIL fragment aa 108-113.

3. Mesothelin-TRAIL domain I-TRAIL domain I'-TRAIL domain I' wherein "mesothelin" consists of amino acids 1-64 of human mesothelin; TRAIL domain I is human TRAIL fragment aa 91-113, TRAIL domain is human TRAIL fragment aa 108-113.

4. Mesothelin-TRAIL domain I-TRAIL domain I'-TRAIL domain I' wherein "mesothelin" is a human mesothelin fragment that binds MUC16, such as without limitation amino acids 1-64; TRAIL domain I is human TRAIL fragment aa 91-113, TRAIL domain I' is human TRAIL fragment aa 108-113.

Vectors

Examples of vectors of the present teachings include, without limitation, plasmids of the following sequences.

Figure 10:
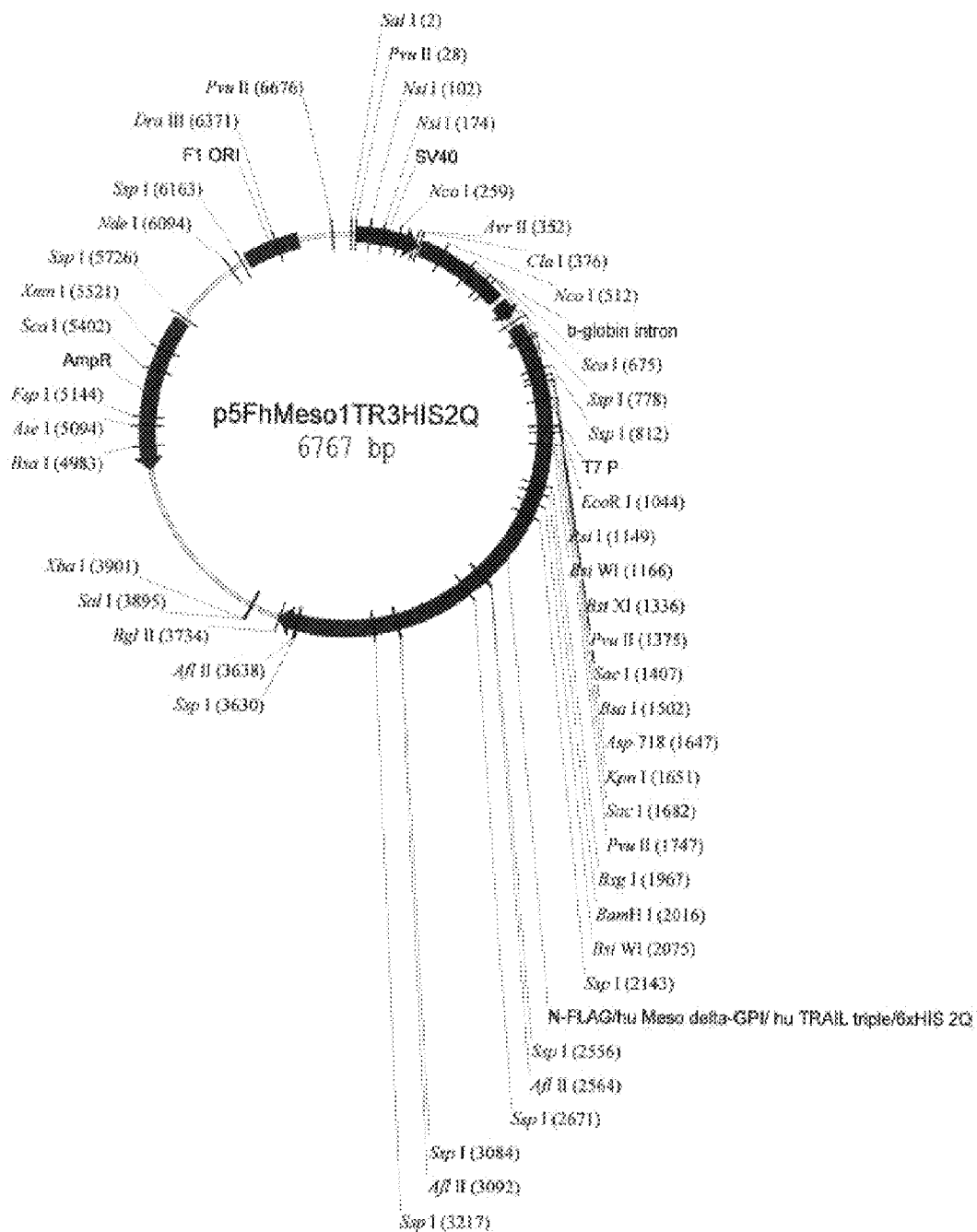
FIG. 10 illustrates a restriction map of plasmid p5FhMeso64TR3HIS2Q.

```
p5FhMeso64TR3HIS2Q (6113 BP) (FIG. 10)
                                                      (SEQ ID NO: 2)
        gtcgacttct gaggcggaaa gaaccagctg tggaatgtgt gtcagttagg gtgtggaaag    60
tccccaggct ceccageagg cagaagtatg caaagcatgc atctcaatta gtcagcaacc   120
aggtgtggaa agtccccagg ctccccagca ggcagaagta tgcaaagcat gcatctcaat   180
tagtcagcaa ccatagtccc gcccctaact ccgcccatcc cgcccctaac tccgcccagt   240
tccgcccatt ctccgcccca tggctgacta atttttttta tttatgcaga ggccgaggcc   300
gcctcggcct ctgagctatt ccagaagtag tgaggaggct tttttggagg cctaggcttt   360
tgcaaaaagc tggatcgatc ctgagaactt cagggtgagt ttggggaccc ttgattgttc   420 tttcttttc gctattgtaa aattcatgtt atatggaggg ggcaaagttt tcagggtgtt   480
gtttagaatg ggaagatgtc ccttgtatca ccatggaccc tcatgataat tttgtttctt   540
tcactttcta ctctgitgac aaccattgtc tcctcttatt ttcttttcat tttctgtaac   600 ttttcgtta aactttagct tgcatttgta acgaatttt aaattcactt ttgtttattt   660
gtcagattgt aagtactttc tctaatcact tttttttcaa ggcaatcagg gtatattata   720
ttgtacttca gcacagtttt agagaacaat tgttataatt aaatgataag gtagaatatt   780
tctgcatata aattctggct ggcgtggaaa tattcttatt ggtagaaaca actacatcct   840
ggtcatcatc ctgcctttct ctttatggtt acaatgatat acactgtttg agatgaggat   900
aaaatactct gagtccaaac cgggcccctc tgctaaccat gttcatgcct tcttcttttt   960
cctacagctc ctgggcaacg tgctggttat tgtgctgtct catcattttg gcaaagaatt  1020
gtaatacgac tcactatagg gcgaattcag gttctgtgga caatcacaat gggaatccaa  1080
ggagggtctg tcctgttcgg gctgctgctc gtcctggctg tcttctgcca ttcaggtcat  1140
agcctgcaga gctacaaccc tccgcgtacg gactacaagg acgatgatga caaacagatc  1200
agcggtggag gctcagaagt ggagaagaca gcctgtcctt caggcaagaa ggcccgcgag  1260
atagacgaga gcctcatctt ctacaagaag tgggagctgg aagcctgcgt ggatgcggcc  1320
ctgctggcca cccagatgga ccgcgtgaac gccatcccct tcacctacga gcagctggac  1380
```

-continued

```
gtcctaaagc ataaactgga tgagctcggt ggaggctcag gtacgccacc tatgattttg   1440
agaacctctg aggaaaccat ttctacagtt caagaaaagc aacaaaatat ttctccccta   1500
gtgagagaaa gaggtcctca gagagtagca gctcacataa ctgggaccag aggaagaagc   1560
aacacattgt cttctccaaa ctccaagaat gaaaaggctc tgggccgcaa aataaactcc   1620
tgggaatcat caaggagtgg gcattcattc ctgagcaact gcacttgag gaatggtgaa    1680 ctggtcatcc atgaaaaagg ttttactac atctattccc aaacatactt tcgatttcag    1740
gaggaaataa aagaaacac aagaacgac aaacaaatgg tccaatatat ttacaaatac     1800
acaagttatc ctgaccctat attgttgatg aaaagtgcta gaaatagttg ttggtctaaa   1860
gatgcagaat atggactcta ttccatctat caaggggaa tatttgagct taaggaaaat    1920
gacagaattt ttgtttctgt aacaaatgag cacttgatag acatggacca tgaagccagt   1980
tttttcgggg ccttttttagt tggcagatcc caaaatattt ctcccctagt gagagaaaga  2040
ggtcctcaga gagtagcagc tcacataact gggaccagag gaagaagcaa cacattgtct   2100
tctccaaact ccaagaatga aaaggctctg gccgcaaaa taaactcctg gaatcatca    2160 aggagtgggc attcattcct gagcaacttg cacttgagga atggtgaact ggtcatccat   2220
gaaaaagggt tttactacat ctattcccaa acatactttc gatttcagga ggaaataaaa   2280
gaaaacacaa gaacgacaa acaaatggtc caatatattt acaaatacac aagttatcct    2340
gaccctatat tgttgatgaa aagtgctaga aatagttgtt ggtctaaaga tgcagaatat   2400
ggactctatt ccatctatca aggggaata tttgagctta aggaaaatga cagaattttt    2460
gtttctgtaa caaatgagca cttgatagac atggaccatg aagccagttt ttcggggcc    2520 tttttagttg gcagatccca ccaccaccac caccaccaaa atatttctcc cctagtgaga   2580
gaaagaggtc ctcagagagt agcagctcac ataactggga ccagaggaag aagcaacaca   2640
ttgtcttctc caaactccaa gaatgaaaag gctctgggcc gcaaaataaa ctcctgggaa   2700
tcatcaagga gtgggcattc attcctgagc aacttgcact tgaggaatgg tgaactggtc   2760
atccatgaaa aagggtttta ctacatctat tcccaaacat actttcgatt tcaggaggaa   2820
ataaaagaaa acacaagaa cgacaaacaa atggtccaat atatttacaa atacacaagt   2880
tatcctgacc ctatattgtt gatgaaaagt gctagaaata gttgttggtc taaagatgca   2940
gaatatggac tctattccat ctatcaaggg ggaatatttg agcttaagga aaatgacaga   3000 attttttgttt ctgtaacaaa tgagcacttg atagacatgg accatgaagc cagttttttc   3060 ggggccttttt tagttggcag atcttaatct aggatcttat taaagcagaa cttgttttatt  3120 gcagcttata atggttacaa ataaagcaat agcatcacaa atttcacaaa taaagcattt   3180
ttttcactgc attctagttg tggtttgtcc aaactcatca atgtatctta tcatgtctgg   3240
tcgactctag actcttccgc ttcctcgctc actgactcgc tgcgctcggt cgttcggctg   3300
cggcgagcgg tatcagctca ctcaaaggcg gtaatacggt tatccacaga atcaggggat   3360
aacgcaggaa agaacatgtg agcaaaaggc cagcaaaagg ccaggaaccg taaaaaggcc   3420
gcgttgctgg cgtttttcca taggctccgc cccctgacg agcatcacaa aaatcgacgc     3480
tcaagtcaga ggtggcgaaa cccgacagga ctataaagat accaggcgtt tccccctgga   3540
agctccctcg tgcgctctcc tgttccgacc ctgccgctta ccggatacct gtccgccttt   3600
ctcccttcgg gaagcgtggc gctttctcaa tgctcacgct gtaggtatct cagttcggtg   3660
taggtcgttc gctccaagct gggctgtgtg cacgaacccc cgttcagccc gaccgctgc    3720 gccttatccg gtaactatcg tcttgagtcc aacccggtaa gacacgactt atcgccactg   3780
gcagcagcca ctggtaacag gattagcaga gcgaggtatg taggcggtgc tacagagttc   3840
```

-continued

```
ttgaagtggt ggcctaacta cggctacact agaaggacag tatttggtat ctgcgctctg   3900
ctgaagccag ttaccttcgg aaaaagagtt ggtagctctt gatccggcaa acaaaccacc   3960
gctggtagcg gtggtttttt tgtttgcaag cagcagatta cgcgcagaaa aaaggatct    4020 caagaagatc ctttgatctt ttctacgggg tctgacgctc agtggaacga aaactcacgt   4080
taagggattt tggtcatgag attatcaaaa aggatcttca cctagatcct tttaaattaa   4140
aaatgaagtt ttaaatcaat ctaaagtata tatgagtaaa cttggtctga cagttaccaa   4200
tgcttaatca gtgaggcacc tatctcagcg atctgtctat ttcgttcatc catagttgcc   4260
tgactccccg tcgtgtagat aactacgata cgggagggct taccatctgg ccccagtgct   4320
gcaatgatac cgcgagaccc acgctcaccg gctccagatt tatcagcaat aaaccagcca   4380
gccggaaggg ccgagcgcag aagtggtcct gcaactttat ccgcctccat ccagtctatt   4440
aattgttgcc gggaagctag agtaagtagt tcgccagtta atagtttgcg caacgttgtt   4500
gccattgcta caggcatcgt ggtgtcacgc tcgtcgtttg gtatggcttc attcagctcc   4560
ggttcccaac gatcaaggcg agttacatga tcccccatgt tgtgcaaaaa agcggttagc   4620
tccttcggtc ctccgatcgt tgtcagaagt aagttggccg cagtgttatc actcatggtt   4680
atggcagcac tgcataattc tcttactgtc atgccatccg taagatgctt ttctgtgact   4740
ggtgagtact caaccaagtc attctgagaa tagtgtatgc ggcgaccgag ttgctcttgc   4800
ccggcgtcaa tacgggataa taccgcgcca catagcagaa ctttaaaagt gctcatcatt   4860
ggaaaacgtt cttcggggcg aaaactctca aggatcttac cgctgttgag atccagttcg   4920
atgtaaccca ctcgtgcacc caactgatct tcagcatctt ttactttcac cagcgtttct   4980
gggtgagcaa aaacaggaag gcaaaatgcc gcaaaaaagg aataagggc gacacggaaa    5040 tgttgaatac tcatactctt ctttttcaa tattattgaa gcatttatca gggttattgt     5100
ctcatgagcg gatacatatt tgaatgtatt tagaaaaata aacaaatagg ggttccgcgc   5160
acatttcccc gaaaagtgcc acctgacgtc taagaaacca ttattatcat gacattaacc   5220
tataaaaata ggcgtatcac gaggccccctt tcgtctcgcg cgtttcggtg atgacggtga   5280
aaacctctga cacatgcagc tcccggagac ggtcacagct tgtctgtaag cggatgccgg   5340
gagcagacaa gcccgtcagg gcgcgtcagc gggtgttggc gggtgtcggg gctggcttaa   5400
ctatgcggca tcagagcaga ttgtactgag agtgcaccat atgcggtgtg aaataccgca   5460
cagatgcgta aggagaaaat accgcatcag gaaattgtaa acgttaatat tttgttaaaa   5520
ttcgcgttaa attttgtta aatcagctca tttttaacc aataggccga aatcggcaaa    5580
atcccttata aatcaaaaga atagaccgag atagggttga gtgttgttcc agtttggaac   5640
aagagtccac tattaaagaa cgtggactcc aacgtcaaag ggcgaaaaac cgtctatcag   5700
ggcgatggcc cactacgtga accatcaccc taatcaagtt ttttggggtc gaggtgccgt   5760
aaagcactaa atcggaaccc taaagggagc ccccgattta gagcttgacg ggaaagccg    5820 gcgaacgtgg cgagaaagga agggaagaaa gcgaaaggag cgggcgctag gcgctggca    5880 agtgtagcgg tcacgctgcg cgtaaccacc acacccgccg cgcttaatgc gccgctacag   5940
ggcgcgtcgc gccattcgcc attcaggcta cgcaactgtt gggaagggcg atcggtgcgg   6000
gcctcttcgc tattacgcca gctggcgaag ggggatgtg ctgcaaggcg attaagttgg    6060
gtaacgccag ggttttccca gtcacgacgt tgtaaaacga cggccagtga att            6113
```

Figure 11:
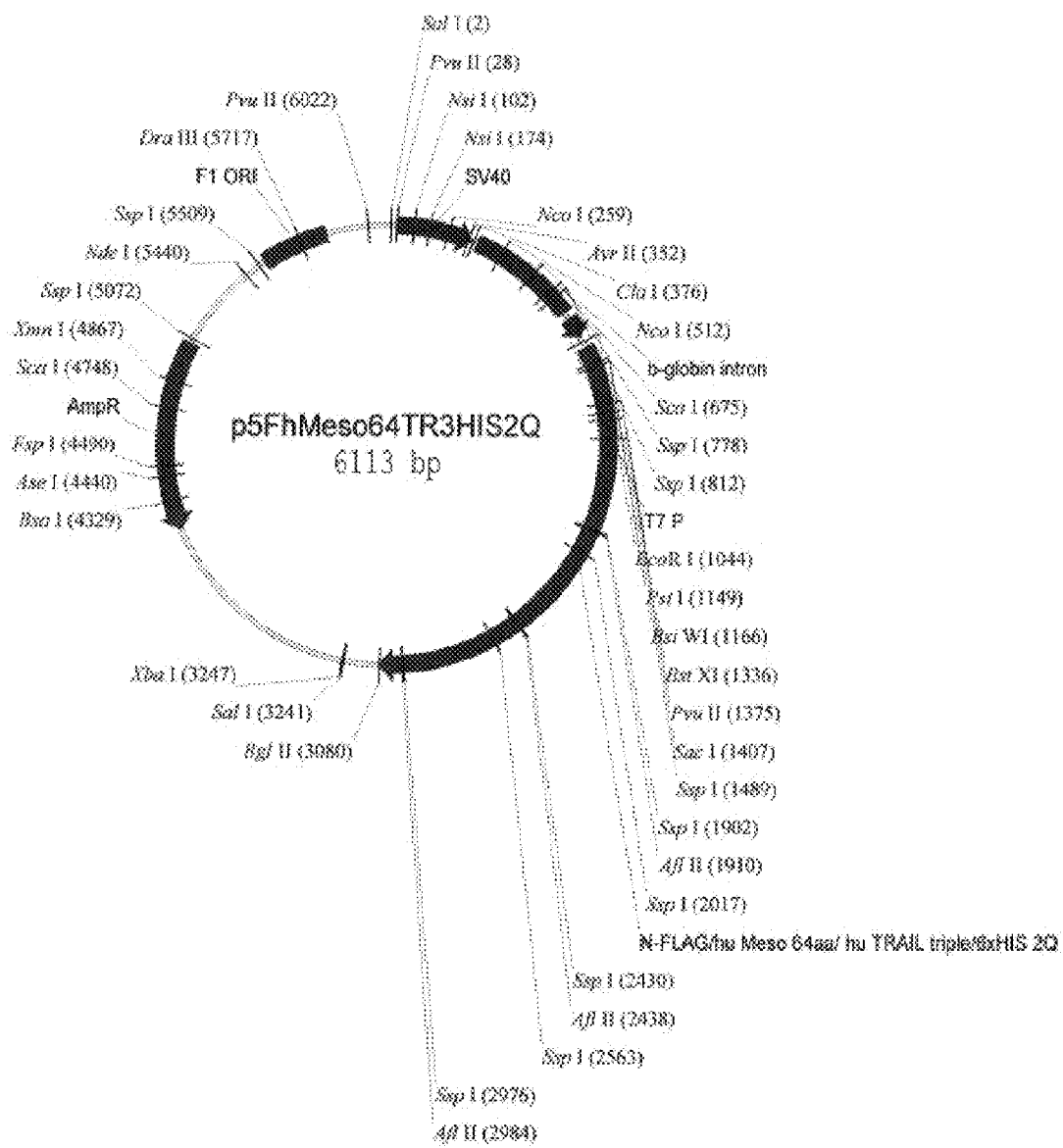
FIG. 11 illustrates a restriction map of plasmid p5FhMeso1TR3HIS2Q.

-continued p5FhMeso1TR3HIS2Q (6767 BP) (FIG. 11):

(SEQ ID NO: 3)

```
gtcgacttct gaggcggaaa gaaccagctg tggaatgtgt gtcagttagg gtgtggaaag    60
tccccaggct ccccagcagg cagaagtatg caaagcatgc atctcaatta gtcagcaacc   120
aggtgtggaa agtccccagg ctccccagca ggcagaagta tgcaaagcat gcatctcaat   180
tagtcagcaa ccatagtccc gcccctaact ccgcccatcc cgccctaac tccgcccagt   240
tccgcccatt ctccgcccca tggctgacta attttttta tttatgcaga ggccgaggcc   300
gcctcggcct ctgagctatt ccagaagtag tgaggaggct tttttggagg cctaggcttt   360
tgcaaaaagc tggatcgatc ctgagaactt cagggtgagt ttggggaccc ttgattgttc   420
tttcttttc gctattgtaa aattcatgtt atatggaggg ggcaaagttt tcagggtgtt   480
gtttagaatg ggaagatgtc ccttgtatca ccatggaccc tcatgataat tttgtttctt   540
tcactttcta ctctgitgac aaccattgtc tcctcttatt ttcttttcat tttctgtaac   600
tttttcgtta aactttagct tgcatttgta acgaattttt aaattcactt ttgtttattt   660
gtcagattgt aagtactttc tctaatcact tttttttcaa ggcaatcagg gtatattata   720
ttgtacttca gcacagtttt agagaacaat tgttataatt aaatgataag gtagaatatt   780
tctgcatata aattctggct ggcgtggaaa tattcttatt ggtagaaaca actacatcct   840
ggtcatcatc ctgcctttct ctttatggtt acaatgatat acactgtttg agatgaggat   900
aaaatactct gagtccaaac cgggcccctc tgctaaccat gttcatgcct tcttctttt    960
cctacagctc ctgggcaacg tgctggttat tgtgctgtct catcattttg caaagaatt   1020
gtaatacgac tcactatagg gcgaattcag gttctgtgga caatcacaat gggaatccaa   1080
ggagggtctg tcctgttcgg gctgctgctc gtcctggctg tcttctgcca ttcaggtcat   1140
agcctgcaga gctacaaccc tccgcgtacg gactacaagg acgatgatga caaacagatc   1200
agcggtggag gctcagaagt ggagaagaca gcctgtcctt caggcaagaa ggcccgcgag   1260
atagacgaga gcctcatctt ctacaagaag tgggagctgg aagcctgcgt ggatgcggcc   1320
ctgctggcca cccagatgga ccgcgtgaac gccatcccct tcacctacga gcagctggac   1380
gtcctaaagc ataaactgga tgagctctac ccacaaggtt accccgagtc tgtgatccag   1440
cacctgggct acctcttcct caagatgagc cctgaggaca ttcgcaagtg gaatgtgacg   1500
tccctggaga ccctgaaggc tttgcttgaa gtcaacaaag ggcacgaaat gagtcctcag   1560
gtggccaccc tgatcgaccg ctttgtgaag ggaagggggcc agctagacaa agacaccccta  1620
gacaccctga ccgccttcta ccctgggtac ctgtgctccc tcagcccga ggagctgagc   1680
tccgtgcccc ccagcagcat ctgggcggtc aggccccagg acctggacac gtgtgaccca   1740
aggcagctgg acgtcctcta tcccaaggcc cgccttgctt ccagaacat gaacgggtcc   1800
gaatacttcg tgaagatcca gtccttcctg ggtggggccc ccacggagga tttgaaggcg   1860
ctcagtcagc agaatgtgag catggacttg gccacgttca tgaagctgcg gacggatgcg   1920
gtgctgccgt tgactgtggc tgaggtgcag aaacttctgg accccacgt ggagggcctg   1980
aaggcggagg agcggcaccg cccggtgcgg gactggatcc tacggcagcg gcaggacgac  2040
ctggacacgc tgggctgggg gctacagggc ctgcgtacgc cacctatgat tttgagaacc  2100
tctgaggaaa ccatttctac agttcaagaa aagcaacaaa atatttctcc cctagtgaga  2160
gaaagaggtc ctcagagagt agcagctcac ataactggga ccagaggaag aagcaacaca  2220
ttgtcttctc caaactccaa gaatgaaaag gctctgggcc gcaaaataaa ctcctgggaa  2280
tcatcaagga gtgggcattc attcctgagc aacttgcact tgaggaatgg tgaactggtc  2340
atccatgaaa aagggttta ctacatctat tcccaaacat actttcgatt tcaggaggaa  2400
```

-continued

```
ataaaagaaa acacaaagaa cgacaaacaa atggtccaat atatttacaa atacacaagt  2460
tatcctgacc ctatattgtt gatgaaaagt gctagaaata gttgttggtc taaagatgca  2520
gaatatggac tctattccat ctatcaaggg ggaatatttg agcttaagga aaatgacaga  2580
attttttgttt ctgtaacaaa tgagcacttg atagacatgg accatgaagc cagttttttc  2640
ggggccttt tagttggcag atcccaaaat atttctcccc tagtgagaga aagaggtcct   2700
cagagagtag cagctcacat aactgggacc agaggaagaa gcaacacatt gtcttctcca   2760
aactccaaga atgaaaaggc tctgggccgc aaaataaact cctgggaatc atcaaggagt   2820
gggcattcat tcctgagcaa cttgcacttg aggaatggtg aactggtcat ccatgaaaaa   2880
gggttttact acatctattc ccaaacatac tttcgatttc aggaggaaat aaaagaaaac   2940
acaaagaacg acaaacaaat ggtccaatat atttacaaat acacaagtta tcctgaccct   3000
atattgttga tgaaaagtgc tagaaatagt tgttggtcta agatgcaga atatggactc    3060
tattccatct atcaaggggg aatatttgag cttaaggaaa atgacagaat ttttgtttct   3120
gtaacaaatg agcacttgat agacatggac catgaagcca gttttttcgg ggccttttta  3180
gttggcagat cccaccacca ccaccaccac caaaatattt ctcccctagt gagagaaaga   3240
ggtcctcaga gagtagcagc tcacataact gggaccagag gaagaagcaa cacattgtct   3300
tctccaaact ccaagaatga aaaggctctg ggccgcaaaa taaactcctg ggaatcatca   3360
aggagtgggc attcattcct gagcaacttg cacttgagga atggtgaact ggtcatccat   3420
gaaaagggt tttactacat ctattcccaa acatactttc gatttcagga ggaaataaaa    3480
gaaaacacaa agaacgacaa acaaatggtc caatatattt acaaatacac aagttatcct   3540
gaccctatat tgttgatgaa aagtgctaga aatagttgtt ggtctaaaga tgcagaatat   3600
ggactctatt ccatctatca aggggggaata tttgagctta aggaaaatga cagaattttt   3660
gtttctgtaa caaatgagca cttgatagac atggaccatg aagccagttt tttcggggcc   3720
tttttagttg gcagatctta atctaggatc ttattaaagc agaacttgtt tattgcagct   3780
tataatggtt acaaataaag caatagcatc acaaatttca caaataaagc atttttttca   3840
ctgcattcta gttgtggttt gtccaaactc atcaatgtat cttatcatgt ctggtcgact   3900
ctagactctt ccgcttcctc gctcactgac tcgctgcgct cggtcgttcg ctgcggcga    3960
gcggtatcag ctcactcaaa ggcggtaata cggttatcca cagaatcagg ggataacgca   4020
ggaaagaaca tgtgagcaaa aggccagcaa aaggccagga accgtaaaaa ggccgcgttg   4080
ctggcgtttt tccataggct ccgcccccct gacgagcatc acaaaaatcg acgctcaagt   4140
cagaggtggc gaaacccgac aggactataa agataccagg cgtttccccc tggaagctcc   4200
ctcgtgcgct ctcctgttcc gaccctgccg cttaccggat acctgtccgc ctttctccct   4260
tcgggaagcg tggcgctttc tcaatgctca cgctgtaggt atctcagttc ggtgtaggtc   4320
gttcgctcca agctgggctg tgtgcacgaa ccccccgttc agcccgaccg ctgcgcctta   4380
tccggtaact atcgtcttga gtccaacccg gtaagacacg acttatcgcc actggcagca   4440
gccactggta acaggattag cagagcgagg tatgtaggcg gtgctacaga gttcttgaag   4500
tggtggccta actacggcta cactagaagg acagtatttg gtatctgcgc tctgctgaag   4560
ccagttacct tcggaaaaag agttggtagc tcttgatccg gcaaacaaac caccgctggt   4620
agcggtggtt ttttgtttg caagcagcag attacgcgca gaaaaaaagg atctcaagaa   4680
gatcctttga tcttttctac ggggtctgac gctcagtgga acgaaaactc acgttaaggg   4740
attttggtca tgagattatc aaaaaggatc ttcacctaga tccttttaaa ttaaaaatga   4800
```

-continued

```
agttttaaat caatctaaag tatatatgag taaacttggt ctgacagtta ccaatgctta    4860
atcagtgagg cacctatctc agcgatctgt ctatttcgtt catccatagt tgcctgactc    4920
cccgtcgtgt agataactac gatacgggag ggcttaccat ctggcccag tgctgcaatg     4980 ataccgcgag acccacgctc accggctcca gatttatcag caataaacca gccagccgga    5040
agggccgagc gcagaagtgg tcctgcaact ttatccgcct ccatccagtc tattaattgt    5100
tgccgggaag ctagagtaag tagttcgcca gttaatagtt tgcgcaacgt tgttgccatt    5160
gctacaggca tcgtggtgtc acgctcgtcg tttggtatgg cttcattcag ctccggttcc    5220
caacgatcaa ggcgagttac atgatccccc atgttgtgca aaaagcggt tagctccttc     5280 ggtcctccga tcgttgtcag aagtaagttg gccgcagtgt tatcactcat ggttatggca    5340
gcactgcata attctcttac tgtcatgcca tccgtaagat gcttttctgt gactggtgag    5400
tactcaacca agtcattctg agaatagtgt atgcggcgac cgagttgctc ttgcccggcg    5460
tcaatacggg ataataccgc gccacatagc agaactttaa aagtgctcat cattggaaaa    5520
cgttcttcgg ggcgaaaact ctcaaggatc ttaccgctgt tgagatccag ttcgatgtaa    5580
cccactcgtg cacccaactg atcttcagca tcttttactt tcaccagcgt ttctgggtga    5640
gcaaaaacag gaaggcaaaa tgccgcaaaa aagggaataa gggcgacacg gaaatgttga    5700
atactcatac tcttcctttt tcaatattat tgaagcattt atcagggtta ttgtctcatg    5760
agcggataca tatttgaatg tatttagaaa aataaacaaa taggggttcc gcgcacattt    5820
ccccgaaaag tgccacctga cgtctaagaa accattatta tcatgacatt aacctataaa    5880
aataggcgta tcacgaggcc ctttcgtct cgcgcgtttc ggtgatgacg gtgaaaacct    5940
ctgacacatg cagctcccgg agacggtcac agcttgtctg taagcggatg ccgggagcag    6000
acaagcccgt cagggcgcgt cagcgggtgt tggcgggtgt cggggctggc ttaactatgc    6060
ggcatcagag cagattgtac tgagagtgca ccatatgcgg tgtgaaatac cgcacagatg    6120
cgtaaggaga aaataccgca tcaggaaatt gtaaacgtta atattttgtt aaaattcgcg    6180
ttaaattttt gttaaatcag ctcattttt aaccaatagg ccgaaatcgg caaaatccct    6240
tataaatcaa agaatagac cgagatagg ttgagtgttg ttccagtttg gaacaagagt      6300
ccactattaa agaacgtgga ctccaacgtc aaagggcgaa aaaccgtcta tcagggcgat    6360
ggcccactac gtgaaccatc accctaatca agttttttgg ggtcgaggtg ccgtaaagca    6420
ctaaatcgga acccctaaagg gagcccccga tttagagctt gacggggaaa gccggcgaac    6480
gtggcgagaa aggaagggaa gaaagcgaaa ggagcgggcg ctagggcgct ggcaagtgta    6540
gcggtcacgc tgcgcgtaac caccacaccc gccgcgctta atgcgccgct acagggcgcg    6600
tcgcgccatt cgccattcag gctacgcaac tgttgggaag ggcgatcggt gcgggcctct    6660
tcgctattac gccagctggc gaagggggga tgtgctgcaa ggcgattaag ttgggtaacg    6720
ccagggtttt cccagtcacg acgttgtaaa acgacggcca gtgaatt                 6767
p5TR3HIS2Q (5858 BP):
                                                            (SEQ ID NO: 4)
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc    120
aggtgtggaa agtccccagg ctccccagca ggcagaagta tgcaaagcat gcatctcaat    180
tagtcagcaa ccatagtccc gcccctaact ccgcccatcc cgcccctaac tccgcccagt    240
tccgcccatt ctccgcccca tggctgacta atttttttta tttatgcaga ggccgaggcc    300
gcctcggcct ctgagctatt ccagaagtag tgaggaggct tttttggagg cctaggcttt    360
tgcaaaaagc tggatcgatc ctgagaactt cagggtgagt ttggggaccc ttgattgttc    420
```

-continued

```
tttcttttc   gctattgtaa   aattcatgtt   atatggaggg   ggcaaagttt   tcagggtgtt    480
gtttagaatg   ggaagatgtc   ccttgtatca   ccatggaccc   tcatgataat   tttgtttctt    540
tcactttcta   ctctgttgac   aaccattgtc   tcctcttatt   ttcttttcat   tttctgtaac    600
tttttcgtta   aactttagct   tgcatttgta   acgaatttt   aaattcactt   ttgtttattt    660
gtcagattgt   aagtactttc   tctaatcact   tttttttcaa   ggcaatcagg   gtatattata    720
ttgtacttca   gcacagtttt   agagaacaat   tgttataatt   aaatgataag   gtagaatatt    780
tctgcatata   aattctggct   ggcgtggaaa   tattcttatt   ggtagaaaca   actacatcct    840
ggtcatcatc   ctgcctttct   ctttatggtt   acaatgatat   acactgtttg   agatgaggat    900
aaaatactct   gagtccaaac   cgggcccctc   tgctaaccat   gttcatgcct   tcttcttttt    960
cctacagctc   ctgggcaacg   tgctggttat   tgtgctgtct   catcattttg   gcaaagaatt   1020
gtaatacgac   tcactatagg   gcgaattcag   gttctgtgga   caatcacaat   gggaatccaa   1080
ggagggtctg   tcctgttcgg   gctgctgctc   gtcctggctg   tcttctgcca   ttcaggtcat   1140
agcctgcaga   gctacaaccc   tccgcgtacg   ccacctatga   ttttgagaac   ctctgaggaa   1200
accatttcta   cagttcaaga   aaagcaacaa   atatttctc   ccctagtgag   agaaagaggt   1260
cctcagagag   tagcagctca   cataactggg   accagaggaa   gaagcaacac   attgtcttct   1320
ccaaactcca   agaatgaaaa   ggctctgggc   cgcaaaataa   actcctggga   atcatcaagg   1380
agtgggcatt   cattcctgag   caacttgcac   ttgaggaatg   gtgaactggt   catccatgaa   1440
aaagggtttt   actacatcta   ttcccaaaca   tactttcgat   tcaggagga   aataaaagaa   1500 aacacaaaga   acgacaaaca   aatggtccaa   tatatttaca   aatacacaag   ttatcctgac   1560
cctatattgt   tgatgaaaag   tgctagaaat   agttgttggt   ctaaagatgc   agaatatgga   1620
ctctattcca   tctatcaagg   gggaatattt   gagcttaagg   aaaatgacag   aatttttgtt   1680
tctgtaacaa   atgagcactt   gatagacatg   gaccatgaag   ccagtttttt   cggggccttt   1740
ttagttggca   gatcccaaaa   tatttctccc   ctagtgagag   aaagaggtcc   tcagagagta   1800
gcagctcaca   taactgggac   cagaggaaga   agcaacacat   tgtcttctcc   aaactccaag   1860
aatgaaaagg   ctctgggccg   caaaataaac   tcctgggaat   catcaaggag   tgggcattca   1920
ttcctgagca   acttgcactt   gaggaatggt   gaactggtca   tccatgaaaa   agggttttac   1980
tacatctatt   cccaaacata   ctttcgattt   caggaggaaa   taaagaaaa   cacaagaac   2040 gacaaacaaa   tggtccaata   tatttacaaa   tacacaagtt   atcctgaccc   tatattgttg   2100
atgaaaagtg   ctagaaatag   ttgttggtct   aaagatgcag   aatatggact   ctattccatc   2160
tatcaagggg   gaatatttga   gcttaaggaa   atgacagaa   ttttttgttc   tgtaacaaat   2220
gagcacttga   tagacatgga   ccatgaagcc   agttttttcg   ggcctttt   agttggcaga   2280 tcccaccacc   accaccacca   ccaaaatatt   tctcccctag   tgagagaaag   aggtcctcag   2340
agagtagcag   ctcacataac   tgggaccaga   ggaagaagca   acacattgtc   ttctccaaac   2400
tccaagaatg   aaaaggctct   gggccgcaaa   ataaactcct   gggaatcatc   aaggagtggg   2460
cattcattcc   tgagcaactt   gcacttgagg   aatggtgaac   tggtcatcca   tgaaaaaggg   2520
ttttactaca   tctattccca   acatactttt   cgatttcagg   aggaaataaa   agaaacaca   2580 aagaacgaca   aacaaatggt   ccaatatatt   tacaaataca   caagttatcc   tgacccatata   2640 ttgttgatga   aaagtgctag   aaatagttgt   tggtctaaag   atgcagaata   tggactctat   2700
tccatctatc   aagggggaat   atttgagctt   aaggaaatg   acagaatttt   tgtttctgta   2760
acaaatgagc   acttgataga   catggaccat   gaagccagtt   ttttcggggc   tttttagtt   2820 ggcagatctt   aatctaggat   cttattaaag   cagaacttgt   ttattgcagc   ttataatggt   2880
```

-continued

```
tacaaataaa gcaatagcat cacaaatttc acaaataaag cattttttc actgcattct 2940 agttgtggtt tgtccaaact catcaatgta tcttatcatg tctggtcgac tctagactct 3000
tccgcttcct cgctcactga ctcgctgcgc tcggtcgttc ggctgcggcg agcggtatca 3060
gctcactcaa aggcggtaat acggttatcc acagaatcag gggataacgc aggaaagaac 3120
atgtgagcaa aaggccagca aaaggccagg aaccgtaaaa aggccgcgtt gctggcgttt 3180
ttccataggc tccgccccc tgacgagcat cacaaaaatc gacgctcaag tcagaggtgg 3240
cgaaacccga caggactata agataccag gcgtttcccc ctggaagctc cctcgtgcgc 3300
tctcctgttc cgaccctgcc gcttaccgga tacctgtccg cctttctccc ttcgggaagc 3360
gtggcgcttt ctcaatgctc acgctgtagg tatctcagtt cggtgtaggt cgttcgctcc 3420
aagctgggct gtgtgcacga accccccgtt cagcccgacc gctgcgcctt atccggtaac 3480
tatcgtcttg agtccaaccc ggtaagacac gacttatcgc cactggcagc agccactggt 3540
aacaggatta gcagagcgag gtatgtaggc ggtgctacag agttcttgaa gtggtggcct 3600
aactacggct acactagaag gacagtattt ggtatctgcg ctctgctgaa gccagttacc 3660
ttcggaaaaa gagttggtag ctcttgatcc ggcaaacaaa ccaccgctgg tagcggtggt 3720
ttttttgttt gcaagcagca gattacgcgc agaaaaaaag gatctcaaga agatcctttg 3780
atcttttcta cggggtctga cgctcagtgg aacgaaaact cacgttaagg gattttggtc 3840
atgagattat caaaaaggat cttcacctag atccttttaa attaaaaatg aagttttaaa 3900
tcaatctaaa gtatatatga gtaaacttgg tctgacagtt accaatgctt aatcagtgag 3960
gcacctatct cagcgatctg tctatttcgt tcatccatag ttgcctgact ccccgtcgtg 4020
tagataacta cgatacggga gggcttacca tctggcccca gtgctgcaat gataccgcga 4080
gacccacgct caccggctcc agatttatca gcaataaacc agccagccgg aagggccgag 4140
cgcagaagtg gtcctgcaac tttatccgcc tccatccagt ctattaattg ttgccgggaa 4200
gctagagtaa gtagttcgcc agttaatagt ttgcgcaacg ttgttgccat tgctacaggc 4260
atcgtggtgt cacgctcgtc gtttggtatg gcttcattca gctccggttc ccaacgatca 4320
aggcgagtta catgatcccc catgttgtgc aaaaaagcgg ttagctcctt cggtcctccg 4380
atcgttgtca gaagtaagtt ggccgcagtg ttatcactca tggttatggc agcactgcat 4440
aattctctta ctgtcatgcc atccgtaaga tgcttttctg tgactggtga gtactcaacc 4500
aagtcattct gagaatagtg tatgcggcga ccgagttgct cttgcccggc gtcaatacgg 4560
gataataccg cgccacatag cagaacttta aaagtgctca tcattggaaa acgttcttcg 4620
gggcgaaaac tctcaaggat cttaccgctg ttgagatcca gttcgatgta acccactcgt 4680
gcacccaact gatcttcagc atcttttact ttcaccagcg tttctgggtg agcaaaaaca 4740
ggaaggcaaa atgccgcaaa aaagggaata agggcgacac ggaaatgttg aatactcata 4800
ctcttccttt ttcaatatta ttgaagcatt tatcagggtt attgtctcat gagcggatac 4860
atatttgaat gtatttagaa aaataaacaa ataggggttc cgcgcacatt tccccgaaaa 4920
gtgccacctg acgtctaaga aaccattatt atcatgacat taacctataa aaataggcgt 4980
atcacgaggc ccctttcgtc tcgcgcgttt cggtgatgac ggtgaaaacc tctgacacat 5040
gcagctcccg gagacggtca cagcttgtct gtaagcggat gccgggagca gacaagcccg 5100
tcagggcgcg tcagcgggtg ttggcgggtg tcggggctgg cttaactatg cggcatcaga 5160
gcagattgta ctgagagtgc accatatgcg gtgtgaaata ccgcacagat gcgtaaggag 5220
aaaataccgc atcaggaaat tgtaaacgtt aatattttgt taaaattcgc gttaaatttt 5280
```

```
tgttaaatca gctcattttt taaccaatag gccgaaatcg gcaaaatccc ttataaatca 5340
aaagaataga ccgagatagg gttgagtgtt gttccagttt ggaacaagag tccactatta 5400
aagaacgtgg actccaacgt caaagggcga aaaaccgtct atcagggcga tggcccacta 5460
cgtgaaccat cacccctaatc aagtttttg gggtcgaggt gccgtaaagc actaaatcgg 5520
aaccctaaag ggagcccccg atttagagct tgacggggaa agccggcgaa cgtggcgaga 5580
aaggaaggga agaaagcgaa aggagcgggc gctagggcgc tggcaagtgt agcggtcacg 5640
ctgcgcgtaa ccaccacacc cgccgcgctt aatgcgccgc tacagggcgc gtcgcgccat 5700
tcgccattca ggctacgcaa ctgttgggaa gggcgatcgg tgcgggcctc ttcgctatta 5760
cgccagctgg cgaagggggg atgtgctgca aggcgattaa gttgggtaac gccagggttt 5820
tcccagtcac gacgttgtaa aacgacggcc agtgaatt             5858
```

Polypeptides with anti-tumor activity of the present teachings include, without limitation, polypeptides of the following sequences. His tags, when present, are indicated with bold typeface.

TR3
(SEQ ID NO: 5)
MGIQGGSVLFGLLLVLAVFCHSGHSLQSYNPPRTPPMILRTSEETISTVQEKQQNISPLVR
ERGPQRVAAHITGTRGRSNTLSSPNSKNEKALGRKINSWESSRSGHSFLSNLHLRNGELV
IHEKGFYYIYSQTYFRFQEEIKENTKNDKQMVQYIYKYTSYPDPILLMKSARNSCWSKD
AEYGLYSIYQGGIFELKENDRIFVSVTNEHLIDMDHEASFFGAFLVGRSQNISPLVRERGP
QRVAAHITGTRGRSNTLSSPNSKNEKALGRKINSWESSRSGHSFLSNLHLRNGELVIHEK
GFYYIYSQTYFRFQEEIKENTKNDKQMVQYIYKYTSYPDPILLMKSARNSCWSKDAEYG
LYSIYQGGIFELKENDRIFVSVTNEHLIDMDHEASFFGAFLVGRSQNISPLVRERGPQRVA
AHITGTRGRSNTLSSPNSKNEKALGRKINSWESSRSGHSFLSNLHLRNGELVIHEKGFYYI
YSQTYFRFQEEIKENTKNDKQMVQYIYKYTSYPDPILLMKSARNSCWSKDAEYGLYSIY
QGGIFELKENDRIFVSVTNEHLIDMDHEASFFGAFLVGRS

TR3-HIS
(SEQ ID NO: 6)
MGIQGGSVLFGLLLVLAVFCHSGHSLQSYNPPRTPPMILRTSEETISTVQEKQQNISPLVR
ERGPQRVAAHITGTRGRSNTLSSPNSKNEKALGRKINSWESSRSGHSFLSNLHLRNGELV
IHEKGFYYIYSQTYFRFQEEIKENTKNDKQMVQYIYKYTSYPDPILLMKSARNSCWSKD
AEYGLYSIYQGGIFELKENDRIFVSVTNEHLIDMDHEASFFGAFLVGRSQNISPLVRERGP
QRVAAHITGTRGRSNTLSSPNSKNEKALGRKINSWESSRSGHSFLSNLHLRNGELVIHEK
GFYYIYSQTYFRFQEEIKENTKNDKQMVQYIYKYTSYPDPILLMKSARNSCWSKDAEYG
LYSIYQGGIFELKENDRIFVSVTNEHLIDMDHEASFFGAFLVGRSQNISPLVRERGPQRVA
AHITGTRGRSNTLSSPNSKNEKALGRKINSWESSRSGHSFLSNLHLRNGELVIHEKGFYYI
YSQTYFRFQEEIKENTKNDKQMVQYIYKYTSYPDPILLMKSARNSCWSKDAEYGLYSIY
QGGIFELKENDRIFVSVTNEHLIDMDHEASFFGAFLVGGGGSHHHHHHRS

TR3-HIS2Q
(SEQ ID NO: 7)
MGIQGGSVLFGLLLVLAVFCHSGHSLQSYNPPRTPPMILRTSEETISTVQEKQQNISPLVR
ERGPQRVAAHITGTRGRSNTLSSPNSKNEKALGRKINSWESSRSGHSFLSNLHLRNGELV
IHEKGFYYIYSQTYFRFQEEIKENTKNDKQMVQYIYKYTSYPDPILLMKSARNSCWSKD
AEYGLYSIYQGGIFELKENDRIFVSVTNEHLIDMDHEASFFGAFLVGRSQNISPLVRERGP

-continued

QRVAAHITGTRGRSNTLSSPNSKNEKALGRKINSWESSRSGHSFLSNLHLRNGELVIHEK

GFYYIYSQTYFRFQEEIKENTKNDKQMVQYIYKYTSYPDPILLMKSARNSCWSKDAEYG

LYSIYQGGIFELKENDRIFVSVTNEHLIDMDHEASFFGAFLVGRSHHHHHHQNISPLVRE

RGPQRVAAHITGTRGRSNTLSSPNSKNEKALGRKINSWESSRSGHSFLSNLHLRNGELVI

HEKGFYYIYS QTYFRFQEEIKENTKNDKQMVQYIYKYTSYPDPILLMKSARNSCWSKDA

EYGLYSIYQGGIFELKENDRIFVSVTNEHLIDMDHEASFFGAFLVGRS

TR3-HIS2V
(SEQ ID NO: 8)
MGIQGGSVLFGLLLVLAVFCHSGHSLQSYNPPRTPPMILRTSEETISTVQEKQQNISPLVR

ERGPQRVAAHITGTRGRSNTLSSPNSKNEKALGRKINSWESSRSGHSFLSNLHLRNGELV

IHEKGFYYIYSQTYFRFQEEIKENTKNDKQMVQYIYKYTSYPDPILLMKSARNSCWSKD

AEYGLYSIYQGGIFELKENDRIFVSVTNEHLIDMDHEASFFGAFLVGRSQNISPLVRERGP

QRVAAHITGTRGRSNTLSSPNSKNEKALGRKINSWESSRSGHSFLSNLHLRNGELVIHEK

GFYYIYSQTYFRFQEEIKENTKNDKQMVQYIYKYTSYPDPILLMKSARNSCWSKDAEYG

LYSIYQGGIFELKENDRIFVSVTNEHLIDMDHEASFFGAFLVGRSHHHHHHVRERGPQR

VAAHITGTRGRSNTLSSPNSKNEKALGRKINSWESSRSGHSFLSNLHLRNGELVIHEKGF

YYIYSQTYFRFQEEIKENTKNDKQMVQYIYKYTSYPDPILLMKSARNSCWSKDAEYGLY

SIYQGGIFELKENDRIFVSVTNEHLIDMDHEASFFGAFLVGRS

Meso-TR3
(SEQ ID NO: 9)
MGIQGGSVLFGLLLVLAVFCHSGHSLQSYNPPRTDYKDDDDKQISGGGSEVEKTACPSG

KKAREIDESLIFYKKWELEACVDAALLATQMDRVNAIPFTYEQLDVLKHKLDELYPQG

YPESVIQHLGYLFLKMSPEDIRKWNVTSLETLKALLEVNKGHEMSPQVATLIDRFVKGR

GQLDKDTLDTLTAFYPGYLCSLSPEELSSVPPSSIWAVRPQDLDTCDPRQLDVLYPKARL

AFQNMNGSEYFVKIQSFLGGAPTEDLKALSQQNVSMDLATFMKLRTDAVLPLTVAEVQ

KLLGPHVEGLKAEERHRPVRDWILRQRQDDLDTLGLGLQGLRTPPMILRTSEETISTVQE

KQQNISPLVRERGPQRVAAHITGTRGRSNTLSSPNSKNEKALGRKINSWESSRSGHSFLS

NLHLRNGELVIHEKGFYYIYSQTYFRFQEEIKENTKNDKQMVQYIYKYTSYPDPILLMKS

ARNSCWSKDAEYGLYSIYQGGIFELKENDRIFVSVTNEHLIDMDHEASFFGAFLVGRSQ

NISPLVRERGPQRVAAHITGTRGRSNTLSSPNSKNEKALGRKINSWESSRSGHSFLSNLHL

RNGELVIHEKGFYYIYSQTYFRFQEEIKENTKNDKQMVQYIYKYTSYPDPILLMKSARNS

CWSKDAEYGLYSIYQGGIFELKENDRIFVSVTNEHLIDMDHEASFFGAFLVGRSQNISPL

VRERGPQRVAAHITGTRGRSNTLSSPNSKNEKALGRKINSWESSRSGHSFLSNLHLRNGE

LVIHEKGFYYIYSQTYFRFQEEIKENTKNDKQMVQYIYKYTSYPDPILLMKSARNSCWS

KDAEYGLYSIYQGGIFELKENDRIFVSVTNEHLIDMDHEASFFGAFLVGRS

Meso-TR3HIS2Q
(SEQ ID NO: 10)
MGIQGGSVLFGLLLVLAVFCHSGHSLQSYNPPRTDYKDDDDKQISGGGSEVEKTACPSG

KKAREIDESLIFYKKWELEACVDAALLATQMDRVNAIPFTYEQLDVLKHKLDELYPQG

YPESVIQHLGYLFLKMSPEDIRKWNVTSLETLKALLEVNKGHEMSPQVATLIDRFVKGR

GQLDKDTLDTLTAFYPGYLCSLSPEELSSVPPSSIWAVRPQDLDTCDPRQLDVLYPKARL

AFQNMNGSEYFVKIQSFLGGAPTEDLKALSQQNVSMDLATFMKLRTDAVLPLTVAEVQ

KLLGPHVEGLKAEERHRPVRDWILRQRQDDLDTLGLGLQGLRTPPMILRTSEETISTVQE

-continued

```
KQQNISPLVRERGPQRVAAHITGTRGRSNTLSSPNSKNEKALGRKINSWESSRSGHSFLS

NLHLRNGELVIHEKGFYYIYSQTYFRFQEEIKENTKNDKQMVQYIYKYTSYPDPILLMKS

ARNSCWSKDAEYGLYSIYQGGIFELKENDRIFVSVTNEHLIDMDHEASFFGAFLVGRSQ

NISPLVRERGPQRVAAHITGTRGRSNTLSSPNSKNEKALGRKINSWESSRSGHSFLSNLHL

RNGELVIHEKGFYYIYSQTYFRFQEEIKENTKNDKQMVQYIYKYTSYPDPILLMKSARNS

CWSKDAEYGLYSIYQGGIFELKENDRIFVSVTNEHLIDMDHEASFFGAFLVGRSHHHHH

HQNISPLVRERGPQRVAAHITGTRGRSNTLSSPNSKNEKALGRKINSWESSRSGHSFLSN

LHLRNGELVIHEKGFYYIYSQTYFRFQEEIKENTKNDKQMVQYIYKYTSYPDPILLMKSA

RNSCWSKDAEYGLYSIYQGGIFELKENDRIFVSVTNEHLIDMDHEASFFGAFLVGRS

Meso64-TR3
                                                      (SEQ ID NO: 11)
MGIQGGSVLFGLLLVLAVFCHSGHSLQSYNPPRTDYKDDDDKQISGGGSEVEKTACPSG

KKAREIDESLIFYKKWELEACVDAALLATQMDRVNAIPFTYEQLDVLKHKLDELGGGS

GTPPMILRTSEETISTVQEKQQNISPLVRERGPQRVAAHITGTRGRSNTLSSPNSKNEKAL

GRKINSWESSRSGHSFLSNLHLRNGELVIHEKGFYYIYSQTYFRFQEEIKENTKNDKQMV

QYIYKYTSYPDPILLMKSARNSCWSKDAEYGLYSIYQGGIFELKENDRIFVSVTNEHLID

MDHEASFFGAFLVGRSQNISPLVRERGPQRVAAHITGTRGRSNTLSSPNSKNEKALGRKI

NSWESSRSGHSFLSNLHLRNGELVIHEKGFYYIYSQTYFRFQEEIKENTKNDKQMVQYIY

KYTSYPDPILLMKSARNSCWSKDAEYGLYSIYQGGIFELKENDRIFVSVTNEHLIDMDHE

ASFFGAFLVGRSQNISPLVRERGPQRVAAHITGTRGRSNTLSSPNSKNEKALGRKINSWE

SSRSGHSFLSNLHLRNGELVIHEKGFYYIYSQTYFRFQEEIKENTKNDKQMVQYIYKYTS

YPDPILLMKSARNSCWSKDAEYGLYSIYQGGIFELKENDRIFVSVTNEHLIDMDHEASFF

GAFLVGRS

Meso64-TR3HIS2Q
                                                      (SEQ ID NO: 12)
MGIQGGSVLFGLLLVLAVFCHSGHSLQSYNPPRTDYKDDDDKQISGGGSEVEKTACPSG

KKAREIDESLIFYKKWELEACVDAALLATQMDRVNAIPFTYEQLDVLKHKLDELGGGS

GTPPMILRTSEETISTVQEKQQNISPLVRERGPQRVAAHITGTRGRSNTLSSPNSKNEKAL

GRKINSWESSRSGHSFLSNLHLRNGELVIHEKGFYYIYSQTYFRFQEEIKENTKNDKQMV

QYIYKYTSYPDPILLMKSARNSCWSKDAEYGLYSIYQGGIFELKENDRIFVSVTNEHLID

MDHEASFFGAFLVGRSQNISPLVRERGPQRVAAHITGTRGRSNTLSSPNSKNEKALGRKI

NSWESSRSGHSFLSNLHLRNGELVIHEKGFYYIYSQTYFRFQEEIKENTKNDKQMVQYIY

KYTSYPDPILLMKSARNSCWSKDAEYGLYSIYQGGIFELKENDRIFVSVTNEHLIDMDHE

ASFFGAFLVGRSHHHHHHQNISPLVRERGPQRVAAHITGTRGRSNTLSSPNSKNEKALG

RKINSWESSRSGHSFLSNLHLRNGELVIHEKGFYYIYSQTYFRFQEEIKENTKNDKQMVQ

YIYKYTSYPDPILLMKSARNSCWSKDAEYGLYSIYQGGIFELKENDRIFVSVTNEHLIDM

DHEASFFGAFLVGRS
```

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

Figure 2:
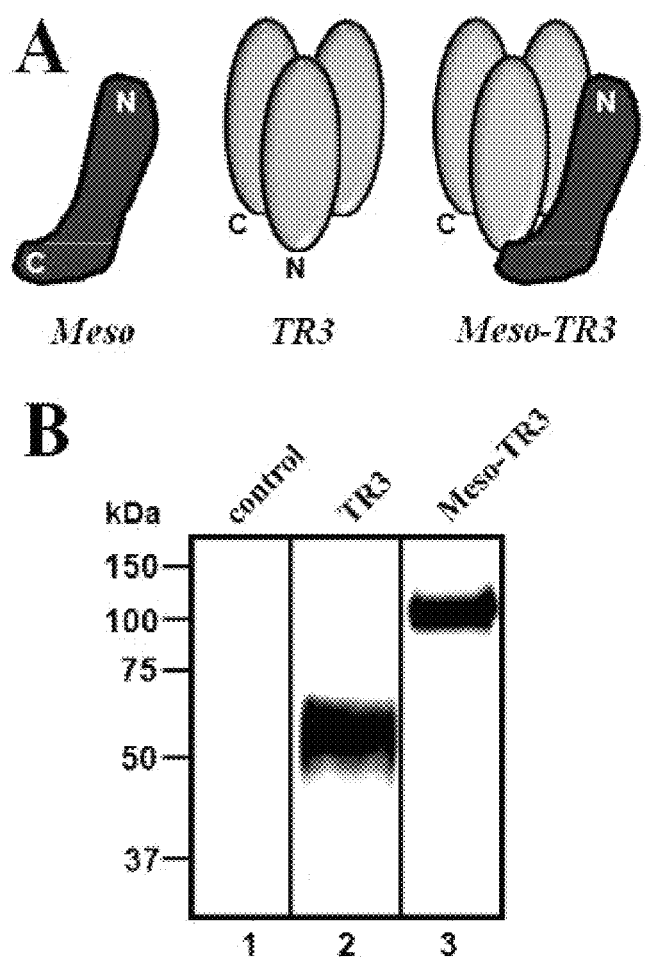
FIG. 2A-B illustrates design and biochemical characterization of MUC16-targeted TRAIL.

This example illustrates design and biochemical characterization of the MUC16-targeted TRAIL trimer TR3 (FIG. 2). FIG. 2A is a schematic representation of proteins developed by the inventors. In these experiments, soluble mesothelin (Meso) containing an N-terminal FLAG tag (not shown), the parental TRAIL drug platform TR3 (center) and the MUC16-targeted mesothelin-TR3 fusion protein (Meso-TR3) were produced by transient transfection of HEK293T cells. FIG. 2B, depicts a Western blot analysis (reducing conditions) documents the molecular weights of TR3 (≈61 kDa, lane 2) and Meso-TR3 (≈100 kDa, lane 3) using anti-TRAIL pAb. Supernatant from mock-transfected HEK293T cells served as a negative control (lane 1).

Soluble mesothelin has been shown to bind to MUC16 rapidly and with high affinity (Gubbels, J. A., et al., Mol. Cancer 5:50, 2006). Since endogenous mesothelin is attached to the cell surface via a GPI anchor (Hassan, R., et al., Clin. Cancer Res. 10:3937, 2004; Chang, K., et al., Proc. Natl. Acad. Sci. U.S.A. 93:136, 1996), we designed a secreted form of the glycoprotein by deleting its GPI signal sequence (FIG. 2A, Meso). For immunologic detection purposes, we included a FLAG epitope tag, located at the amino-terminus of the secreted protein (not shown). The recombinant protein was produced in HEK293T cells and Western blot analysis confirmed its identity with a molecular weight of ≈40 kDa (not shown). To convert TR3 (FIG. 2A, center) into a MUC16-targeted cancer drug, we inserted the entire cDNA of soluble mesothelin (including the N-terminal FLAG tag) to the 5'-terminus of a TR3 expression plasmid (FIG. 2A, Meso-TR3). The resulting genetic constructs were expressed in mammalian 293T cells and characterized by Western blot analysis. Meso-TR3 was identified as a fusion protein with an apparent molecular weight of ≈100 kDa with the parental molecule TR3 being ≈40 kDa smaller (FIG. 2B), consistent with the molecular weight of the mature and soluble form of human mesothelin.

Example 2

Figure 3:
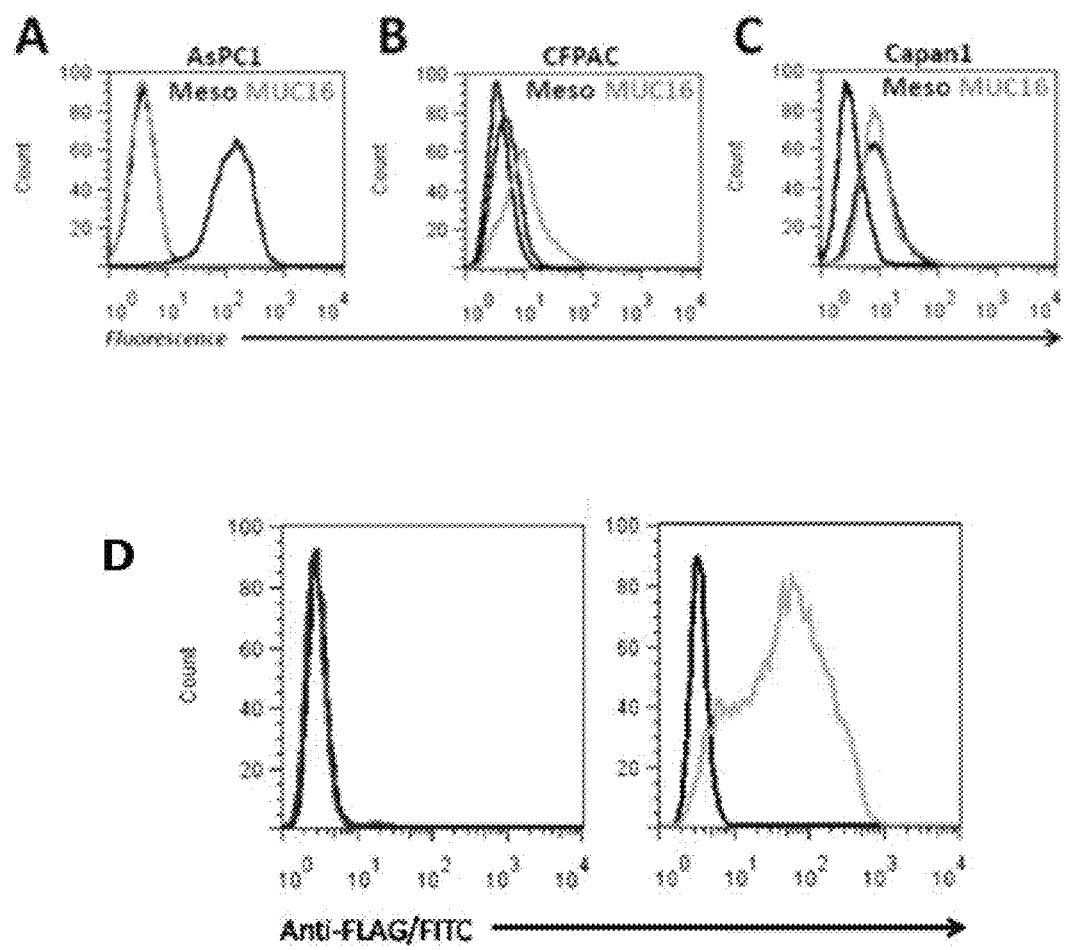
FIG. 3A-D illustrates expression levels of mesothelin and MUC16 in pancreatic cancer cell lines (A, B, C) and mesothelin binding to MUC16-expressing target cells (D).

This example illustrates that mesothelin binds to MUC16 in MUC16-expressing cells. In these experiments, various cancer cell lines were screened for expression of mesothelin and MUC16. Briefly, cancer cell lines were incubated with antibodies against human mesothelin (K1, Santa Cruz) and human MUC16 (X75, AbCam). Primary antibody was detected with fluorescently labeled secondary antibody. The cells were then analyzed by flow cytometry. Mesothelin was expressed in all pancreatic cancer cell lines screened (AsPC1, CFPAC, Capan1) as well as ovarian cell line OVCAR3 (FIG. 3A-C, FIG. 4 A-C). MUC16 was only absent in AsPC3 (FIG. 3A). The presence of surface bound MUC16 is a prerequisite for the targeted delivery of TR3 to the cancer cells.

In order to confirm the MUC16 expression profile on OVCAR3 cells, we performed flow cytometry and were able to detect a strong surface expression with a homogenous staining pattern for 100% of the cells (FIG. 4A). Next, we tested the ability of soluble, FLAG-tagged mesothelin to bind to membrane-bound MUC16 employing an in vitro binding assay using the same OVCAR3 cell line. Indeed, flow cytometry confirmed that soluble mesothelin was capable of binding to OVCAR3 cells (FIG. 4B). The staining pattern correlated well with the MUC16 expression profile of this cell line as nearly 100% of the cells were positive for the FLAG epitope tag, i.e. bound recombinant mesothelin. This pilot experiment was crucial as it confirmed not only the binding of recombinant mesothelin to native MUC16 on the target cells but also demonstrated accessibility of the epitope tag in the context of the mesothelin/MUC16 interaction.

In a next step, we asked if mesothelin protein, as part of the Meso-TR3 fusion protein, was capable of interacting with MUC16 on the OVCAR3 cell surface to facilitate membrane tethering of TR3. It was predicted that the multi-domain Meso-TR3 fusion protein could bind to OVCAR3 cells via two discrete mechanisms: 1) via the mesothelin/MUC16 interaction and 2) via the TR3/death receptor interaction [both DR4 and DR5 are expressed in OVCAR3 cells, not shown and Reis, C. R., et al., Cell Death. Dis. 1:e83, 2010]. Since these circumstances would have complicated the interpretation of binding studies mediated exclusively via mesothelin, we first saturated the death receptor binding sites of Meso-TR3 with soluble death receptor 5 (DR5-Fc). In a following step, the Meso-TR3/DR5-Fc complexes were added to OVCAR3 cells in suspension. After several washing steps, the cells were stained for the presence of the FLAG epitope tag as evidence for drug binding to the OVCAR3 reporter cells. Using flow cytometry, we detected a strong and homogeneous fluorescence signal for cell-bound Meso-TR3, which was again nearly identical to the MUC16 staining profile and similar to the binding pattern of soluble mesothelin alone (FIG. 4C).

Further proof that Meso-TR3 and MUC16 do in fact co-localize on the plasma membrane of the target cells was obtained by employing confocal microscopy. Using the same detection system (anti-FLAG antibody) and death receptor blocking strategy (DR5-Fc pretreatment) as described above, the cells were now treated in an adherent state prior to washing, fixation, and immunostaining. Strong fluorescence signals were obtained for both the MUC16 eptiope (red) and the FLAG tag of Meso-TR3 (green) (FIG. 4D). Importantly, the two signals overlapped (FIG. 4D, "merge"), suggesting that Meso-TR3 co-localizes with the mesothelin receptor MUC16 on the cancer cell membrane.

Figure 4:
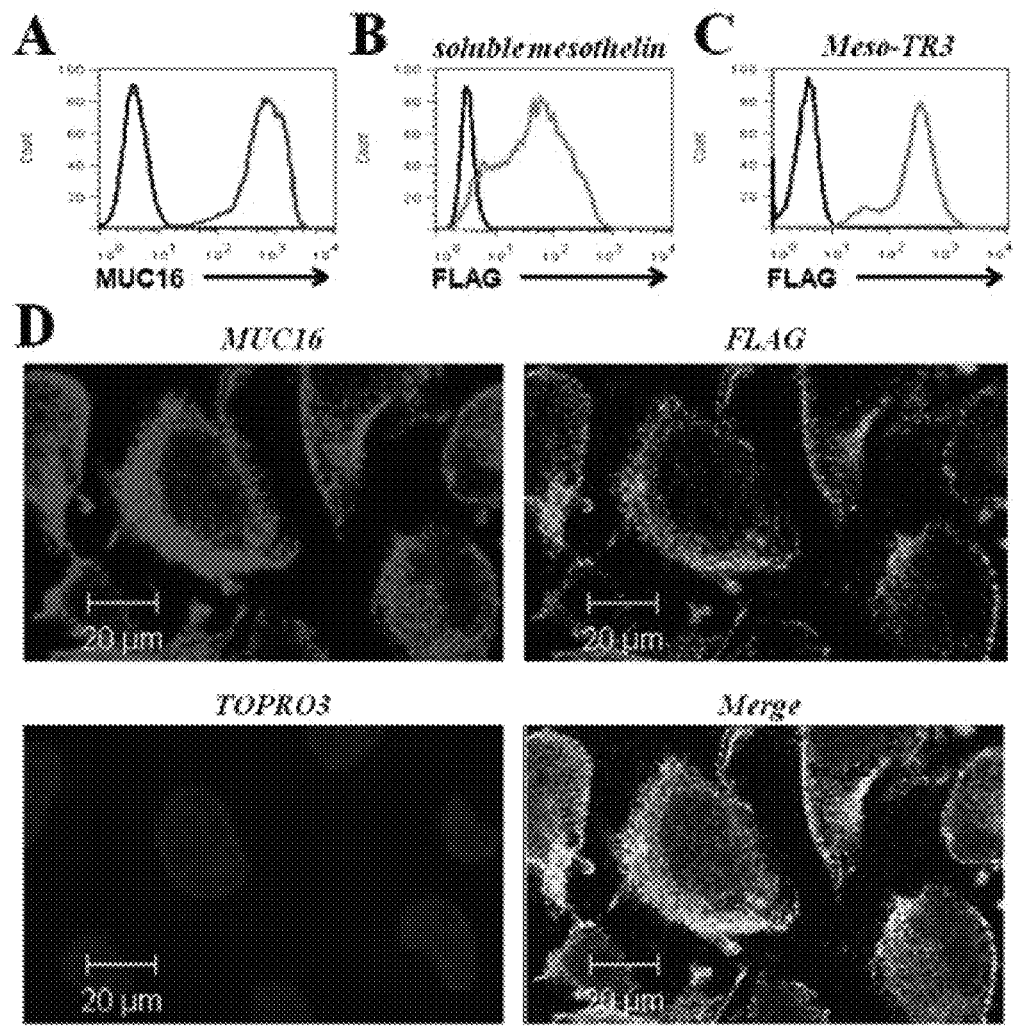
FIG. 4A-D illustrates Meso-TR3 binding to MUC16-expressing cancer targets.

To demonstrate the targeting of mesothelin to cell surface MUC16, soluble FLAG-tagged mesothelin was generated in HEK293T cells. OVCAR3 cells were incubated with supernatant from HEK293T cells transfected with a secreted, FLAG-tagged form of human mesothelin. Following extensive washing to prevent detection of non-specific binding, mesothelin binding to MUC16 was assessed by staining for the FLAG tag. The cells were then analyzed by flow cytometry. There was a strong signal increase on the MUC16-positive OVCAR3 cancer cells, verifying that soluble mesothelin has a strong binding affinity for native MUC16 (FIG. 3D). In FIG. 4, A presents a FACS-analysis of OVCAR3 cells assessed for expression of MUC16 (mAb X75) and a PE-conjugated secondary Ab (red line). The secondary Ab alone served to establish the background fluorescence (black line). In experiments illustrated in B, OVCAR3 cells in suspension were incubated with HEK293T-derived culture supernatant containing soluble mesothelin. Mesothelin binding was detected via anti-FLAG antibody staining (mAb M2) and a FITC-conjugated secondary Ab (green line). Cells treated with culture medium alone served as negative control (black line). In experiments illustrated in C, OVCAR3 cells in suspension were incubated with HEK293T-derived culture supernatant containing Meso-TR3.

To prevent binding of Meso-TR3 via TR3/death receptor interaction, Meso-TR3 was complexed with soluble DR5-Fc. Meso-TR3 binding was detected via anti-FLAG antibody staining similar to (B) using mAb M2, followed by FITC-conjugated secondary Ab (green line). Cells treated with culture medium alone served as negative control (black line). D, OVCAR3 cells were grown on 4-chamber slides and incubated the following day with Meso-TR3 complexed with DR5-Fc, similar to what has been described for (C). After washing, the cells were stained with a mixture of MUC16 pAb (red) and FLAG mAb (green), respectively. The cells were counterstained with TOPRO3 (blue, nuclei) and analyzed by confocal microscopy. The individual channels were overlaid to document co-localization of tumor marker and the targeted cancer drug (Merge). Original magnification: 63×.

Example 3

This example illustrates functional consequences of attaching the MUC16 targeting domain (mesothelin) to TR3.

TR3 and the fusion polypeptide mesothelin-TR3 (FIG. 1) were produced in HEK293T cells using standard transfection procedures. When MUC16-deficient Jurkat cells were treated with equimolar concentrations of TR3 and mesothelin-TR3, the cells were killed to the same degree (FIG. 5A).

Figure 5:
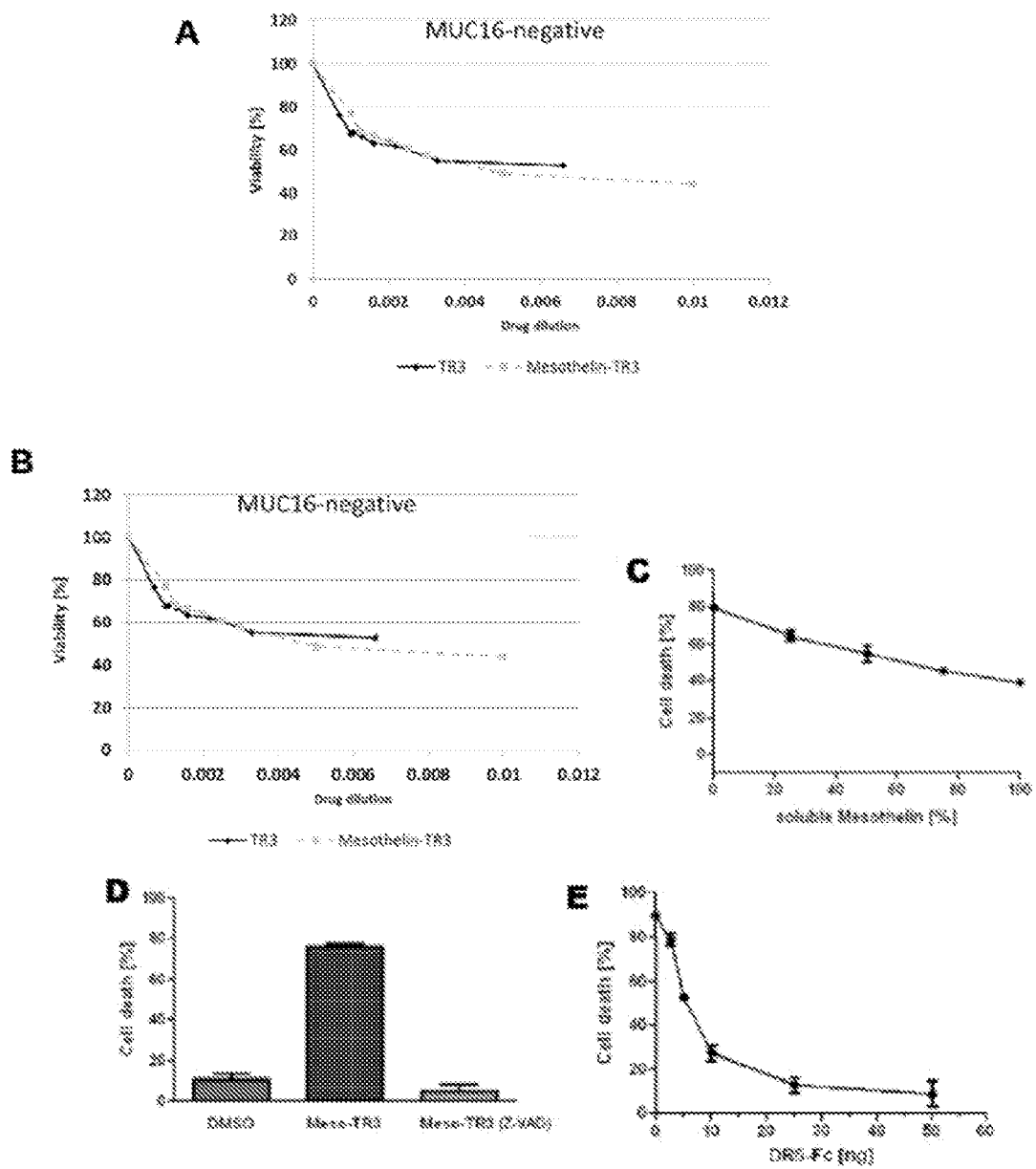
FIG. 5A-E illustrates cell killing of MUC16-positive cells by a mesothelin-TR3 fusion polypeptide.

In contrast, as shown in FIG. 5, when MUC16-high expressing OVCAR3 cells were treated with equimolar concentrations of TR3 and mesothelin-TR3, the mesothelin-TR3 was substantially more powerful in killing the cells than TR3 alone (5B).

OVCAR3 cells treated with mesothelin-TR3 can be rescued from cell death by adding increasing amounts of soluble mesothelin (5C). To determine whether cell death is caused by apoptosis, OVCAR3 cells were treated with mesothelin-TR3 in the presence of Z-VAD, a cell-permanent pan caspase inhibitor that inhibits the induction of apoptosis. In the presence of mesothelin-TR3, OVCAR3 cells were killed. However, with the addition of Z-VAD OVCAR3, cell death was minimal (5D).

To determine if the targeting of TR3 to the cell surface via mesothelin involves the native TR3 death pathway, OVCAR3 cells were treated with mesothelin-TR3 in the presence of increasing amounts of anti death receptor 5 (anti-DR5) antibody. Increasing amounts of anti-DR5 antibody inhibited the cancer cell killing by mesothelin-TR3, suggesting that the targeting of TR3 through mesothelin causes cell death via the native TR3 death pathway (5E).

Example 4

Figure 6:
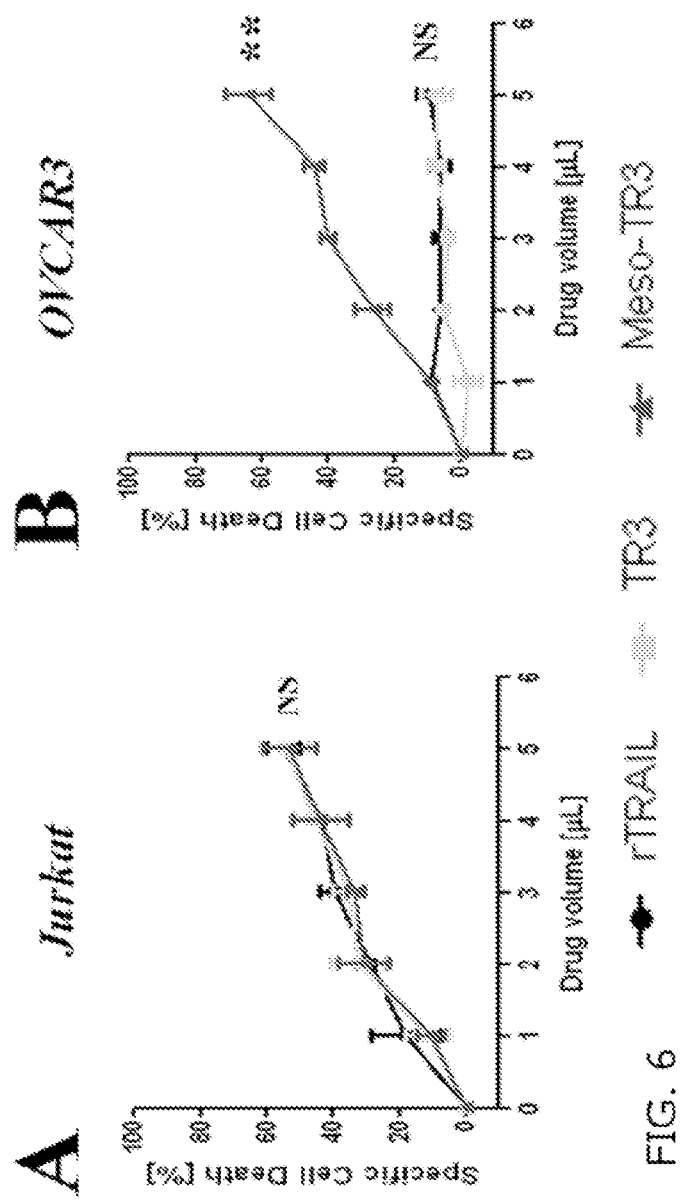
FIG. 6A-B illustrates that Meso-TR3 is a targeted therapeutic on MUC16-expressing tumor cells.

This example illustrates that mesothelin-TR3 is a targeted therapeutic on MUC16-expressing tumor cells, and that the mesothelin/MUC16 interaction can convert Meso-TR3 into a potent cancer drug (FIG. 6).

In order to compare the relative ability of cell death induction between Meso-TR3 and non-targeted TR3, it was important to establish the killing capacity of each drug mediated exclusively by the TR3 effector domain. Thus, we chose the TRAIL-sensitive T leukemia cell line Jurkat which lacks expression of MUC16 (not shown). We established the killing curves for both TR3 drugs and included recombinant TRAIL (rTRAIL) as an internal reference. At the drug concentrations chosen, all TRAIL drugs induced cell death to the same degree in the absence of the tumor marker MUC16 (FIG. 6A). This killing profile changed significantly when the same drug concentrations were used to treat MUC16-positive OVCAR3 cells, known to be sensitive to recombinant TRAIL (Lane, D., et al., Gynecol. Oncol. 93:594, 2004; Lane, D., et al., Mol. Cancer Ther. 5:509, 2006; Reis, C. R., et al., Cell Death. Dis. 1:e83, 2010). Non-targeted TR3 turned out to be quite inefficient with only ≈10% cell killing capacity at the highest dose used (FIG. 6B). Importantly, TR3's killing profile was identical to that of rTRAIL, which is consistent with our earlier findings in that both drugs activate the extrinsic death pathway equally well and suggests that each trimer assumes the same native conformation (Spitzer, D., et al., Mol. Cancer Ther. 9:2142, 2010). Treatment with Meso-TR3, however, resulted in a much enhanced killing profile approaching 65% cell death at the highest drug dose employed (FIG. 6B). Linear regression analysis suggested a 7 to 12-fold stronger activity profile of Meso-TR3 when compared to TR3 and rTRAIL in OVCAR3 cells.

FIG. 6 shows the following: A, The cell killing profiles of TR3, Meso-TR3 and rTRAIL [0.2 ng/µL] were established on the MUC16-deficient T cell leukemia cell line Jurkat. NS, not significant (ANOVA). B, The same killing assay as in (A) using identical drug concentrations but the MUC16-positive ovarian cancer cell line OVCAR3 instead. **, P<0.006; NS, not significant (ANOVA).

Example 5

Figure 7:
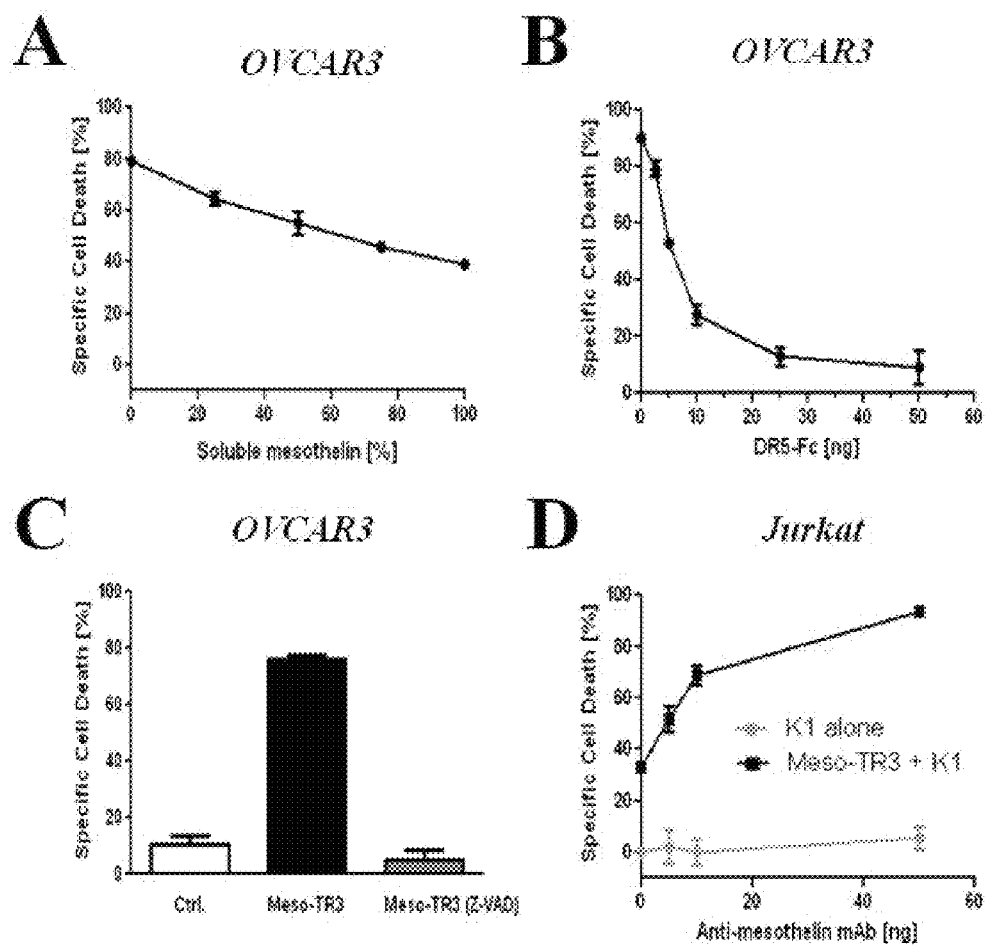
FIG. 7A-D illustrates phenotypic characterization of MUC16-targeted Meso-TR3.

This example illustrates that Meso-TR3 is phenotypically identical to conventional TRAIL (FIG. 7).

Based on the much enhanced killing profile of Meso-TR3 on MUC16-positive OVCAR3 cells, we hypothesized that the mesothelin/MUC16 interaction, i.e. the surface tethering of Meso-TR3 was responsible for the observed effects. To investigate this assumption, we performed a killing assay in the presence of increasing concentrations of soluble mesothelin to block the MUC16/Meso-TR3 interaction. As predicted, we were able to achieve a dose-dependent reduction in cell killing from 80% (no competitor) to 40% (highest competitor dose) (FIG. 7A). We did not expect 100% rescue of the cells from apoptosis, because TR3 alone as well as recombinant rTRAIL exhibit baseline apoptosis-inducing activities in OVCAR3 cells, consistent with our observations.

In order to rule out phenotypic changes that might have been created following addition of the MUC16 targeting moiety mesothelin to the TR3 drug platform, we asked if the induction of cell death was purely mediated via the extrinsic death receptor pathway. Two lines of evidence suggest that this mechanism is well preserved following Meso-TR3 treatment. First, when soluble DR5-Fc was added to a standard killing assay using MUC16-positive OVCAR3 cells, Meso-TR3's killing capacity was nearly completely blunted, evidenced by a gradual decrease in cell death in a dose-dependent fashion from 90% in the absence of the soluble receptor to below 10% at the highest DR5-Fc concentration (FIG. 7B). As additional evidence for the involvement of the death receptor signaling cascade induced by Meso-TR3, the pan-caspase inhibitor Z-VAD-FMK blocked intracellular caspase activities and protected the cells completely from apoptosis (FIG. 7C).

Higher order TRAIL aggregates have been associated with increased activity due to more efficient death receptor clustering, especially regarding DR5 (Schneider, P., et al., J. Exp. Med. 187:1205, 1998). In an attempt to recapitulate these observations, we treated Jurkat cells with Meso-TR3 in the presence of a mAb directed against the mesothelin moiety of the MUC16-targeted fusion protein. Using a sublethal dose of Meso-TR3 (33% cell death), we were able to demonstrate a dose-dependent augmentation of cell death to nearly 100% at the highest concentration of cross-linking antibody (FIG. 7D). These results strongly suggest that Meso-TR3 assumes a monomeric configuration in solution that can be further functionally enhanced by forming higher order aggregates (dimers), a concept just recently being utilized to treat highly vascularized cancers (Wilson, N. S., et al., Cancer Cell 22:80, 2012).

In FIG. 7, A, OVCAR3 cells were challenged with a constant amount of Meso-TR3 (80% specific cell death) and increasing concentrations of soluble mesothelin to study the impact of the mesothelin/MUC16 interaction of Meso-TR3. B, OVCAR3 cells were challenged with a constant amount of Meso-TR3 (90% specific cell death) and increasing concentrations of DR5-Fc to verify involvement of the extrinsic death pathway as a mechanism of Meso-TR3 killing. C, OVCAR3 cells were treated with a constant amount of Meso-TR3 (75% specific cell death) in the presence of Z-VAD-FMK, a pan-caspase inhibitor to block the extrinsic death pathway. Cells treated with DMSO were used as a control. D, MUC16-deficient Jurkat cells were treated with low dose Meso-TR3 (33% specific cell death) in the presence of anti-mesothelin mAb. Cross-linking of Meso-TR3 enhances target cell death to nearly 100%. Cells treated with anti-mesothelin Ab alone served as a control. Cells treated with medium alone were used as control. Error bars, ±SD. Results are representatives of at least 2 independent experiments done in triplicates.

Example 6

Figure 8:
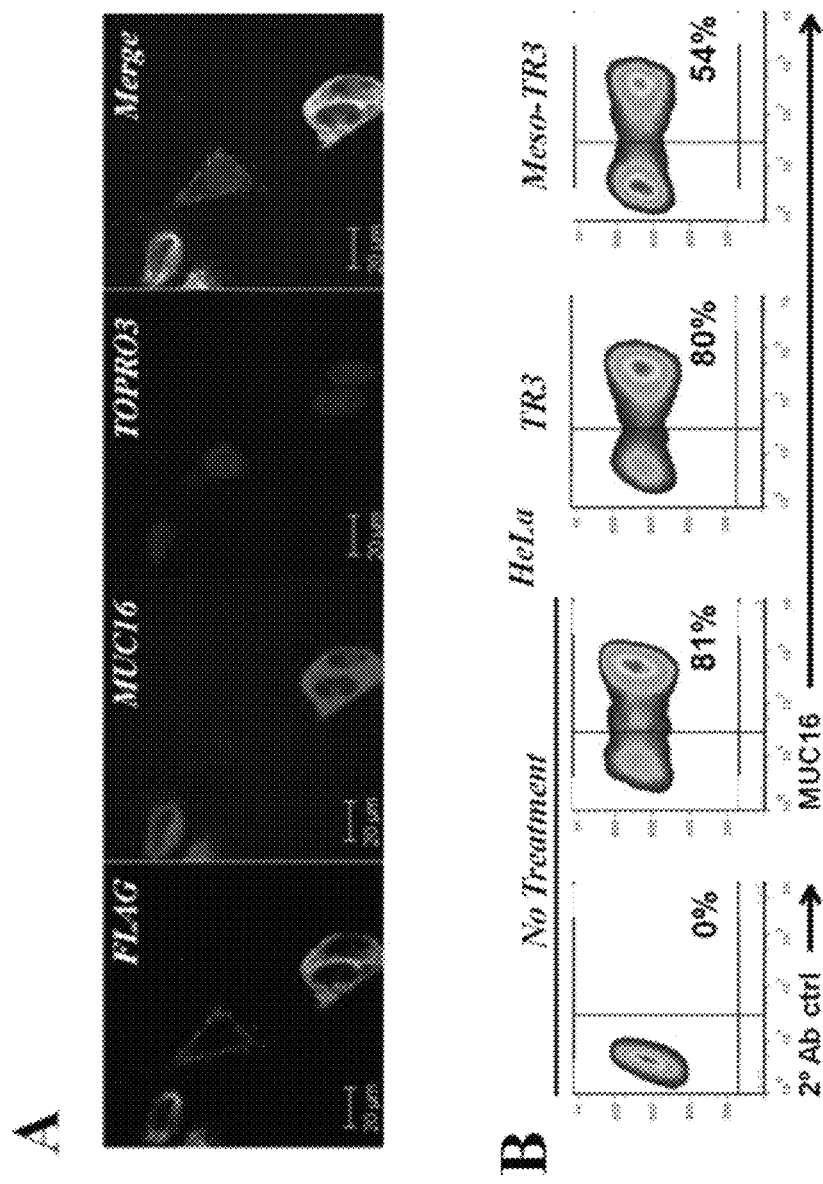
FIG. 8A-B illustrates selective killing of MUC16-expressing tumor cells by a mesothelin-TR3 fusion polypeptide.

This example illustrates that mesothelin-TR3 selectively kills MUC16-expressing cells. In order to study drug selectivity aspects of Meso-TR3 toward MUC16-expressing targets, we took advantage of the fact that HeLa cells are composed of a native mix of MUC16-positive and negative cells (80% and 20%, respectively). We therefore performed confocal microscopy on HeLa targets for tethering Meso-TR3. And indeed, those cells positive for the MUC16 tumor marker were heavily coated with Meso-TR3 (FIG. 8A). However, cells with a low or absent antigen expression were incapable of capturing Meso-TR3 and stained only weakly for the targeted drug (FIG. 8A, arrow). Based on these findings, we anticipated that Meso-TR3 would have a higher affinity for the MUC16-positive population within the mix and selectively eliminate these from the cell pool. And indeed, Meso-TR3 treatment resulted in a more than 30% reduction of MUC16-positive cells from 80% to 54% (FIG. 8B). In contrast, non-targeted TR3 was incapable of shifting the MUC16 ratio in this cervical cancer cell line due to the fact that it cannot discriminate between the two cell populations.

In these experiments (FIG. 8), HeLa cells were grown on 4-chamber slides and incubated the following day with Meso-TR3 complexed with DR5-Fc (8A). After washing, the cells were stained with a mixture of MUC16 pAb (red) and FLAG mAb (green), respectively. The cells were counterstained with TOPRO3 (blue, nuclei) and analyzed by confocal microscopy. The individual channels were overlaid to document co-localization of tumor marker and the targeted cancer drug (Merge). Original magnification: 63×. B, HeLa cells were treated with TR3 and Meso-TR3 for 24 h. Two days post-treatment, the cells were assessed for changes in the MUC16 ratio using flow cytometry. Representative density plots are shown from experiments done at least twice in duplicates. These data indicate that Mesothelin-TR3 is more potent against MUC16-positive cells compared to TR3 alone.

Example 7

Figure 9:
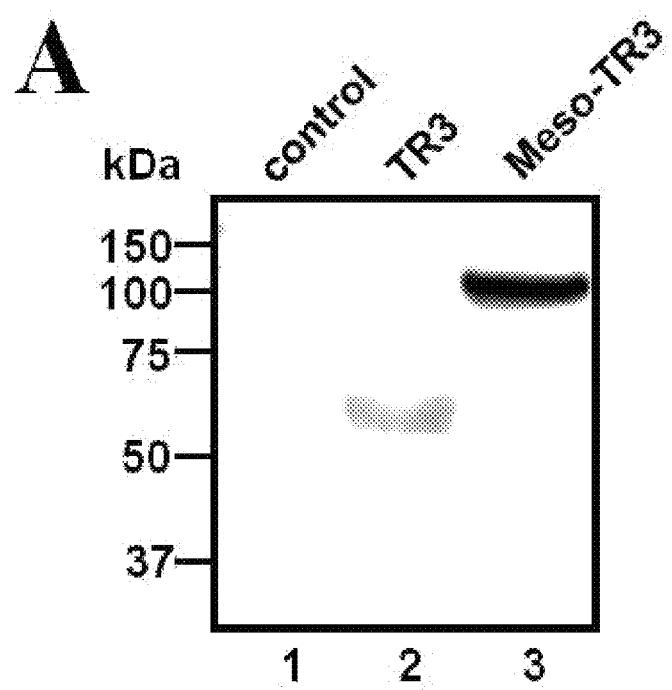
FIG. 9A-B illustrates that Meso-TR3 is fully activated on tumor cells expressing the biomarker MUC16.
Figure 9:
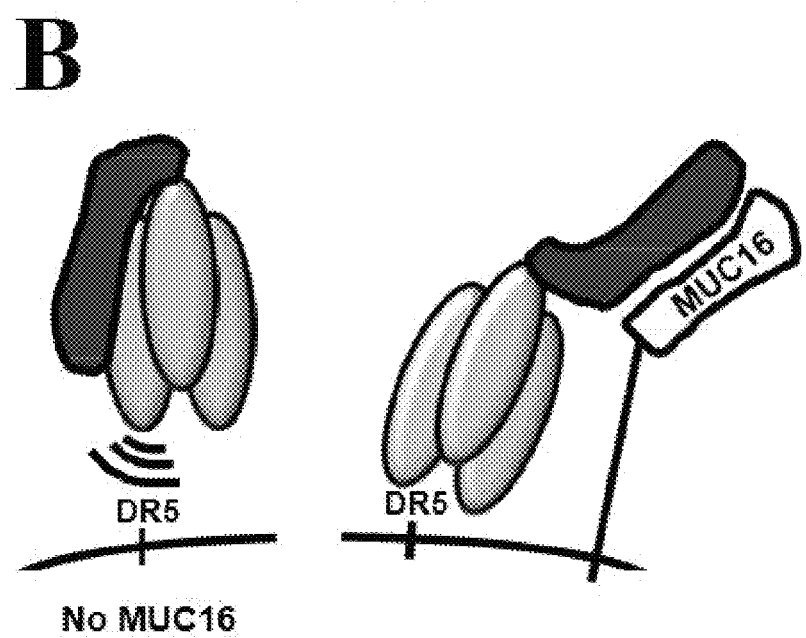

This example illustrates that Meso-TR3 is a cancer drug with prodrug properties and is fully activated on tumor cells expressing the biomarker MUC16 (FIG. 9).

Since the activity profiles of our TR3 drugs were routinely determined via functional apoptosis assays on reporter cells that lack the tumor marker MUC16 (compare FIG. 6A), we wanted to confirm that the drug input was similar for the respective TR3 variant. In order to do this, we employed semi-quantitative Western blot analysis, a detection method that does not rely on a native protein conformation, such as a TRAIL ELISA. When drug concentrations were analyzed that achieved identical killing capacities on MUC16-negative Jurkat cells, we consistently found much stronger signal intensities for Meso-TR3 compared to TR3 with a ratio of ≈8 in favor of Meso-TR3 (FIG. 9A). These results suggest that, compared to TR3 alone, a significantly higher concentration of Meso-TR3 is required to achieve equivalent biological effects on MUC16-deficient cells (FIG. 9B).

In these experiments (FIG. 9), TR3 and Meso-TR3 preparations exerting identical killing profiles on MUC16-deficient tumor cells (A, compare with FIG. 6A) were subjected to semi-quantitative Western blot analysis under reducing conditions using anti-TRAIL pAb. The immunoreactive bands were quantified using QuantityOne® software (Bio-Rad, Hercules, Calif.) on a BioRad imaging system, with Meso-TR3 approximately 8-fold more abundant than TR3. B, Hypothetical proposed mechanism of Meso-TR3 activity. Without being limited by theory, the inventor have developed a hypothetical model. In this model, the mesothelin moiety of Meso-TR3 can partially interfere with an unrestricted interaction of the TR3 domain and its death receptors (left panel). In the presence of MUC16 on the cancer cell surface, the mesothelin targeting domain can be removed from the TR3 surface thus enabling unrestricted access to and full activation of the death receptor-mediated extrinsic death pathway (right panel).

Example 8

Figure 12:
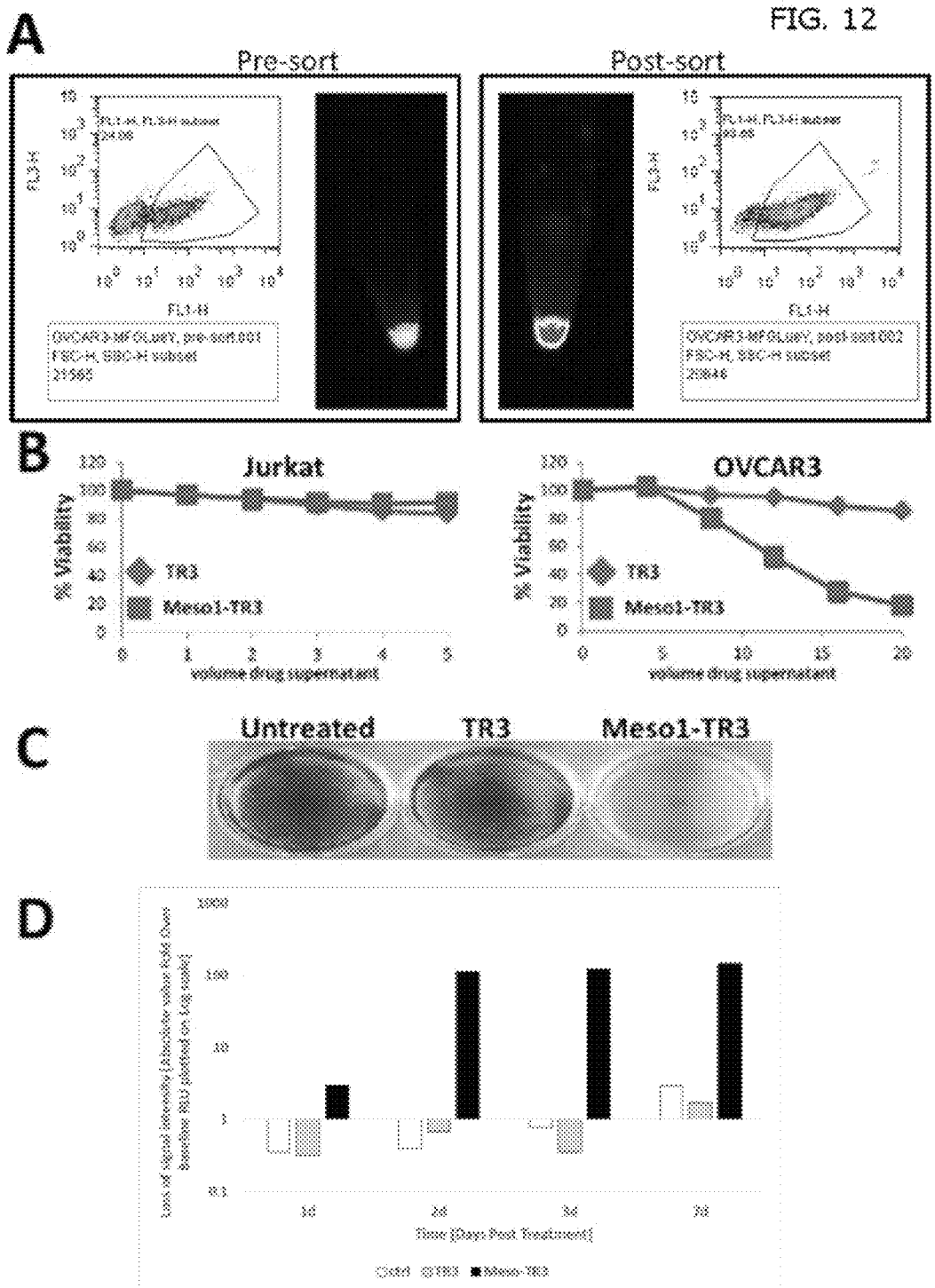
FIG. 12A-D illustrates reduction of tumor burden by Meso-TR3 in an in vivo model of ovarian cancer.

These experiments, depicted in FIG. 12, illustrate that Meso-TR3 reduces the tumor burden in an in vivo mouse model of ovarian cancer. As shown in FIG. 12: A, ovarian cancer cell line OVCAR3 was genetically engineered, via retroviral infection, to stably express the luciferase-YFP fusion protein with a transduction efficiency of 24% (left panel, "Pre-sort", along with the corresponding luciferase activity following addition of luciferin substrate). In order to enrich the luciferase expressing cells, FACS sort was performed, resulting in a stable cell pool with more than 93% YFP (luciferase)-positive cells (right panel, Post-sort", along with the corresponding luciferase activity following addition of luciferin substrate). B, Meso-TR3 and the parental TR3 protein preparations were tested in apoptosis assays and show similar killing activity on MUC16-negative Jurkat cells (left panel). The same protein preparations were than applied to MUC16-positive OVCAR3 cells (adherent) and document the much increased killing profile of Meso-TR3 compared to the non-targeted TR3 parental molecule (right panel). C, OVCAR3 cell were first non-enzymatically detached from the culture flasks using EDTA and treated in suspension with TR3 and Meso-TR3 at equipotent concentrations on Jurkat cells (compare B, left panel). The cells were allowed to settle and the surviving cells that adhered following drug treatment were stained 2 days later with crystal violet. Of note, Meso-TR3 almost completely eliminated the cancer cells, in agreement to what has been documented above when the cells were treated in an adherent state (B, right panel). FIG. 12 D and FIG. 13: for the functional assessment of MUC16-targeted Meso-TR3 in vivo, SCID mice were injected i.p. with 1×10⁶ YFP-sorted OVCAR3 cells (93%). The next day, luciferase expression was monitored via non-invasive whole animal imaging and the mice were treated for 7 days with equivalent doses of TR3 and Meso-TR3 via the i.p. route and imaged at the indicated intervals. Of note, only the mouse treated with Meso-TR3 showed a substantial decrease in signal intensity, which was nearly 150-fold less than the initial luciferase activity and suggests enhanced and selective elimination of the labeled cells from the peritoneal location. In contrast, in mice treated with medium alone (ctrl) and TR3, the signal intensity did not change and support the results obtained from in vitro killing experiment.

Example 9

Figure 13:
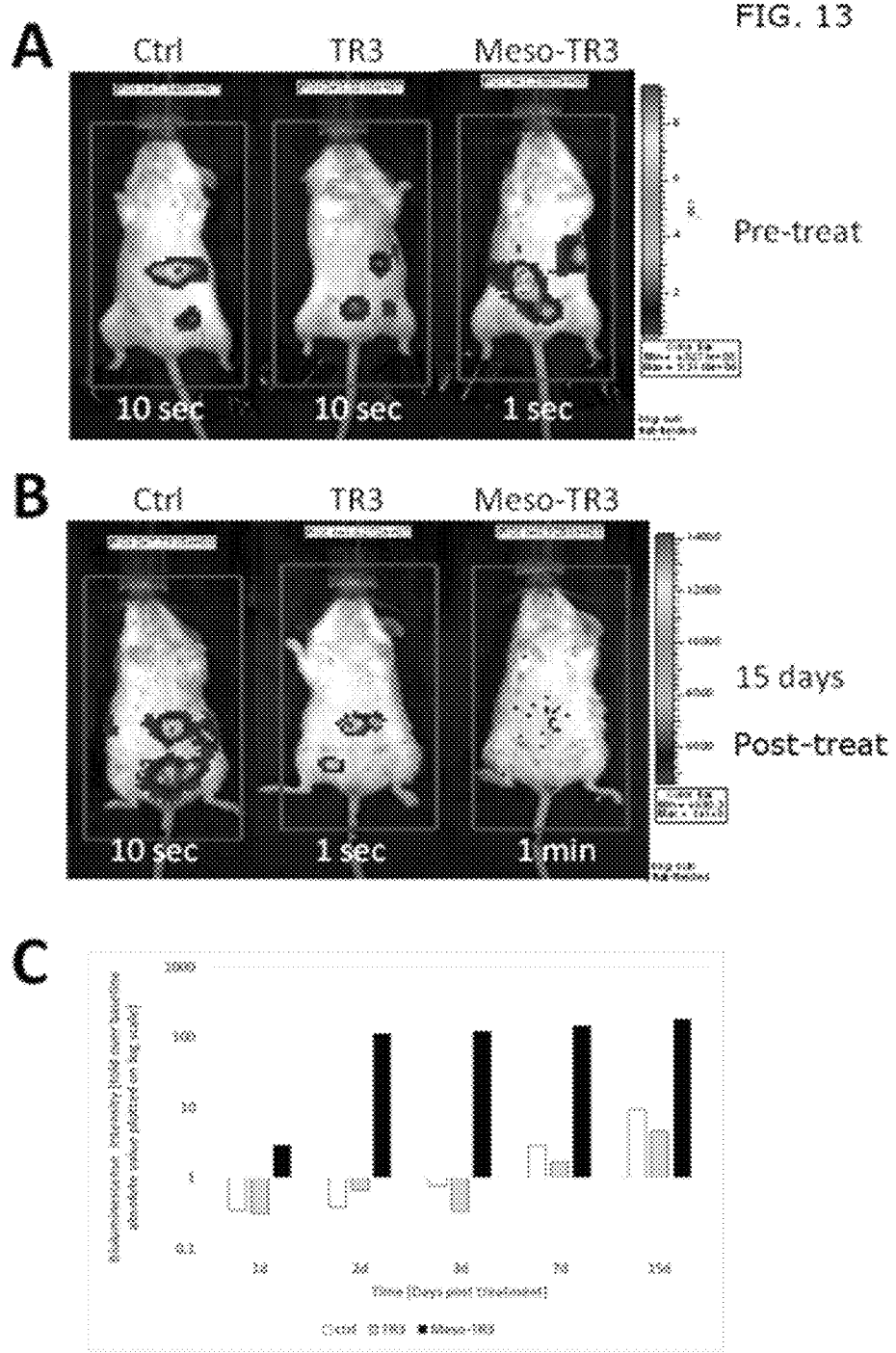
FIG. 13A-C illustrates examples of reduction of tumor burden by Meso-TR3 in an in vivo model of ovarian cancer.

These experiments, depicted in FIG. 13 illustrate that Meso-TR3 reduces the tumor burden in an in vivo mouse model of ovarian cancer.

In these experiments, animals bearing MUC16-positive tumors expressing the luciferase-YFP fusion protein (as in Example 8) were treated with TR3, Meso-TR3, or control.

FIG. 13 illustrates examples of model animals treated with TR3, Meso-TR3, or control. Control, TR3 and Meso-TR3 treated animals bearing ovarian cancer cell line OVCAR3 were imaged at the indicated times. In FIG. 13, A illustrates luciferase intensities prior to treatment, whereas B illustrates luciferase intensities 15 days post-treatment. Times beneath animals in A and B indicate duration of camera exposures. C illustrates a dramatic drop in image intensity in the animal receiving Meso-TR3 at 15 days. Note low level of signal obtained 15 days post-treatment in an animal which received Meso-TR3 even after a 1 min. camera exposure (B), whereas an animal receiving TR3 or control had much greater signals 15 days post-treatment. Data is normalized for photons/second. These data demonstrate therapeutic effectiveness of meso-TR3 against tumors including MUC16-positive tumors.

Example 10

This example illustrates production and killing potential of TR3, Meso64-TR3, and Meso-TR3. In these experiments, a Titer-Glo® assay (Promega Corporation, Madison, Wis.) was used in accordance with the supplier's instructions.

Figure 14:
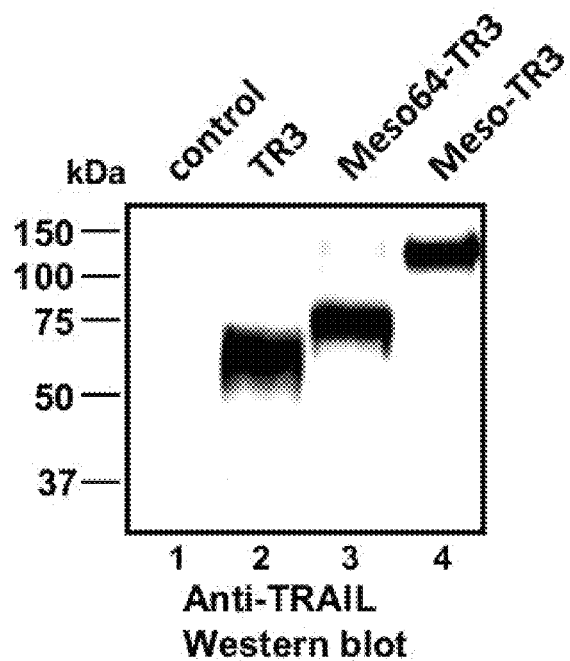
FIG. 14 illustrates production and killing potential of TR3, Meso64-TR3, and Meso-TR3.
Figure 14:
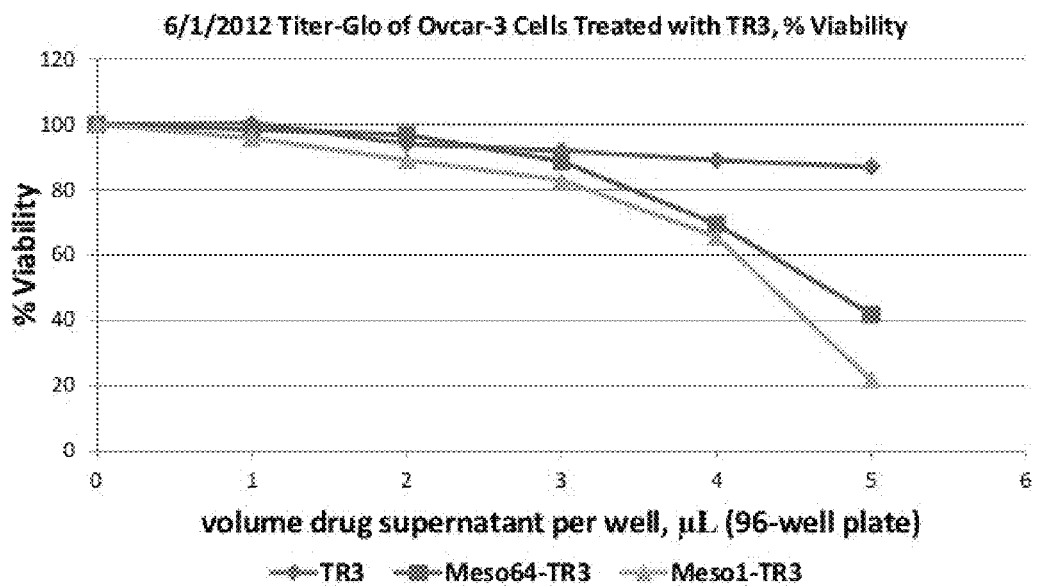

As shown in FIG. 14, the present inventors have demonstrated production in vitro of TR3, meso64-TR3, and Meso-TR3 (Western blot in upper panel). The present inventors also show the potency of Meso64-TR3 for killing Ovcar-3 ovarian cancer cells, and the even greater potency of Meso1-TR3 for killing Ovcar-3 ovarian cancer cells (cell killing curve in lower panel).

All references cited are hereby incorporated by reference, each in its entirety.

What is claimed is:

1. A trimer of a TNF-related apoptosis-inducing ligand (TRAIL), comprising:
   a mesothelin polypeptide; and
   three consecutive extracellular TRAIL domains fused together in a head-to-tail configuration.

2. A trimer in accordance with claim 1, further comprising a His-tag.

3. An anticancer therapeutic comprising a trimer in accordance with claim 1.

4. A nucleic acid comprising a sequence encoding the trimer of claim 1.

5. A vector comprising the nucleic acid of claim 4.

6. A vector of claim 4, wherein said vector is a plasmid.

7. A method of inducing apoptosis in a tumor cell, comprising contacting the tumor cell with a trimer of claim 1.

8. The method of inducing apoptosis in a tumor cell in accordance with claim 7, wherein the tumor cell expresses MUC16.

9. The method of inducing apoptosis in a tumor cell in accordance with claim 7, wherein the tumor cell is an ovarian cancer cell.

10. The method of inducing apoptosis in a tumor cell in accordance with claim 7, wherein the tumor cell is a pancreatic cancer cell.

11. The method of inducing apoptosis in a tumor cell in accordance with claim 7, wherein the tumor cell is a breast cancer cell.

12. A method of treating a cancer in a subject in need thereof, the method comprising administering to the subject a therapeutically effective amount of a trimer of claim 1.

13. The method of treating a cancer in a subject in accordance with claim 12, wherein the cancer comprises MUC16-positive cells.

14. The method of treating a cancer in a subject in accordance with claim 12, wherein the cancer comprises ovarian cancer cells.

15. The method of treating a cancer in a subject in accordance with claim 12, wherein the cancer comprises pancreatic cancer cells.

16. The method of treating a cancer in a subject in accordance with claim 12, wherein the cancer comprises breast cancer cells.

* * * * *

UNITED STATES PATENT AND TRADEMARK OFFICE
CERTIFICATE OF CORRECTION

PATENT NO. : 9,127,081 B2
APPLICATION NO. : 13/892238
DATED : September 8, 2015
INVENTOR(S) : Dirk Spitzer and William G Hawkins It is certified that error appears in the above-identified patent and that said Letters Patent is hereby corrected as shown below:

In the Specification

Column 1 Lines 17-20 should read:
This invention was made with government support under CA150945 awarded by the National Institutes of Health. The government has certain rights in the invention.

Signed and Sealed this
Thirteenth Day of August, 2019

Andrei Iancu
*Director of the United States Patent and Trademark Office*

SEQUENCE LISTING

```
<160> NUMBER OF SEQ ID NOS: 12

<210> SEQ ID NO 1
<211> LENGTH: 191
<212> TYPE: PRT
<213> ORGANISM: Homo sapiens

<400> SEQUENCE: 1

Met Ile Leu Arg Thr Ser Glu Glu Thr Ile Ser Thr Val Gln Glu Lys
1               5                   10                  15

Gln Gln Asn Ile Ser Pro Leu Val Arg Glu Arg Gly Pro Gln Arg Val
            20                  25                  30

Ala Ala His Ile Thr Gly Thr Arg Gly Arg Ser Asn Thr Leu Ser Ser
        35                  40                  45

Pro Asn Ser Lys Asn Glu Lys Ala Leu Gly Arg Lys Ile Asn Ser Trp
    50                  55                  60

Glu Ser Ser Arg Ser Gly His Ser Phe Leu Ser Asn Leu His Leu Arg
65                  70                  75                  80

Asn Gly Glu Leu Val Ile His Glu Lys Gly Phe Tyr Tyr Ile Tyr Ser
                85                  90                  95

Gln Thr Tyr Phe Arg Phe Gln Glu Glu Ile Lys Glu Asn Thr Lys Asn
            100                 105                 110

Asp Lys Gln Met Val Gln Tyr Ile Tyr Lys Tyr Thr Ser Tyr Pro Asp
        115                 120                 125

Pro Ile Leu Leu Met Lys Ser Ala Arg Asn Ser Cys Trp Ser Lys Asp
    130                 135                 140

Ala Glu Tyr Gly Leu Tyr Ser Ile Tyr Gln Gly Gly Ile Phe Glu Leu
145                 150                 155                 160

Lys Glu Asn Asp Arg Ile Phe Val Ser Val Thr Asn Glu His Leu Ile
                165                 170                 175

Asp Met Asp His Glu Ala Ser Phe Phe Gly Ala Phe Leu Val Gly
            180                 185                 190

<210> SEQ ID NO 2
<211> LENGTH: 6113
<212> TYPE: DNA
<213> ORGANISM: Artificial Sequence
```

<220> FEATURE:
<223> OTHER INFORMATION: plasmid encoding fusion polypeptide

<400> SEQUENCE: 2

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta atttttttta tttatgcaga ggccgaggcc     300
gcctcggcct ctgagctatt ccagaagtag tgaggaggct tttttggagg cctaggcttt     360
tgcaaaaagc tggatcgatc ctgagaactt cagggtgagt ttggggaccc ttgattgttc     420
tttctttttc gctattgtaa aattcatgtt atatggaggg gcaaagtttt caggggtgtt     480
gtttagaatg ggaagatgtc ccttgtatca ccatggaccc tcatgataat tttgtttctt     540
tcactttcta ctctgttgac aaccattgtc tcctcttatt ttcttttcat tttctgtaac     600
ttttcgtta aactttagct tgcatttgta acgaattttt aaattcactt tgttttattt     660
gtcagattgt aagtactttc tctaatcact ttttttcaa gcaatcagg gtatattata     720
ttgtacttca gcacagtttt agagaacaat tgttataatt aaatgataag gtagaatatt     780
tctgcatata aattctggct ggcgtggaaa tattcttatt ggtagaaaca actacatcct     840
ggtcatcatc ctgcctttct ctttatggtt acaatgatat acactgtttg agatgaggat     900
aaaatactct gagtccaaac cgggcccctc tgctaaccat gttcatgcct tcttcttttt     960
cctacagctc ctgggcaacg tgctggttat tgtgctgtct catcattttg gcaaagaatt    1020
gtaatacgac tcactatagg gcgaattcag gttctgtgga caatcacaat gggaatccaa    1080
ggagggtctg tcctgttcgg gctgctgctc gtcctggctg tcttctgcca ttcaggtcat    1140
agcctgcaga gctacaaccc tccgcgtacg gactacaagg acgatgatga caaacagatc    1200
agcggtggag gctcagaagt ggagaagaca gcctgtcctt caggcaagaa ggcccgcgag    1260
atagacgaga gcctcatctt ctacaagaag tgggagctgg aagcctgcgt ggatgcggcc    1320
ctgctggcca cccagatgga ccgcgtgaac gccatcccct tcacctacga gcagctggac    1380
gtcctaaagc ataaactgga tgagctcggt ggaggctcag gtacgccacc tatgattttg    1440
agaacctctg aggaaaccat ttctacagtt caagaaaagc aacaaaatat ttctccccta    1500
gtgagagaaa gaggtcctca gagagtagca gctcacataa ctgggaccag aggaagaagc    1560
aacacattgt cttctccaaa ctccaagaat gaaaaggctc tgggccgcaa aataaactcc    1620
tgggaatcat caaggagtgg gcattcattc ctgagcaact tgcacttgag gaatggtgaa    1680
ctggtcatcc atgaaaaagg gttttactac atctattccc aaacatactt tcgatttcag    1740
gaggaaataa agaaaacac aaagaacgac aaacaaatgg tccaatatat ttacaaatac    1800
acaagttatc ctgaccctat attgttgatg aaaagtgcta gaaatagttg ttggtctaaa    1860
gatgcagaat atggactcta ttccatctat caaggggaa tatttgagct taaggaaaat    1920
gacagaattt tgtttctgt aacaaatgag cacttgatag acatggacca tgaagccagt    1980
tttttcgggg ccttttagt tggcagatcc caaaatattt ctcccctagt gagagaaaga    2040
ggtcctcaga gagtagcagc tcacataact gggaccagag gaagaagcaa cacattgtct    2100
tctccaaact ccaagaatga aaaggctctg gccgcaaaa taaactcctg gaatcatca    2160
aggagtgggc attcattcct gagcaacttg cacttgagga atggtgaact ggtcatccat    2220
```

```
gaaaaagggt tttactacat ctattcccaa acatactttc gatttcagga ggaaataaaa   2280
gaaaacacaa agaacgacaa acaaatggtc caatatattt acaaatacac aagttatcct   2340
gaccctatat tgttgatgaa agtgctaga aatagttgtt ggtctaaaga tgcagaatat    2400
ggactctatt ccatctatca agggggaata tttgagctta aggaaaatga cagaattttt   2460
gtttctgtaa caaatgagca cttgatagac atggaccatg aagccagttt tttcggggcc   2520
tttttagttg gcagatccca ccaccaccac caccaccaaa atatttctcc cctagtgaga   2580
gaaagaggtc ctcagagagt agcagctcac ataactggga ccagaggaag aagcaacaca   2640
ttgtcttctc caaactccaa gaatgaaaag gctctgggcc gcaaaataaa ctcctgggaa   2700
tcatcaagga gtgggcattc attcctgagc aacttgcact tgaggaatgg tgaactggtc   2760
atccatgaaa aagggtttta ctacatctat tcccaaacat actttcgatt tcaggaggaa   2820 ataaagaaa acacaaagaa cgacaaacaa atggtccaat atatttacaa atacacaagt    2880
tatcctgacc ctatattgtt gatgaaaagt gctagaaata gttgttggtc taaagatgca   2940
gaatatggac tctattccat ctatcaaggg ggaatatttg agcttaagga aaatgacaga   3000 attttttgttt ctgtaacaaa tgagcacttg atagacatgg accatgaagc cagttttttc   3060
ggggcctttt tagttggcag atcttaatct aggatcttat taaagcagaa cttgtttatt   3120
gcagcttata atggttacaa ataaagcaat agcatcacaa atttcacaaa taaagcattt   3180
ttttcactgc attctagttg tggtttgtcc aaactcatca atgtatctta tcatgtctgg   3240
tcgactctag actcttccgc ttcctcgctc actgactcgc tgcgctcggt cgttcggctg   3300
cggcgagcgg tatcagctca ctcaaaggcg gtaatacggt tatccacaga atcaggggat   3360
aacgcaggaa agaacatgtg agcaaaaggc cagcaaaagg ccaggaaccg taaaaaggcc   3420
gcgttgctgg cgttttttcca taggctccgc cccctgacg agcatcacaa aaatcgacgc   3480
tcaagtcaga ggtggcgaaa cccgacagga ctataaagat accaggcgtt tccccctgga   3540
agctccctcg tgcgctctcc tgttccgacc ctgccgctta ccggatacct gtccgccttt   3600
ctcccttcgg gaagcgtggc gctttctcaa tgctcacgct gtaggtatct cagttcggtg   3660
taggtcgttc gctccaagct gggctgtgtg cacgaacccc ccgttcagcc cgaccgctgc   3720
gccttatccg gtaactatcg tcttgagtcc aacccggtaa gacacgactt atcgccactg   3780
gcagcagcca ctggtaacag gattagcaga gcgaggtatg taggcggtgc tacagagttc   3840
ttgaagtggt ggcctaacta cggctacact agaaggacag tatttggtat ctgcgctctg   3900
ctgaagccaa ttaccttcgg aaaaagagtt ggtagctctt gatccggcaa acaaaccacc   3960
gctggtagcg gtggtttttt tgtttgcaag cagcagatta cgcgcagaaa aaaaggatct   4020
caagaagatc ctttgatctt ttctacgggg tctgacgctc agtggaacga aaactcacgt   4080
taagggattt tggtcatgag attatcaaaa aggatcttca cctagatcct tttaaattaa   4140
aaatgaagtt ttaaatcaat ctaaagtata tatgagtaaa cttggtctga cagttaccaa   4200
tgcttaatca gtgaggcacc tatctcagcg atctgtctat ttcgttcatc catagttgcc   4260
tgactccccg tcgtgtagat aactacgata cgggagggct taccatctgg ccccagtgct   4320
gcaatgatac cgcgagaccc acgctcaccg gctccagatt tatcagcaat aaaccagcca   4380
gccggaaggg ccgagcgcag aagtggtcct gcaactttat ccgcctccat ccagtctatt   4440
aattgttgcc gggaagctag agtaagtagt tcgccagtta atagtttgcg caacgttgtt   4500
gccattgcta caggcatcgt ggtgtcacgc tcgtcgtttg gtatggcttc attcagctcc   4560
ggttcccaac gatcaaggcg agttacatga tcccccatgt tgtgcaaaaa agcggttagc   4620
```

```
tccttcggtc ctccgatcgt tgtcagaagt aagttggccg cagtgttatc actcatggtt      4680
atggcagcac tgcataattc tcttactgtc atgccatccg taagatgctt ttctgtgact      4740
ggtgagtact caaccaagtc attctgagaa tagtgtatgc ggcgaccgag ttgctcttgc      4800
ccggcgtcaa tacgggataa taccgcgcca catagcagaa ctttaaaagt gctcatcatt      4860
ggaaaacgtt cttcggggcg aaaactctca aggatcttac cgctgttgag atccagttcg      4920
atgtaaccca ctcgtgcacc caactgatct tcagcatctt ttactttcac cagcgtttct      4980
gggtgagcaa aaacaggaag gcaaaatgcc gcaaaaaagg gaataagggc gacacggaaa      5040
tgttgaatac tcatactctt ctttttttcaa tattattgaa gcatttatca gggttattgt      5100
ctcatgagcg gatacatatt tgaatgtatt tagaaaaata aacaaatagg ggttccgcgc      5160
acatttcccc gaaaagtgcc acctgacgtc taagaaacca ttattatcat gacattaacc      5220
tataaaaata ggcgtatcac gaggcccctt cgtctcgcgc gtttcggtg atgacggtga       5280 aaacctctga cacatgcagc tcccggagac ggtcacagct tgtctgtaag cggatgccgg      5340
gagcagacaa gcccgtcagg gcgcgtcagc gggtgttggc gggtgtcggg gctggcttaa      5400
ctatgcggca tcagagcaga ttgtactgag agtgcaccat atgcggtgtg aaataccgca      5460
cagatgcgta aggagaaaat accgcatcag gaaattgtaa acgttaatat tttgttaaaa      5520
ttcgcgttaa attttgttta aatcagctca ttttttaacc aataggccga atcggcaaa       5580 atcccttata aatcaaaaga atagaccgag atagggttga gtgttgttcc agtttggaac      5640
aagagtccac tattaagaa cgtggactcc aacgtcaaag ggcgaaaaac cgtctatcag        5700
ggcgatggcc cactacgtga accatcaccc taatcaagtt ttttggggtc gaggtgccgt      5760
aaagcactaa atcggaaccc taaagggagc cccgattta gagcttgacg gggaaagccg        5820
gcgaacgtgg cgagaaagga agggaagaaa gcgaaaggag cgggcgctag ggcgctggca      5880
agtgtagcgg tcacgctgcg cgtaaccacc acacccgccg cgcttaatgc gccgctacag      5940
ggcgcgtcgc gccattcgcc attcaggcta cgcaactgtt gggaagggcg atcggtgcgg      6000
gcctcttcgc tattacgcca gctggcgaag ggggatgtg ctgcaaggcg attaagttgg       6060
gtaacgccag ggttttccca gtcacgacgt tgtaaaacga cggccagtga att             6113
```

<210> SEQ ID NO 3
<211> LENGTH: 6767
<212> TYPE: DNA
<213> ORGANISM: Artificial Sequence
<220> FEATURE:
<223> OTHER INFORMATION: plasmid encoding fusion polypeptide

<400> SEQUENCE: 3

```
gtcgacttct gaggcggaaa gaaccagctg tggaatgtgt gtcagttagg gtgtggaaag        60
tccccaggct ccccagcagg cagaagtatg caaagcatgc atctcaatta gtcagcaacc       120
aggtgtggaa agtccccagg ctccccagca ggcagaagta tgcaaagcat gcatctcaat       180
tagtcagcaa ccatagtccc gcccctaact ccgcccatcc cgcccctaac tccgcccagt       240
tccgcccatt ctccgcccca tggctgacta attttttttta tttatgcaga ggccgaggcc      300
gcctcggcct ctgagctatt ccagaagtag tgaggaggct ttttttggagg cctaggcttt      360 tgcaaaaagc tggatcgatc ctgagaactt cagggtgagt ttggggaccc ttgattgttc      420 tttcttttc gctattgtaa aattcatgtt atatggaggg ggcaaagttt tcagggtgtt       480
gtttagaatg ggaagatgtc ccttgtatca ccatggaccc tcatgataat tttgtttctt      540
```

```
tcactttcta ctctgttgac aaccattgtc tcctcttatt ttcttttcat tttctgtaac    600
tttttcgtta aactttagct tgcatttgta acgaattttt aaattcactt ttgtttattt    660
gtcagattgt aagtactttc tctaatcact ttttttcaa ggcaatcagg gtatattata    720
ttgtacttca gcacagtttt agagaacaat tgttataatt aaatgataag gtagaatatt    780
tctgcatata aattctggct ggcgtggaaa tattcttatt ggtagaaaca actacatcct    840
ggtcatcatc ctgcctttct ctttatggtt acaatgatat acactgtttg agatgaggat    900
aaaatactct gagtccaaac cgggcccctc tgctaaccat gttcatgcct tcttcttttt    960
cctacagctc ctgggcaacg tgctggttat tgtgctgtct catcattttg gcaaagaatt   1020
gtaatacgac tcactatagg gcgaattcag gttctgtgga caatcacaat gggaatccaa   1080
ggagggtctg tcctgttcgg gctgctgctc gtcctggctg tcttctgcca ttcaggtcat   1140
agcctgcaga gctacaaccc tccgcgtacg gactacaagg acgatgatga caaacagatc   1200
agcggtggag gctcagaagt ggagaagaca gcctgtcctt caggcaagaa ggcccgcgag   1260
atagacgaga gcctcatctt ctacaagaag tgggagctgg aagcctgcgt ggatgcggcc   1320
ctgctggcca cccagatgga ccgcgtgaac gccatcccct tcacctacga gcagctggac   1380
gtcctaaagc ataaactgga tgagctctac ccacaaggtt accccgagtc tgtgatccag   1440
cacctgggct acctcttcct caagatgagc cctgaggaca ttcgcaagtg aatgtgacg    1500
tccctggaga ccctgaaggc tttgcttgaa gtcaacaaag gcacgaaat gagtcctcag    1560
gtggccaccc tgatcgaccg ctttgtgaag ggaaggggcc agctagacaa agacacccta   1620
gacaccctga ccgccttcta ccctgggtac ctgtgctccc tcagccccga ggagctgagc   1680
tccgtgcccc ccagcagcat ctgggcggtc aggccccagg acctggacac gtgtgaccca   1740
aggcagctgg acgtcctcta tcccaaggcc cgccttgctt tccagaacat gaacgggtcc   1800
gaatacttcg tgaagatcca gtccttcctg ggtggggccc cacggaggga tttgaaggcg   1860
ctcagtcagc agaatgtgag catggacttg gccacgttca tgaagctgcg gacgatgcg    1920
gtgctgccgt tgactgtggc tgaggtgcag aaacttctgg accccacgt ggagggcctg    1980
aaggcggagg agcggcaccg cccggtgcgg gactggatcc tacggcagcg gcaggacgac   2040
ctggacacgc tggggctggg gctacagggc ctgcgtacgc cacctatgat tttgagaacc   2100
tctgaggaaa ccatttctac agttcaagaa aagcaacaaa atatttctcc cctagtgaga   2160
gaaagaggtc ctcagagagt agcagctcac ataactggga ccagaggaag aagcaacaca   2220
ttgtcttctc caaactccaa gaatgaaaag gctctgggcc gcaaaataaa ctcctgggaa   2280
tcatcaagga gtgggcattc attcctgagc aacttgcact tgaggaatgg tgaactggtc   2340
atccatgaaa aagggtttta ctacatctat tcccaaacat actttcgatt tcaggaggaa   2400
ataaaagaaa acacaaagaa cgacaaacaa atggtccaat atatttacaa atacacaagt   2460
tatcctgacc ctatattgtt gatgaaaagt gctagaaata gttgttggtc taaagatgca   2520
gaatatggac tctattccat ctatcaaggg ggaatatttg agcttaagga aaatgacaga   2580
atttttgttt ctgtaacaaa tgagcacttg atagacatgg accatgaagc cagttttttc    2640
ggggccttt  tagttggcag atcccaaaat atttctcccc tagtgagaga aagaggtcct   2700
cagagagtag cagctcacat aactgggacc agaggaagaa gcaacacatt gtcttctcca   2760
aactccaaga atgaaaaggc tctgggccgc aaaataaact cctgggaatc atcaaggagt   2820
gggcattcat tcctgagcaa cttgcacttg aggaatggtg aactggtcat ccatgaaaaa   2880
gggttttact acatctattc ccaaacatac tttcgatttc aggaggaaat aaaagaaaac   2940
```

```
acaaagaacg acaaacaaat ggtccaatat atttacaaat acacaagtta tcctgaccct   3000
atattgttga tgaaaagtgc tagaaatagt tgttggtcta aagatgcaga atatggactc   3060
tattccatct atcaaggggg aatatttgag cttaaggaaa atgacagaat ttttgtttct   3120
gtaacaaatg agcacttgat agacatggac catgaagcca gttttttcgg ggccttttta   3180
gttggcagat cccaccacca ccaccaccac caaaatattt ctcccctagt gagagaaaga   3240
ggtcctcaga gagtagcagc tcacataact gggaccagag aagaagcaa cacattgtct    3300
tctccaaact ccaagaatga aaaggctctg gccgcaaaa taaactcctg ggaatcatca    3360
aggagtgggc attcattcct gagcaacttg cacttgagga atggtgaact ggtcatccat   3420
gaaaaagggt tttactacat ctattcccaa acatactttc gatttcagga ggaaataaaa   3480
gaaaacacaa agaacgacaa acaaatggtc caatatattt acaaatacac aagttatcct   3540
gaccctatat tgttgatgaa aagtgctaga atagttgtt ggtctaaaga tgcagaatat    3600
ggactctatt ccatctatca agggggaata tttgagctta aggaaaatga cagaattttt   3660
gtttctgtaa caaatgagca cttgatagac atggaccatg aagccagttt tttcggggcc   3720
ttttagttg gcagatctta atctaggatc ttattaaagc agaacttgtt tattgcagct    3780
tataatggtt acaaataaag caatagcatc acaaatttca caaataaagc attttttca    3840
ctgcattcta gttgtggttt gtccaaactc atcaatgtat cttatcatgt ctggtcgact   3900
ctagactctt ccgcttcctc gctcactgac tcgctgcgct cggtcgttcg gctgcggcga   3960
gcggtatcag ctcactcaaa ggcggtaata cggttatcca cagaatcagg ggataacgca   4020
ggaaagaaca tgtgagcaaa aggccagcaa aaggccagga accgtaaaaa ggccgcgttg   4080
ctggcgtttt tccataggct ccgcccccct gacgagcatc acaaaaatcg acgctcaagt   4140
cagaggtggc gaaacccgac aggactataa agataccagg cgtttccccc tggaagctcc   4200
ctcgtgcgct ctcctgttcc gaccctgccg cttaccggat acctgtccgc ctttctccct   4260
tcgggaagcg tggcgctttc tcaatgctca cgctgtaggt atctcagttc ggtgtaggtc   4320
gttcgctcca agctgggctg tgtgcacgaa ccccccgttc agcccgaccg ctgcgcctta   4380
tccggtaact atcgtcttga gtccaacccg gtaagcacg acttatcgcc actggcagca    4440
gccactggta acaggattag cagagcgagg tatgtaggcg gtgctacaga gttcttgaag   4500
tggtggccta actacggcta cactagaagg acagtatttg gtatctgcgc tctgctgaag   4560
ccagttacct tcggaaaaag agttggtagc tcttgatccg gcaaacaaac caccgctggt   4620
agcggtggtt tttttgtttg caagcagcag attacgcgca gaaaaaaagg atctcaagaa   4680
gatcctttga tcttttctac ggggtctgac gctcagtgga acgaaaactc acgttaaggg   4740
attttggtca tgagattatc aaaaaggatc ttcacctaga tccttttaaa ttaaaaatga   4800
agttttaaat caatctaaag tatatatgag taaacttggt ctgacagtta ccaatgctta   4860
atcagtgagg cacctatctc agcgatctgt ctatttcgtt catccatagt tgcctgactc   4920
cccgtcgtgt agataactac gatacgggag ggcttaccat ctggccccag tgctgcaatg   4980
ataccgcgag acccacgctc accggctcca gatttatcag caataaacca gccagccgga   5040
agggccgagc gcagaagtgg tcctgcaact ttatccgcct ccatccagtc tattaattgt   5100
tgccgggaag ctagagtaag tagttcgcca gttaatagtt tgcgcaacgt tgttgccatt   5160
gctacaggca tcgtggtgtc acgctcgtcg tttggtatgg cttcattcag ctccggttcc   5220
caacgatcaa ggcgagttac atgatccccc atgttgtgca aaaaagcggt tagctccttc   5280
```

```
ggtcctccga tcgttgtcag aagtaagttg gccgcagtgt tatcactcat ggttatggca    5340
gcactgcata attctcttac tgtcatgcca tccgtaagat gcttttctgt gactggtgag    5400
tactcaacca agtcattctg agaatagtgt atgcggcgac cgagttgctc ttgcccggcg    5460
tcaatacggg ataataccgc gccacatagc agaactttaa aagtgctcat cattggaaaa    5520
cgttcttcgg ggcgaaaact ctcaaggatc ttaccgctgt tgagatccag ttcgatgtaa    5580
cccactcgtg cacccaactg atcttcagca tcttttactt tcaccagcgt ttctgggtga    5640
gcaaaaacag gaaggcaaaa tgccgcaaaa aagggaataa gggcgacacg gaaatgttga    5700
atactcatac tcttcttttt tcaatattat tgaagcattt atcagggtta ttgtctcatg    5760
agcggataca tatttgaatg tatttagaaa aataaacaaa taggggttcc gcgcacattt    5820
ccccgaaaag tgccacctga cgtctaagaa accattatta tcatgacatt aacctataaa    5880
aataggcgta tcacgaggcc cctttcgtct cgcgcgtttc ggtgatgacg gtgaaaacct    5940
ctgacacatg cagctcccgg agacggtcac agcttgtctg taagcggatg ccggagcag    6000 acaagcccgt cagggcgcgt cagcgggtgt tggcgggtgt cggggctggc ttaactatgc    6060
ggcatcagag cagattgtac tgagagtgca ccatatgcgg tgtgaaatac cgcacagatg    6120
cgtaaggaga aaataccgca tcaggaaatt gtaaacgtta tattttgtt aaaattcgcg    6180 ttaaattttt gttaaatcag ctcattttt aaccaatagg ccgaaatcgg caaaatccct    6240
tataaatcaa aagaatagac cgagataggg ttgagtgttg ttccagtttg gaacaagagt    6300
ccactattaa agaacgtgga ctccaacgtc aaagggcgaa aaaccgtcta tcagggcgat    6360
ggcccactac gtgaaccatc accctaatca agttttttgg ggtcgaggtg ccgtaaagca    6420
ctaaatcgga accctaaagg gagcccccga tttagagctt gacggggaaa gccggcgaac    6480
gtggcgagaa aggaagggaa gaaagcgaaa ggagcgggcg ctagggcgct ggcaagtgta    6540
gcggtcacgc tgcgcgtaac caccacaccc gccgcgctta atgcgccgct acagggcgcg    6600
tcgcgccatt cgccattcag gctacgcaac tgttgggaag ggcgatcggt gcgggcctct    6660
tcgctattac gccagctggc gaagggggga tgtgctgcaa ggcgattaag ttgggtaacg    6720
ccagggtttt cccagtcacg acgttgtaaa acgacggcca gtgaatt       6767
```

<210> SEQ ID NO 4
<211> LENGTH: 5858
<212> TYPE: DNA
<213> ORGANISM: artificial
<220> FEATURE:
<223> OTHER INFORMATION: plasmid encoding fusion polypeptide

<400> SEQUENCE: 4

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta attttttta tttatgcaga ggccgaggcc     300
gcctcggcct ctgagctatt ccagaagtag tgaggaggct tttttggagg cctaggcttt     360
tgcaaaaagc tggatcgatc ctgagaactt cagggtgagt ttggggaccc ttgattgttc     420
tttctttttc gctattgtaa aattcatgtt atatggaggg gcaaagtttc agggtgtt      480 gtttagaatg gaagatgtc ccttgtatca ccatggaccc tcatgataat tttgtttctt     540
tcactttcta ctctgttgac aaccattgtc tcctcttatt ttcttttcat ttctgtaac     600
```

```
tttttcgtta aactttagct tgcatttgta acgaattttt aaattcactt ttgtttattt      660
gtcagattgt aagtactttc tctaatcact ttttttttcaa ggcaatcagg gtatattata     720
ttgtacttca gcacagtttt agagaacaat tgttataatt aaatgataag gtagaatatt     780
tctgcatata aattctggct ggcgtggaaa tattcttatt ggtagaaaca actacatcct     840
ggtcatcatc ctgcctttct ctttatggtt acaatgatat acactgtttg agatgaggat     900
aaaatactct gagtccaaac cgggcccctc tgctaaccat gttcatgcct tcttcttttt     960
cctacagctc ctgggcaacg tgctggttat tgtgctgtct catcattttg gcaaagaatt    1020
gtaatacgac tcactatagg gcgaattcag gttctgtgga caatcacaat gggaatccaa    1080
ggagggtctg tcctgttcgg gctgctgctc gtcctggctg tcttctgcca ttcaggtcat    1140
agcctgcaga gctacaaccc tccgcgtacg ccacctatga ttttgagaac ctctgaggaa    1200
accatttcta cagttcaaga aaagcaacaa aatatttctc ccctagtgag agaaagaggt    1260
cctcagagag tagcagctca cataactggg accagaggaa gaagcaacac attgtcttct    1320
ccaaactcca agaatgaaaa ggctctgggc cgcaaaataa actcctggga atcatcaagg    1380
agtgggcatt cattcctgag caacttgcac ttgaggaatg gtgaactggt catccatgaa    1440
aaagggtttt actacatcta ttcccaaaca tactttcgat tcaggagga aataaaagaa     1500 aacacaaaga acgacaaaca aatggtccaa tatatttaca aatacacaag ttatcctgac    1560
cctatattgt tgatgaaaag tgctagaaat agttgttggt ctaaagatgc agaatatgga    1620
ctctattcca tctatcaagg gggaatattt gagcttaagg aaaatgacag aattttttgtt   1680 tctgtaacaa atgagcactt gatagacatg gaccatgaag ccagtttttt cggggccttt    1740
ttagttggca gatcccaaaa tatttctccc ctagtgagag aaagaggtcc tcagagagta    1800
gcagctcaca taactgggac cagaggaaga agcaacacat tgtcttctcc aaactccaag    1860
aatgaaaagg ctctgggccg caaaataaac tcctgggaat catcaaggag tgggcattca    1920
ttcctgagca acttgcactt gaggaatggt gaactggtca tccatgaaaa agggttttac    1980
tacatctatt cccaaacata ctttcgattt caggaggaaa taaaagaaaa cacaagaac    2040 gacaaacaaa tggtccaata tatttacaaa tacacaagtt atcctgaccc tatattgttg    2100
atgaaaagtg ctagaaatag ttgttggtct aaagatgcag aatatggact ctattccatc    2160
tatcaagggg gaatatttga gcttaaggaa atgacagaa ttttttgtttc tgtaacaaat    2220 gagcacttga tagacatgga ccatgaagcc agttttttcg gggcctttttt agttggcaga    2280 tcccaccacc accaccacca ccaaaatatt tctcccctag tgagagaaag aggtcctcag    2340
agagtagcag ctcacataac tgggaccaga ggaagaagca acacattgtc ttctccaaac    2400
tccaagaatg aaaaggctct gggccgcaaa ataaactcct gggaatcatc aaggagtggg    2460
cattcattcc tgagcaactt gcacttgagg aatggtgaac tggtcatcca tgaaaaaggg    2520
ttttactaca tctattccca acatactttt cgatttcagg aggaaataaa agaaaacaca    2580
aagaacgaca aacaaatggt ccaatatatt tacaaataca caagttatcc tgaccctata    2640
ttgttgatga aaagtgctag aaatagttgt tggtctaaag atgcagaata tggactctat    2700
tccatctatc aagggggaat atttgagctt aaggaaaatg acagaatttt tgtttctgta    2760
acaaatgagc acttgataga catggaccat gaagccagtt ttttcggggc cttttttagtt   2820 ggcagatctt aatctaggat cttattaaag cagaacttgt ttattgcagc ttataatggt    2880
tacaaataaa gcaatagcat cacaaatttc acaaataaag catttttttc actgcattct    2940
```

```
agttgtggtt tgtccaaact catcaatgta tcttatcatg tctggtcgac tctagactct    3000
tccgcttcct cgctcactga ctcgctgcgc tcggtcgttc ggctgcggcg agcggtatca    3060
gctcactcaa aggcggtaat acggttatcc acagaatcag gggataacgc aggaaagaac    3120
atgtgagcaa aaggccagca aaaggccagg aaccgtaaaa aggccgcgtt gctggcgttt    3180
ttccataggc tccgcccccc tgacgagcat cacaaaaatc gacgctcaag tcagaggtgg    3240
cgaaacccga caggactata aagataccag gcgtttcccc ctggaagctc cctcgtgcgc    3300
tctcctgttc cgaccctgcc gcttaccgga tacctgtccg cctttctccc ttcgggaagc    3360
gtggcgcttt ctcaatgctc acgctgtagg tatctcagtt cggtgtaggt cgttcgctcc    3420
aagctgggct gtgtgcacga acccccgtt cagcccgacc gctgcgcctt atccggtaac    3480
tatcgtcttg agtccaaccc ggtaagacac gacttatcgc cactggcagc agccactggt    3540
aacaggatta gcagagcgag gtatgtaggc ggtgctacag agttcttgaa gtggtggcct    3600
aactacggct acactagaag gacagtattt ggtatctgcg ctctgctgaa gccagttacc    3660
ttcggaaaaa gagttggtag ctcttgatcc ggcaaacaaa ccaccgctgg tagcggtggt    3720
ttttttgttt gcaagcagca gattacgcgc agaaaaaaag gatctcaaga agatcctttg    3780
atcttttcta cggggtctga cgctcagtgg aacgaaaact cacgttaagg attttggtc     3840
atgagattat caaaaaggat cttcacctag atccttttaa attaaaaatg aagttttaaa    3900
tcaatctaaa gtatatatga gtaaacttgg tctgacagtt accaatgctt aatcagtgag    3960
gcacctatct cagcgatctg tctatttcgt tcatccatag ttgcctgact ccccgtcgtg    4020
tagataacta cgatacggga gggcttacca tctggcccca gtgctgcaat gataccgcga    4080
gacccacgct caccggctcc agatttatca gcaataaacc agccagccgg aagggccgag    4140
cgcagaagtg gtcctgcaac tttatccgcc tccatccagt ctattaattg ttgccgggaa    4200
gctagagtaa gtagttcgcc agttaatagt ttgcgcaacg ttgttgccat tgctacaggc    4260
atcgtggtgt cacgctcgtc gtttggtatg gcttcattca gctccggttc ccaacgatca    4320
aggcgagtta catgatcccc catgttgtgc aaaaaagcgg ttagctcctt cggtcctccg    4380
atcgttgtca gaagtaagtt ggccgcagtg ttatcactca tggttatggc agcactgcat    4440
aattctctta ctgtcatgcc atccgtaaga tgcttttctg tgactggtga gtactcaacc    4500
aagtcattct gagaatagtg tatgcggcga ccgagttgct cttgcccggc gtcaatacgg    4560
gataataccg cgccacatag cagaacttta aaagtgctca tcattggaaa acgttcttcg    4620
gggcgaaaac tctcaaggat cttaccgctg ttgagatcca gttcgatgta acccactcgt    4680
gcacccaact gatcttcagc atcttttact ttcaccagcg tttctgggtg agcaaaaaca    4740
ggaaggcaaa atgccgcaaa aaagggaata agggcgacac ggaaatgttg aatactcata    4800
ctcttccttt ttcaatatta ttgaagcatt tatcagggtt attgtctcat gagcggatac    4860
atatttgaat gtatttagaa aaataaacaa ataggggttc cgcgcacatt tccccgaaaa    4920
gtgccacctg acgtctaaga aaccattatt atcatgacat taacctataa aaataggcgt    4980
atcacgaggc cctttcgtc tcgcgcgttt cggtgatgac ggtgaaaacc tctgacacat    5040
gcagctcccg gagacggtca cagcttgtct gtaagcggat gccgggagca gacaagcccg    5100
tcagggcgcg tcagcgggtg ttggcgggtg tcggggctgg cttaactatg cggcatcaga    5160
gcagattgta ctgagagtgc accatatgcg gtgtgaaata ccgcacagat gcgtaaggag    5220
aaaataccgc atcaggaaat tgtaaacgtt aatattttgt taaaattcgc gttaaatttt    5280
tgttaaatca gctcattttt taaccaatag gccgaaatcg gcaaaatccc ttataaatca    5340
```

```
aaagaataga ccgagatagg gttgagtgtt gttccagttt ggaacaagag tccactatta    5400
aagaacgtgg actccaacgt caaagggcga aaaccgtct  atcagggcga tggcccacta    5460
cgtgaaccat cacctaatc  aagttttttg gggtcgaggt gccgtaaagc actaaatcgg    5520
aaccctaaag ggagcccccg atttagagct tgacggggaa agccggcgaa cgtggcgaga    5580
aaggaaggga agaaagcgaa aggagcgggc gctagggcgc tggcaagtgt agcggtcacg    5640
ctgcgcgtaa ccaccacacc cgccgcgctt aatgcgccgc tacagggcgc gtcgcgccat    5700
tcgccattca ggctacgcaa ctgttgggaa gggcgatcgg tgcgggcctc ttcgctatta    5760
cgccagctgg cgaaggggg  atgtgctgca aggcgattaa gttgggtaac gccagggttt    5820
tcccagtcac gacgttgtaa aacgacggcc agtgaatt                            5858
```

<210> SEQ ID NO 5
<211> LENGTH: 581
<212> TYPE: PRT
<213> ORGANISM: artificial
<220> FEATURE:
<223> OTHER INFORMATION: fusion trimer

<400> SEQUENCE: 5

```
Met Gly Ile Gln Gly Gly Ser Val Leu Phe Gly Leu Leu Leu Val Leu
1               5                   10                  15

Ala Val Phe Cys His Ser Gly His Ser Leu Gln Ser Tyr Asn Pro Pro
            20                  25                  30

Arg Thr Pro Pro Met Ile Leu Arg Thr Ser Glu Glu Thr Ile Ser Thr
        35                  40                  45

Val Gln Glu Lys Gln Gln Asn Ile Ser Pro Leu Val Arg Glu Arg Gly
    50                  55                  60

Pro Gln Arg Val Ala Ala His Ile Thr Gly Thr Arg Gly Arg Ser Asn
65                  70                  75                  80

Thr Leu Ser Ser Pro Asn Ser Lys Asn Glu Lys Ala Leu Gly Arg Lys
                85                  90                  95

Ile Asn Ser Trp Glu Ser Ser Arg Ser Gly His Ser Phe Leu Ser Asn
            100                 105                 110

Leu His Leu Arg Asn Gly Glu Leu Val Ile His Glu Lys Gly Phe Tyr
        115                 120                 125

Tyr Ile Tyr Ser Gln Thr Tyr Phe Arg Phe Gln Glu Glu Ile Lys Glu
    130                 135                 140

Asn Thr Lys Asn Asp Lys Gln Met Val Gln Tyr Ile Tyr Lys Tyr Thr
145                 150                 155                 160

Ser Tyr Pro Asp Pro Ile Leu Leu Met Lys Ser Ala Arg Asn Ser Cys
                165                 170                 175

Trp Ser Lys Asp Ala Glu Tyr Gly Leu Tyr Ser Ile Tyr Gln Gly Gly
            180                 185                 190

Ile Phe Glu Leu Lys Glu Asn Asp Arg Ile Phe Val Ser Val Thr Asn
        195                 200                 205

Glu His Leu Ile Asp Met Asp His Glu Ala Ser Phe Phe Gly Ala Phe
    210                 215                 220

Leu Val Gly Arg Ser Gln Asn Ile Ser Pro Leu Val Arg Glu Arg Gly
225                 230                 235                 240

Pro Gln Arg Val Ala Ala His Ile Thr Gly Thr Arg Gly Arg Ser Asn
                245                 250                 255

Thr Leu Ser Ser Pro Asn Ser Lys Asn Glu Lys Ala Leu Gly Arg Lys
            260                 265                 270
```

```
Ile Asn Ser Trp Glu Ser Ser Arg Ser Gly His Ser Phe Leu Ser Asn
            275                 280                 285

Leu His Leu Arg Asn Gly Glu Leu Val Ile His Glu Lys Gly Phe Tyr
        290                 295                 300

Tyr Ile Tyr Ser Gln Thr Tyr Phe Arg Phe Gln Glu Glu Ile Lys Glu
305                 310                 315                 320

Asn Thr Lys Asn Asp Lys Gln Met Val Gln Tyr Ile Tyr Lys Tyr Thr
                325                 330                 335

Ser Tyr Pro Asp Pro Ile Leu Leu Met Lys Ser Ala Arg Asn Ser Cys
            340                 345                 350

Trp Ser Lys Asp Ala Glu Tyr Gly Leu Tyr Ser Ile Tyr Gln Gly Gly
        355                 360                 365

Ile Phe Glu Leu Lys Glu Asn Asp Arg Ile Phe Val Ser Val Thr Asn
370                 375                 380

Glu His Leu Ile Asp Met Asp His Glu Ala Ser Phe Phe Gly Ala Phe
385                 390                 395                 400

Leu Val Gly Arg Ser Gln Asn Ile Ser Pro Leu Val Arg Glu Arg Gly
                405                 410                 415

Pro Gln Arg Val Ala Ala His Ile Thr Gly Thr Arg Gly Arg Ser Asn
            420                 425                 430

Thr Leu Ser Ser Pro Asn Ser Lys Asn Glu Lys Ala Leu Gly Arg Lys
        435                 440                 445

Ile Asn Ser Trp Glu Ser Ser Arg Ser Gly His Ser Phe Leu Ser Asn
450                 455                 460

Leu His Leu Arg Asn Gly Glu Leu Val Ile His Glu Lys Gly Phe Tyr
465                 470                 475                 480

Tyr Ile Tyr Ser Gln Thr Tyr Phe Arg Phe Gln Glu Glu Ile Lys Glu
                485                 490                 495

Asn Thr Lys Asn Asp Lys Gln Met Val Gln Tyr Ile Tyr Lys Tyr Thr
            500                 505                 510

Ser Tyr Pro Asp Pro Ile Leu Leu Met Lys Ser Ala Arg Asn Ser Cys
        515                 520                 525

Trp Ser Lys Asp Ala Glu Tyr Gly Leu Tyr Ser Ile Tyr Gln Gly Gly
530                 535                 540

Ile Phe Glu Leu Lys Glu Asn Asp Arg Ile Phe Val Ser Val Thr Asn
545                 550                 555                 560

Glu His Leu Ile Asp Met Asp His Glu Ala Ser Phe Phe Gly Ala Phe
                565                 570                 575

Leu Val Gly Arg Ser
            580
```

<210> SEQ ID NO 6
<211> LENGTH: 591
<212> TYPE: PRT
<213> ORGANISM: artificial
<220> FEATURE:
<223> OTHER INFORMATION: fusion trimer

<400> SEQUENCE: 6

```
Met Gly Ile Gln Gly Gly Ser Val Leu Phe Gly Leu Leu Leu Val Leu
1               5                   10                  15

Ala Val Phe Cys His Ser Gly His Ser Leu Gln Ser Tyr Asn Pro Pro
            20                  25                  30

Arg Thr Pro Pro Met Ile Leu Arg Thr Ser Glu Glu Thr Ile Ser Thr
        35                  40                  45
```

```
Val Gln Glu Lys Gln Gln Asn Ile Ser Pro Leu Val Arg Glu Arg Gly
 50                  55                  60

Pro Gln Arg Val Ala Ala His Ile Thr Gly Thr Arg Gly Arg Ser Asn
 65                  70                  75                  80

Thr Leu Ser Ser Pro Asn Ser Lys Asn Glu Lys Ala Leu Gly Arg Lys
                 85                  90                  95

Ile Asn Ser Trp Glu Ser Ser Arg Ser Gly His Ser Phe Leu Ser Asn
                100                 105                 110

Leu His Leu Arg Asn Gly Glu Leu Val Ile His Glu Lys Gly Phe Tyr
            115                 120                 125

Tyr Ile Tyr Ser Gln Thr Tyr Phe Arg Phe Gln Glu Glu Ile Lys Glu
    130                 135                 140

Asn Thr Lys Asn Asp Lys Gln Met Val Gln Tyr Ile Tyr Lys Tyr Thr
145                 150                 155                 160

Ser Tyr Pro Asp Pro Ile Leu Leu Met Lys Ser Ala Arg Asn Ser Cys
                165                 170                 175

Trp Ser Lys Asp Ala Glu Tyr Gly Leu Tyr Ser Ile Tyr Gln Gly Gly
            180                 185                 190

Ile Phe Glu Leu Lys Glu Asn Asp Arg Ile Phe Val Ser Val Thr Asn
    195                 200                 205

Glu His Leu Ile Asp Met Asp His Glu Ala Ser Phe Phe Gly Ala Phe
    210                 215                 220

Leu Val Gly Arg Ser Gln Asn Ile Ser Pro Leu Val Arg Glu Arg Gly
225                 230                 235                 240

Pro Gln Arg Val Ala Ala His Ile Thr Gly Thr Arg Gly Arg Ser Asn
                245                 250                 255

Thr Leu Ser Ser Pro Asn Ser Lys Asn Glu Lys Ala Leu Gly Arg Lys
            260                 265                 270

Ile Asn Ser Trp Glu Ser Ser Arg Ser Gly His Ser Phe Leu Ser Asn
    275                 280                 285

Leu His Leu Arg Asn Gly Glu Leu Val Ile His Glu Lys Gly Phe Tyr
    290                 295                 300

Tyr Ile Tyr Ser Gln Thr Tyr Phe Arg Phe Gln Glu Glu Ile Lys Glu
305                 310                 315                 320

Asn Thr Lys Asn Asp Lys Gln Met Val Gln Tyr Ile Tyr Lys Tyr Thr
                325                 330                 335

Ser Tyr Pro Asp Pro Ile Leu Leu Met Lys Ser Ala Arg Asn Ser Cys
            340                 345                 350

Trp Ser Lys Asp Ala Glu Tyr Gly Leu Tyr Ser Ile Tyr Gln Gly Gly
    355                 360                 365

Ile Phe Glu Leu Lys Glu Asn Asp Arg Ile Phe Val Ser Val Thr Asn
    370                 375                 380

Glu His Leu Ile Asp Met Asp His Glu Ala Ser Phe Phe Gly Ala Phe
385                 390                 395                 400

Leu Val Gly Arg Ser Gln Asn Ile Ser Pro Leu Val Arg Glu Arg Gly
                405                 410                 415

Pro Gln Arg Val Ala Ala His Ile Thr Gly Thr Arg Gly Arg Ser Asn
            420                 425                 430

Thr Leu Ser Ser Pro Asn Ser Lys Asn Glu Lys Ala Leu Gly Arg Lys
    435                 440                 445

Ile Asn Ser Trp Glu Ser Ser Arg Ser Gly His Ser Phe Leu Ser Asn
    450                 455                 460
```

```
Leu His Leu Arg Asn Gly Glu Leu Val Ile His Glu Lys Gly Phe Tyr
465                 470                 475                 480

Tyr Ile Tyr Ser Gln Thr Tyr Phe Arg Phe Gln Glu Glu Ile Lys Glu
                485                 490                 495

Asn Thr Lys Asn Asp Lys Gln Met Val Gln Tyr Ile Tyr Lys Tyr Thr
            500                 505                 510

Ser Tyr Pro Asp Pro Ile Leu Leu Met Lys Ser Ala Arg Asn Ser Cys
        515                 520                 525

Trp Ser Lys Asp Ala Glu Tyr Gly Leu Tyr Ser Ile Tyr Gln Gly Gly
    530                 535                 540

Ile Phe Glu Leu Lys Glu Asn Asp Arg Ile Phe Val Ser Val Thr Asn
545                 550                 555                 560

Glu His Leu Ile Asp Met Asp His Glu Ala Ser Phe Phe Gly Ala Phe
                565                 570                 575

Leu Val Gly Gly Gly Ser His His His His His His Arg Ser
                580                 585                 590

<210> SEQ ID NO 7
<211> LENGTH: 587
<212> TYPE: PRT
<213> ORGANISM: artificial
<220> FEATURE:
<223> OTHER INFORMATION: fusion trimer

<400> SEQUENCE: 7

Met Gly Ile Gln Gly Gly Ser Val Leu Phe Gly Leu Leu Leu Val Leu
1               5                   10                  15

Ala Val Phe Cys His Ser Gly His Ser Leu Gln Ser Tyr Asn Pro Pro
                20                  25                  30

Arg Thr Pro Pro Met Ile Leu Arg Thr Ser Glu Glu Thr Ile Ser Thr
            35                  40                  45

Val Gln Glu Lys Gln Gln Asn Ile Ser Pro Leu Val Arg Glu Arg Gly
        50                  55                  60

Pro Gln Arg Val Ala Ala His Ile Thr Gly Thr Arg Gly Arg Ser Asn
65                  70                  75                  80

Thr Leu Ser Ser Pro Asn Ser Lys Asn Glu Lys Ala Leu Gly Arg Lys
                85                  90                  95

Ile Asn Ser Trp Glu Ser Ser Arg Ser Gly His Ser Phe Leu Ser Asn
            100                 105                 110

Leu His Leu Arg Asn Gly Glu Leu Val Ile His Glu Lys Gly Phe Tyr
        115                 120                 125

Tyr Ile Tyr Ser Gln Thr Tyr Phe Arg Phe Gln Glu Glu Ile Lys Glu
    130                 135                 140

Asn Thr Lys Asn Asp Lys Gln Met Val Gln Tyr Ile Tyr Lys Tyr Thr
145                 150                 155                 160

Ser Tyr Pro Asp Pro Ile Leu Leu Met Lys Ser Ala Arg Asn Ser Cys
                165                 170                 175

Trp Ser Lys Asp Ala Glu Tyr Gly Leu Tyr Ser Ile Tyr Gln Gly Gly
            180                 185                 190

Ile Phe Glu Leu Lys Glu Asn Asp Arg Ile Phe Val Ser Val Thr Asn
        195                 200                 205

Glu His Leu Ile Asp Met Asp His Glu Ala Ser Phe Phe Gly Ala Phe
    210                 215                 220

Leu Val Gly Arg Ser Gln Asn Ile Ser Pro Leu Val Arg Glu Arg Gly
225                 230                 235                 240
```

```
Pro Gln Arg Val Ala His Ile Thr Gly Thr Gly Arg Ser Asn
            245                 250                 255

Thr Leu Ser Ser Pro Asn Ser Lys Asn Glu Lys Ala Leu Gly Arg Lys
        260                 265                 270

Ile Asn Ser Trp Glu Ser Ser Arg Ser Gly His Ser Phe Leu Ser Asn
        275                 280                 285

Leu His Leu Arg Asn Gly Glu Leu Val Ile His Glu Lys Gly Phe Tyr
        290                 295                 300

Tyr Ile Tyr Ser Gln Thr Tyr Phe Arg Phe Gln Glu Ile Lys Glu
305                 310                 315                 320

Asn Thr Lys Asn Asp Lys Gln Met Val Gln Tyr Ile Tyr Lys Tyr Thr
                325                 330                 335

Ser Tyr Pro Asp Pro Ile Leu Leu Met Lys Ser Ala Arg Asn Ser Cys
                340                 345                 350

Trp Ser Lys Asp Ala Glu Tyr Gly Leu Tyr Ser Ile Tyr Gln Gly Gly
                355                 360                 365

Ile Phe Glu Leu Lys Glu Asn Asp Arg Ile Phe Val Ser Val Thr Asn
        370                 375                 380

Glu His Leu Ile Asp Met Asp His Glu Ala Ser Phe Phe Gly Ala Phe
385                 390                 395                 400

Leu Val Gly Arg Ser His His His His His Gln Asn Ile Ser Pro
                405                 410                 415

Leu Val Arg Glu Arg Gly Pro Gln Arg Val Ala Ala His Ile Thr Gly
                420                 425                 430

Thr Arg Gly Arg Ser Asn Thr Leu Ser Ser Pro Asn Ser Lys Asn Glu
        435                 440                 445

Lys Ala Leu Gly Arg Lys Ile Asn Ser Trp Glu Ser Ser Arg Ser Gly
450                 455                 460

His Ser Phe Leu Ser Asn Leu His Leu Arg Asn Gly Glu Leu Val Ile
465                 470                 475                 480

His Glu Lys Gly Phe Tyr Tyr Ile Tyr Ser Gln Thr Tyr Phe Arg Phe
                485                 490                 495

Gln Glu Glu Ile Lys Glu Asn Thr Lys Asn Asp Lys Gln Met Val Gln
                500                 505                 510

Tyr Ile Tyr Lys Tyr Thr Ser Tyr Pro Asp Pro Ile Leu Leu Met Lys
        515                 520                 525

Ser Ala Arg Asn Ser Cys Trp Ser Lys Asp Ala Glu Tyr Gly Leu Tyr
        530                 535                 540

Ser Ile Tyr Gln Gly Gly Ile Phe Glu Leu Lys Glu Asn Asp Arg Ile
545                 550                 555                 560

Phe Val Ser Val Thr Asn Glu His Leu Ile Asp Met Asp His Glu Ala
                565                 570                 575

Ser Phe Phe Gly Ala Phe Leu Val Gly Arg Ser
                580                 585

<210> SEQ ID NO 8
<211> LENGTH: 581
<212> TYPE: PRT
<213> ORGANISM: artificial
<220> FEATURE:
<223> OTHER INFORMATION: trimer fusion

<400> SEQUENCE: 8

Met Gly Ile Gln Gly Gly Ser Val Leu Phe Gly Leu Leu Leu Val Leu
1               5                   10                  15
```

```
Ala Val Phe Cys His Ser Gly His Ser Leu Gln Ser Tyr Asn Pro Pro
            20                  25                  30
Arg Thr Pro Pro Met Ile Leu Arg Thr Ser Glu Glu Thr Ile Ser Thr
        35                  40                  45
Val Gln Glu Lys Gln Gln Asn Ile Ser Pro Leu Val Arg Glu Arg Gly
    50                  55                  60
Pro Gln Arg Val Ala Ala His Ile Thr Gly Thr Arg Gly Arg Ser Asn
65                  70                  75                  80
Thr Leu Ser Ser Pro Asn Ser Lys Asn Glu Lys Ala Leu Gly Arg Lys
                85                  90                  95
Ile Asn Ser Trp Glu Ser Ser Arg Ser Gly His Ser Phe Leu Ser Asn
            100                 105                 110
Leu His Leu Arg Asn Gly Glu Leu Val Ile His Glu Lys Gly Phe Tyr
        115                 120                 125
Tyr Ile Tyr Ser Gln Thr Tyr Phe Arg Phe Gln Glu Glu Ile Lys Glu
    130                 135                 140
Asn Thr Lys Asn Asp Lys Gln Met Val Gln Tyr Ile Tyr Lys Tyr Thr
145                 150                 155                 160
Ser Tyr Pro Asp Pro Ile Leu Leu Met Lys Ser Ala Arg Asn Ser Cys
                165                 170                 175
Trp Ser Lys Asp Ala Glu Tyr Gly Leu Tyr Ser Ile Tyr Gln Gly Gly
            180                 185                 190
Ile Phe Glu Leu Lys Glu Asn Asp Arg Ile Phe Val Ser Val Thr Asn
        195                 200                 205
Glu His Leu Ile Asp Met Asp His Glu Ala Ser Phe Phe Gly Ala Phe
    210                 215                 220
Leu Val Gly Arg Ser Gln Asn Ile Ser Pro Leu Val Arg Glu Arg Gly
225                 230                 235                 240
Pro Gln Arg Val Ala Ala His Ile Thr Gly Thr Arg Gly Arg Ser Asn
                245                 250                 255
Thr Leu Ser Ser Pro Asn Ser Lys Asn Glu Lys Ala Leu Gly Arg Lys
            260                 265                 270
Ile Asn Ser Trp Glu Ser Ser Arg Ser Gly His Ser Phe Leu Ser Asn
        275                 280                 285
Leu His Leu Arg Asn Gly Glu Leu Val Ile His Glu Lys Gly Phe Tyr
    290                 295                 300
Tyr Ile Tyr Ser Gln Thr Tyr Phe Arg Phe Gln Glu Glu Ile Lys Glu
305                 310                 315                 320
Asn Thr Lys Asn Asp Lys Gln Met Val Gln Tyr Ile Tyr Lys Tyr Thr
                325                 330                 335
Ser Tyr Pro Asp Pro Ile Leu Leu Met Lys Ser Ala Arg Asn Ser Cys
            340                 345                 350
Trp Ser Lys Asp Ala Glu Tyr Gly Leu Tyr Ser Ile Tyr Gln Gly Gly
        355                 360                 365
Ile Phe Glu Leu Lys Glu Asn Asp Arg Ile Phe Val Ser Val Thr Asn
    370                 375                 380
Glu His Leu Ile Asp Met Asp His Glu Ala Ser Phe Phe Gly Ala Phe
385                 390                 395                 400
Leu Val Gly Arg Ser His His His His His Val Arg Glu Arg Gly
                405                 410                 415
Pro Gln Arg Val Ala Ala His Ile Thr Gly Thr Arg Gly Arg Ser Asn
            420                 425                 430
Thr Leu Ser Ser Pro Asn Ser Lys Asn Glu Lys Ala Leu Gly Arg Lys
```

```
            435                 440                 445
Ile Asn Ser Trp Glu Ser Ser Arg Ser Gly His Ser Phe Leu Ser Asn
450                 455                 460

Leu His Leu Arg Asn Gly Glu Leu Val Ile His Glu Lys Gly Phe Tyr
465                 470                 475                 480

Tyr Ile Tyr Ser Gln Thr Tyr Phe Arg Phe Gln Glu Ile Lys Glu
                485                 490                 495

Asn Thr Lys Asn Asp Lys Gln Met Val Gln Tyr Ile Tyr Lys Tyr Thr
                500                 505                 510

Ser Tyr Pro Asp Pro Ile Leu Leu Met Lys Ser Ala Arg Asn Ser Cys
                515                 520                 525

Trp Ser Lys Asp Ala Glu Tyr Gly Leu Tyr Ser Ile Tyr Gln Gly Gly
                530                 535                 540

Ile Phe Glu Leu Lys Glu Asn Asp Arg Ile Phe Val Ser Val Thr Asn
545                 550                 555                 560

Glu His Leu Ile Asp Met Asp His Glu Ala Ser Phe Phe Gly Ala Phe
                565                 570                 575

Leu Val Gly Arg Ser
                580

<210> SEQ ID NO 9
<211> LENGTH: 884
<212> TYPE: PRT
<213> ORGANISM: artificial
<220> FEATURE:
<223> OTHER INFORMATION: mesothelin-TR3 fusion

<400> SEQUENCE: 9

Met Gly Ile Gln Gly Gly Ser Val Leu Phe Gly Leu Leu Leu Val Leu
1               5                   10                  15

Ala Val Phe Cys His Ser Gly His Ser Leu Gln Ser Tyr Asn Pro Pro
                20                  25                  30

Arg Thr Asp Tyr Lys Asp Asp Asp Lys Gln Ile Ser Gly Gly Gly
            35                  40                  45

Ser Glu Val Glu Lys Thr Ala Cys Pro Ser Gly Lys Lys Ala Arg Glu
50                  55                  60

Ile Asp Glu Ser Leu Ile Phe Tyr Lys Lys Trp Glu Leu Glu Ala Cys
65                  70                  75                  80

Val Asp Ala Ala Leu Leu Ala Thr Gln Met Asp Arg Val Asn Ala Ile
                85                  90                  95

Pro Phe Thr Tyr Glu Gln Leu Asp Val Leu Lys His Lys Leu Asp Glu
                100                 105                 110

Leu Tyr Pro Gln Gly Tyr Pro Glu Ser Val Ile Gln His Leu Gly Tyr
                115                 120                 125

Leu Phe Leu Lys Met Ser Pro Glu Asp Ile Arg Lys Trp Asn Val Thr
130                 135                 140

Ser Leu Glu Thr Leu Lys Ala Leu Leu Glu Val Asn Lys Gly His Glu
145                 150                 155                 160

Met Ser Pro Gln Val Ala Thr Leu Ile Asp Arg Phe Val Lys Gly Arg
                165                 170                 175

Gly Gln Leu Asp Lys Asp Thr Leu Asp Thr Leu Thr Ala Phe Tyr Pro
                180                 185                 190

Gly Tyr Leu Cys Ser Leu Ser Pro Glu Glu Leu Ser Ser Val Pro Pro
                195                 200                 205

Ser Ser Ile Trp Ala Val Arg Pro Gln Asp Leu Asp Thr Cys Asp Pro
```

-continued

```
                210                 215                 220
Arg Gln Leu Asp Val Leu Tyr Pro Lys Ala Arg Leu Ala Phe Gln Asn
225                 230                 235                 240

Met Asn Gly Ser Glu Tyr Phe Val Lys Ile Gln Ser Phe Leu Gly Gly
                245                 250                 255

Ala Pro Thr Glu Asp Leu Lys Ala Leu Ser Gln Gln Asn Val Ser Met
                260                 265                 270

Asp Leu Ala Thr Phe Met Lys Leu Arg Thr Asp Ala Val Leu Pro Leu
                275                 280                 285

Thr Val Ala Glu Val Gln Lys Leu Leu Gly Pro His Val Glu Gly Leu
                290                 295                 300

Lys Ala Glu Glu Arg His Arg Pro Val Arg Asp Trp Ile Leu Arg Gln
305                 310                 315                 320

Arg Gln Asp Asp Leu Asp Thr Leu Gly Leu Gly Leu Gln Gly Leu Arg
                325                 330                 335

Thr Pro Pro Met Ile Leu Arg Thr Ser Glu Glu Thr Ile Ser Thr Val
                340                 345                 350

Gln Glu Lys Gln Gln Asn Ile Ser Pro Leu Val Arg Glu Arg Gly Pro
                355                 360                 365

Gln Arg Val Ala Ala His Ile Thr Gly Thr Arg Gly Arg Ser Asn Thr
370                 375                 380

Leu Ser Ser Pro Asn Ser Lys Asn Glu Lys Ala Leu Gly Arg Lys Ile
385                 390                 395                 400

Asn Ser Trp Glu Ser Ser Arg Ser Gly His Ser Phe Leu Ser Asn Leu
                405                 410                 415

His Leu Arg Asn Gly Glu Leu Val Ile His Glu Lys Gly Phe Tyr Tyr
                420                 425                 430

Ile Tyr Ser Gln Thr Tyr Phe Arg Phe Gln Glu Glu Ile Lys Glu Asn
                435                 440                 445

Thr Lys Asn Asp Lys Gln Met Val Gln Tyr Ile Tyr Lys Tyr Thr Ser
                450                 455                 460

Tyr Pro Asp Pro Ile Leu Leu Met Lys Ser Ala Arg Asn Ser Cys Trp
465                 470                 475                 480

Ser Lys Asp Ala Glu Tyr Gly Leu Tyr Ser Ile Tyr Gln Gly Gly Ile
                485                 490                 495

Phe Glu Leu Lys Glu Asn Asp Arg Ile Phe Val Ser Val Thr Asn Glu
                500                 505                 510

His Leu Ile Asp Met Asp His Glu Ala Ser Phe Phe Gly Ala Phe Leu
                515                 520                 525

Val Gly Arg Ser Gln Asn Ile Ser Pro Leu Val Arg Glu Arg Gly Pro
                530                 535                 540

Gln Arg Val Ala Ala His Ile Thr Gly Thr Arg Gly Arg Ser Asn Thr
545                 550                 555                 560

Leu Ser Ser Pro Asn Ser Lys Asn Glu Lys Ala Leu Gly Arg Lys Ile
                565                 570                 575

Asn Ser Trp Glu Ser Ser Arg Ser Gly His Ser Phe Leu Ser Asn Leu
                580                 585                 590

His Leu Arg Asn Gly Glu Leu Val Ile His Glu Lys Gly Phe Tyr Tyr
                595                 600                 605

Ile Tyr Ser Gln Thr Tyr Phe Arg Phe Gln Glu Glu Ile Lys Glu Asn
                610                 615                 620

Thr Lys Asn Asp Lys Gln Met Val Gln Tyr Ile Tyr Lys Tyr Thr Ser
625                 630                 635                 640
```

```
Tyr Pro Asp Pro Ile Leu Leu Met Lys Ser Ala Arg Asn Ser Cys Trp
            645                 650                 655

Ser Lys Asp Ala Glu Tyr Gly Leu Tyr Ser Ile Tyr Gln Gly Gly Ile
        660                 665                 670

Phe Glu Leu Lys Glu Asn Asp Arg Ile Phe Val Ser Val Thr Asn Glu
    675                 680                 685

His Leu Ile Asp Met Asp His Glu Ala Ser Phe Phe Gly Ala Phe Leu
690                 695                 700

Val Gly Arg Ser Gln Asn Ile Ser Pro Leu Val Arg Glu Arg Gly Pro
705                 710                 715                 720

Gln Arg Val Ala Ala His Ile Thr Gly Thr Arg Gly Arg Ser Asn Thr
                725                 730                 735

Leu Ser Ser Pro Asn Ser Lys Asn Glu Lys Ala Leu Gly Arg Lys Ile
            740                 745                 750

Asn Ser Trp Glu Ser Ser Arg Ser Gly His Ser Phe Leu Ser Asn Leu
        755                 760                 765

His Leu Arg Asn Gly Glu Leu Val Ile His Glu Lys Gly Phe Tyr Tyr
    770                 775                 780

Ile Tyr Ser Gln Thr Tyr Phe Arg Phe Gln Glu Glu Ile Lys Glu Asn
785                 790                 795                 800

Thr Lys Asn Asp Lys Gln Met Val Gln Tyr Ile Tyr Lys Tyr Thr Ser
                805                 810                 815

Tyr Pro Asp Pro Ile Leu Leu Met Lys Ser Ala Arg Asn Ser Cys Trp
            820                 825                 830

Ser Lys Asp Ala Glu Tyr Gly Leu Tyr Ser Ile Tyr Gln Gly Gly Ile
        835                 840                 845

Phe Glu Leu Lys Glu Asn Asp Arg Ile Phe Val Ser Val Thr Asn Glu
    850                 855                 860

His Leu Ile Asp Met Asp His Glu Ala Ser Phe Phe Gly Ala Phe Leu
865                 870                 875                 880

Val Gly Arg Ser

<210> SEQ ID NO 10
<211> LENGTH: 890
<212> TYPE: PRT
<213> ORGANISM: artificial
<220> FEATURE:
<223> OTHER INFORMATION: mesothelin-TR3 fusion

<400> SEQUENCE: 10

Met Gly Ile Gln Gly Gly Ser Val Leu Phe Gly Leu Leu Leu Val Leu
1               5                   10                  15

Ala Val Phe Cys His Ser Gly His Ser Leu Gln Ser Tyr Asn Pro Pro
            20                  25                  30

Arg Thr Asp Tyr Lys Asp Asp Asp Lys Gln Ile Ser Gly Gly Gly
        35                  40                  45

Ser Glu Val Glu Lys Thr Ala Cys Pro Ser Gly Lys Lys Ala Arg Glu
    50                  55                  60

Ile Asp Glu Ser Leu Ile Phe Tyr Lys Lys Trp Glu Leu Glu Ala Cys
65                  70                  75                  80

Val Asp Ala Ala Leu Leu Ala Thr Gln Met Asp Arg Val Asn Ala Ile
                85                  90                  95

Pro Phe Thr Tyr Glu Gln Leu Asp Val Leu Lys His Lys Leu Asp Glu
            100                 105                 110
```

-continued

```
Leu Tyr Pro Gln Gly Tyr Pro Glu Ser Val Ile Gln His Leu Gly Tyr
            115                 120                 125

Leu Phe Leu Lys Met Ser Pro Glu Asp Ile Arg Lys Trp Asn Val Thr
130                 135                 140

Ser Leu Glu Thr Leu Lys Ala Leu Leu Glu Val Asn Lys Gly His Glu
145                 150                 155                 160

Met Ser Pro Gln Val Ala Thr Leu Ile Asp Arg Phe Val Lys Gly Arg
                165                 170                 175

Gly Gln Leu Asp Lys Asp Thr Leu Asp Thr Leu Thr Ala Phe Tyr Pro
            180                 185                 190

Gly Tyr Leu Cys Ser Leu Ser Pro Glu Glu Leu Ser Ser Val Pro Pro
        195                 200                 205

Ser Ser Ile Trp Ala Val Arg Pro Gln Asp Leu Asp Thr Cys Asp Pro
210                 215                 220

Arg Gln Leu Asp Val Leu Tyr Pro Lys Ala Arg Leu Ala Phe Gln Asn
225                 230                 235                 240

Met Asn Gly Ser Glu Tyr Phe Val Lys Ile Gln Ser Phe Leu Gly Gly
                245                 250                 255

Ala Pro Thr Glu Asp Leu Lys Ala Leu Ser Gln Gln Asn Val Ser Met
            260                 265                 270

Asp Leu Ala Thr Phe Met Lys Leu Arg Thr Asp Ala Val Leu Pro Leu
        275                 280                 285

Thr Val Ala Glu Val Gln Lys Leu Leu Gly Pro His Val Glu Gly Leu
    290                 295                 300

Lys Ala Glu Glu Arg His Arg Pro Val Arg Asp Trp Ile Leu Arg Gln
305                 310                 315                 320

Arg Gln Asp Asp Leu Asp Thr Leu Gly Leu Gly Leu Gln Gly Leu Arg
                325                 330                 335

Thr Pro Pro Met Ile Leu Arg Thr Ser Glu Thr Ile Ser Thr Val
            340                 345                 350

Gln Glu Lys Gln Gln Asn Ile Ser Pro Leu Val Arg Glu Arg Gly Pro
        355                 360                 365

Gln Arg Val Ala Ala His Ile Thr Gly Thr Arg Gly Arg Ser Asn Thr
370                 375                 380

Leu Ser Ser Pro Asn Ser Lys Asn Glu Lys Ala Leu Gly Arg Lys Ile
385                 390                 395                 400

Asn Ser Trp Glu Ser Ser Arg Ser Gly His Ser Phe Leu Ser Asn Leu
                405                 410                 415

His Leu Arg Asn Gly Glu Leu Val Ile His Glu Lys Gly Phe Tyr Tyr
            420                 425                 430

Ile Tyr Ser Gln Thr Tyr Phe Arg Phe Gln Glu Glu Ile Lys Glu Asn
        435                 440                 445

Thr Lys Asn Asp Lys Gln Met Val Gln Tyr Ile Tyr Lys Tyr Thr Ser
450                 455                 460

Tyr Pro Asp Pro Ile Leu Leu Met Lys Ser Ala Arg Asn Ser Cys Trp
465                 470                 475                 480

Ser Lys Asp Ala Glu Tyr Gly Leu Tyr Ser Ile Tyr Gln Gly Gly Ile
                485                 490                 495

Phe Glu Leu Lys Glu Asn Asp Arg Ile Phe Val Ser Val Thr Asn Glu
            500                 505                 510

His Leu Ile Asp Met Asp His Glu Ala Ser Phe Phe Gly Ala Phe Leu
        515                 520                 525

Val Gly Arg Ser Gln Asn Ile Ser Pro Leu Val Arg Glu Arg Gly Pro
```

```
Gln Arg Val Ala Ala His Ile Thr Gly Thr Arg Gly Arg Ser Asn Thr
545                 550                 555                 560

Leu Ser Ser Pro Asn Ser Lys Asn Glu Lys Ala Leu Gly Arg Lys Ile
                565                 570                 575

Asn Ser Trp Glu Ser Ser Arg Ser Gly His Ser Phe Leu Ser Asn Leu
            580                 585                 590

His Leu Arg Asn Gly Glu Leu Val Ile His Lys Gly Phe Tyr Tyr
        595                 600                 605

Ile Tyr Ser Gln Thr Tyr Phe Arg Phe Gln Glu Glu Ile Lys Glu Asn
    610                 615                 620

Thr Lys Asn Asp Lys Gln Met Val Gln Tyr Ile Tyr Lys Tyr Thr Ser
625                 630                 635                 640

Tyr Pro Asp Pro Ile Leu Leu Met Lys Ser Ala Arg Asn Ser Cys Trp
                645                 650                 655

Ser Lys Asp Ala Glu Tyr Gly Leu Tyr Ser Ile Tyr Gln Gly Gly Ile
            660                 665                 670

Phe Glu Leu Lys Glu Asn Asp Arg Ile Phe Val Ser Val Thr Asn Glu
        675                 680                 685

His Leu Ile Asp Met Asp His Glu Ala Ser Phe Phe Gly Ala Phe Leu
    690                 695                 700

Val Gly Arg Ser His His His His His Gln Asn Ile Ser Pro Leu
705                 710                 715                 720

Val Arg Glu Arg Gly Pro Gln Arg Val Ala Ala His Ile Thr Gly Thr
                725                 730                 735

Arg Gly Arg Ser Asn Thr Leu Ser Ser Pro Asn Ser Lys Asn Glu Lys
            740                 745                 750

Ala Leu Gly Arg Lys Ile Asn Ser Trp Glu Ser Ser Arg Ser Gly His
        755                 760                 765

Ser Phe Leu Ser Asn Leu His Leu Arg Asn Gly Glu Leu Val Ile His
    770                 775                 780

Glu Lys Gly Phe Tyr Tyr Ile Tyr Ser Gln Thr Tyr Phe Arg Phe Gln
785                 790                 795                 800

Glu Glu Ile Lys Glu Asn Thr Lys Asn Asp Lys Gln Met Val Gln Tyr
                805                 810                 815

Ile Tyr Lys Tyr Thr Ser Tyr Pro Asp Pro Ile Leu Leu Met Lys Ser
            820                 825                 830

Ala Arg Asn Ser Cys Trp Ser Lys Asp Ala Glu Tyr Gly Leu Tyr Ser
        835                 840                 845

Ile Tyr Gln Gly Gly Ile Phe Glu Leu Lys Glu Asn Asp Arg Ile Phe
    850                 855                 860

Val Ser Val Thr Asn Glu His Leu Ile Asp Met Asp His Glu Ala Ser
865                 870                 875                 880

Phe Phe Gly Ala Phe Leu Val Gly Arg Ser
                885                 890

<210> SEQ ID NO 11
<211> LENGTH: 666
<212> TYPE: PRT
<213> ORGANISM: artificial
<220> FEATURE:
<223> OTHER INFORMATION: meso64-TR3 fusion

<400> SEQUENCE: 11

Met Gly Ile Gln Gly Gly Ser Val Leu Phe Gly Leu Leu Leu Val Leu
```

-continued

```
1               5                   10                  15
Ala Val Phe Cys His Ser Gly His Ser Leu Gln Ser Tyr Asn Pro Pro
                20                  25                  30
Arg Thr Asp Tyr Lys Asp Asp Asp Lys Gln Ile Ser Gly Gly Gly
                35                  40                  45
Ser Glu Val Glu Lys Thr Ala Cys Pro Ser Gly Lys Lys Ala Arg Glu
50                      55                  60
Ile Asp Glu Ser Leu Ile Phe Tyr Lys Lys Trp Glu Leu Glu Ala Cys
65                  70                  75                  80
Val Asp Ala Ala Leu Leu Ala Thr Gln Met Asp Arg Val Asn Ala Ile
                    85                  90                  95
Pro Phe Thr Tyr Glu Gln Leu Asp Val Leu Lys His Lys Leu Asp Glu
                100                 105                 110
Leu Gly Gly Gly Ser Gly Thr Pro Pro Met Ile Leu Arg Thr Ser Glu
                115                 120                 125
Glu Thr Ile Ser Thr Val Gln Glu Lys Gln Gln Asn Ile Ser Pro Leu
                130                 135                 140
Val Arg Glu Arg Gly Pro Gln Arg Val Ala Ala His Ile Thr Gly Thr
145                 150                 155                 160
Arg Gly Arg Ser Asn Thr Leu Ser Ser Pro Asn Ser Lys Asn Glu Lys
                165                 170                 175
Ala Leu Gly Arg Lys Ile Asn Ser Trp Glu Ser Ser Arg Ser Gly His
                180                 185                 190
Ser Phe Leu Ser Asn Leu His Leu Arg Asn Gly Glu Leu Val Ile His
                195                 200                 205
Glu Lys Gly Phe Tyr Tyr Ile Tyr Ser Gln Thr Tyr Phe Arg Phe Gln
210                 215                 220
Glu Glu Ile Lys Glu Asn Thr Lys Asn Asp Lys Gln Met Val Gln Tyr
225                 230                 235                 240
Ile Tyr Lys Tyr Thr Ser Tyr Pro Asp Pro Ile Leu Leu Met Lys Ser
                245                 250                 255
Ala Arg Asn Ser Cys Trp Ser Lys Asp Ala Glu Tyr Gly Leu Tyr Ser
                260                 265                 270
Ile Tyr Gln Gly Gly Ile Phe Glu Leu Lys Glu Asn Asp Arg Ile Phe
                275                 280                 285
Val Ser Val Thr Asn Glu His Leu Ile Asp Met Asp His Glu Ala Ser
                290                 295                 300
Phe Phe Gly Ala Phe Leu Val Gly Arg Ser Gln Asn Ile Ser Pro Leu
305                 310                 315                 320
Val Arg Glu Arg Gly Pro Gln Arg Val Ala Ala His Ile Thr Gly Thr
                325                 330                 335
Arg Gly Arg Ser Asn Thr Leu Ser Ser Pro Asn Ser Lys Asn Glu Lys
                340                 345                 350
Ala Leu Gly Arg Lys Ile Asn Ser Trp Glu Ser Ser Arg Ser Gly His
                355                 360                 365
Ser Phe Leu Ser Asn Leu His Leu Arg Asn Gly Glu Leu Val Ile His
                370                 375                 380
Glu Lys Gly Phe Tyr Tyr Ile Tyr Ser Gln Thr Tyr Phe Arg Phe Gln
385                 390                 395                 400
Glu Glu Ile Lys Glu Asn Thr Lys Asn Asp Lys Gln Met Val Gln Tyr
                405                 410                 415
Ile Tyr Lys Tyr Thr Ser Tyr Pro Asp Pro Ile Leu Leu Met Lys Ser
                420                 425                 430
```

```
Ala Arg Asn Ser Cys Trp Ser Lys Asp Ala Glu Tyr Gly Leu Tyr Ser
        435                 440                 445

Ile Tyr Gln Gly Gly Ile Phe Glu Leu Lys Glu Asn Asp Arg Ile Phe
450                 455                 460

Val Ser Val Thr Asn Glu His Leu Ile Asp Met Asp His Glu Ala Ser
465                 470                 475                 480

Phe Phe Gly Ala Phe Leu Val Gly Arg Ser Gln Asn Ile Ser Pro Leu
                485                 490                 495

Val Arg Glu Arg Gly Pro Gln Arg Val Ala Ala His Ile Thr Gly Thr
            500                 505                 510

Arg Gly Arg Ser Asn Thr Leu Ser Ser Pro Asn Ser Lys Asn Glu Lys
        515                 520                 525

Ala Leu Gly Arg Lys Ile Asn Ser Trp Glu Ser Ser Arg Ser Gly His
    530                 535                 540

Ser Phe Leu Ser Asn Leu His Leu Arg Asn Gly Glu Leu Val Ile His
545                 550                 555                 560

Glu Lys Gly Phe Tyr Tyr Ile Tyr Ser Gln Thr Tyr Phe Arg Phe Gln
                565                 570                 575

Glu Glu Ile Lys Glu Asn Thr Lys Asn Asp Lys Gln Met Val Gln Tyr
            580                 585                 590

Ile Tyr Lys Tyr Thr Ser Tyr Pro Asp Pro Ile Leu Leu Met Lys Ser
        595                 600                 605

Ala Arg Asn Ser Cys Trp Ser Lys Asp Ala Glu Tyr Gly Leu Tyr Ser
    610                 615                 620

Ile Tyr Gln Gly Gly Ile Phe Glu Leu Lys Glu Asn Asp Arg Ile Phe
625                 630                 635                 640

Val Ser Val Thr Asn Glu His Leu Ile Asp Met Asp His Glu Ala Ser
                645                 650                 655

Phe Phe Gly Ala Phe Leu Val Gly Arg Ser
            660                 665

<210> SEQ ID NO 12
<211> LENGTH: 672
<212> TYPE: PRT
<213> ORGANISM: artificial
<220> FEATURE:
<223> OTHER INFORMATION: Meso64-TR3 fusion

<400> SEQUENCE: 12

Met Gly Ile Gln Gly Gly Ser Val Leu Phe Gly Leu Leu Val Leu
1               5                   10                  15

Ala Val Phe Cys His Ser Gly His Ser Leu Gln Ser Tyr Asn Pro Pro
                20                  25                  30

Arg Thr Asp Tyr Lys Asp Asp Asp Lys Gln Ile Ser Gly Gly Gly
            35                  40                  45

Ser Glu Val Glu Lys Thr Ala Cys Pro Ser Gly Lys Lys Ala Arg Glu
        50                  55                  60

Ile Asp Glu Ser Leu Ile Phe Tyr Lys Lys Trp Glu Leu Glu Ala Cys
65                  70                  75                  80

Val Asp Ala Ala Leu Leu Ala Thr Gln Met Asp Arg Val Asn Ala Ile
                85                  90                  95

Pro Phe Thr Tyr Glu Gln Leu Asp Val Leu Lys His Lys Leu Asp Glu
            100                 105                 110

Leu Gly Gly Gly Ser Gly Thr Pro Pro Met Ile Leu Arg Thr Ser Glu
        115                 120                 125
```

```
Glu Thr Ile Ser Thr Val Gln Glu Lys Gln Gln Asn Ile Ser Pro Leu
        130                 135                 140

Val Arg Glu Arg Gly Pro Gln Arg Val Ala Ala His Ile Thr Gly Thr
145                 150                 155                 160

Arg Gly Arg Ser Asn Thr Leu Ser Ser Pro Asn Ser Lys Asn Glu Lys
                165                 170                 175

Ala Leu Gly Arg Lys Ile Asn Ser Trp Glu Ser Ser Arg Ser Gly His
            180                 185                 190

Ser Phe Leu Ser Asn Leu His Leu Arg Asn Gly Glu Leu Val Ile His
        195                 200                 205

Glu Lys Gly Phe Tyr Tyr Ile Tyr Ser Gln Thr Tyr Phe Arg Phe Gln
210                 215                 220

Glu Glu Ile Lys Glu Asn Thr Lys Asn Asp Lys Gln Met Val Gln Tyr
225                 230                 235                 240

Ile Tyr Lys Tyr Thr Ser Tyr Pro Asp Pro Ile Leu Leu Met Lys Ser
                245                 250                 255

Ala Arg Asn Ser Cys Trp Ser Lys Asp Ala Glu Tyr Gly Leu Tyr Ser
            260                 265                 270

Ile Tyr Gln Gly Gly Ile Phe Glu Leu Lys Glu Asn Asp Arg Ile Phe
        275                 280                 285

Val Ser Val Thr Asn Glu His Leu Ile Asp Met Asp His Glu Ala Ser
290                 295                 300

Phe Phe Gly Ala Phe Leu Val Gly Arg Ser Gln Asn Ile Ser Pro Leu
305                 310                 315                 320

Val Arg Glu Arg Gly Pro Gln Arg Val Ala Ala His Ile Thr Gly Thr
                325                 330                 335

Arg Gly Arg Ser Asn Thr Leu Ser Ser Pro Asn Ser Lys Asn Glu Lys
            340                 345                 350

Ala Leu Gly Arg Lys Ile Asn Ser Trp Glu Ser Ser Arg Ser Gly His
        355                 360                 365

Ser Phe Leu Ser Asn Leu His Leu Arg Asn Gly Glu Leu Val Ile His
370                 375                 380

Glu Lys Gly Phe Tyr Tyr Ile Tyr Ser Gln Thr Tyr Phe Arg Phe Gln
385                 390                 395                 400

Glu Glu Ile Lys Glu Asn Thr Lys Asn Asp Lys Gln Met Val Gln Tyr
                405                 410                 415

Ile Tyr Lys Tyr Thr Ser Tyr Pro Asp Pro Ile Leu Leu Met Lys Ser
            420                 425                 430

Ala Arg Asn Ser Cys Trp Ser Lys Asp Ala Glu Tyr Gly Leu Tyr Ser
        435                 440                 445

Ile Tyr Gln Gly Gly Ile Phe Glu Leu Lys Glu Asn Asp Arg Ile Phe
450                 455                 460

Val Ser Val Thr Asn Glu His Leu Ile Asp Met Asp His Glu Ala Ser
465                 470                 475                 480

Phe Phe Gly Ala Phe Leu Val Gly Arg Ser His His His His His
                485                 490                 495

Gln Asn Ile Ser Pro Leu Val Arg Glu Arg Gly Pro Gln Arg Val Ala
            500                 505                 510

Ala His Ile Thr Gly Thr Arg Gly Arg Ser Asn Thr Leu Ser Ser Pro
        515                 520                 525

Asn Ser Lys Asn Glu Lys Ala Leu Gly Arg Lys Ile Asn Ser Trp Glu
530                 535                 540
```

-continued

```
Ser Ser Arg Ser Gly His Ser Phe Leu Ser Asn Leu His Leu Arg Asn
545             550             555             560

Gly Glu Leu Val Ile His Glu Lys Gly Phe Tyr Tyr Ile Tyr Ser Gln
                565             570             575

Thr Tyr Phe Arg Phe Gln Glu Glu Ile Lys Glu Asn Thr Lys Asn Asp
            580             585             590

Lys Gln Met Val Gln Tyr Ile Tyr Lys Tyr Thr Ser Tyr Pro Asp Pro
        595             600             605

Ile Leu Leu Met Lys Ser Ala Arg Asn Ser Cys Trp Ser Lys Asp Ala
        610             615             620

Glu Tyr Gly Leu Tyr Ser Ile Tyr Gln Gly Gly Ile Phe Glu Leu Lys
625             630             635             640

Glu Asn Asp Arg Ile Phe Val Ser Val Thr Asn Glu His Leu Ile Asp
                645             650             655

Met Asp His Glu Ala Ser Phe Phe Gly Ala Phe Leu Val Gly Arg Ser
            660             665             670
```